(12) United States Patent
Yoshimura et al.

(10) Patent No.: US 7,787,586 B2
(45) Date of Patent: Aug. 31, 2010

(54) DISPLAY METHOD OF X-RAY CT IMAGE OF MAXILLOFACIAL AREA, X-RAY CT APPARATUS AND X-RAY IMAGE DISPLAY APPARATUS

(75) Inventors: Takahiro Yoshimura, Kyoto (JP); Tomoyuki Sadakane, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 218 days.

(21) Appl. No.: 12/070,749

(22) Filed: Feb. 21, 2008

(65) Prior Publication Data

US 2008/0232540 A1    Sep. 25, 2008

(30) Foreign Application Priority Data

Feb. 22, 2007  (JP) .............................. 2007-042991
Mar. 19, 2007  (JP) .............................. 2007-071590
Feb. 21, 2008  (JP) .............................. 2008-040533

(51) Int. Cl.
*A61B 6/04* (2006.01)
*A61B 6/14* (2006.01)

(52) U.S. Cl. ............................................ 378/4; 378/38

(58) Field of Classification Search ...................... 378/4, 378/19, 38–40, 62, 68
See application file for complete search history.

(56) References Cited

U.S. PATENT DOCUMENTS 6,289,074 B1    9/2001  Arai et al.
6,493,415 B1    12/2002 Arai et al.
6,619,839 B2 *  9/2003  Yoshimura ................... 378/196
7,688,941 B2 *  3/2010  Thoms ......................... 378/38
2003/0215051 A1* 11/2003 Suzuki ......................... 378/19
2004/0066877 A1  4/2004  Arai et al.
2006/0203959 A1  9/2006  Spartiotis et al.

FOREIGN PATENT DOCUMENTS

| DE | 103 92 506 T5 | 5/2005 |
|---|---|---|
| JP | 08-215192 | 8/1996 |
| JP | 2001-333898 | 12/2001 |
| JP | 2002-11000 | 1/2002 |
| JP | 2004-329293 | 11/2004 |
| WO | WO 02/28285 | 4/2002 |
| WO | WO 2006/116488 | 11/2006 |
| WO | WO 2006/127416 | 11/2006 |

\* cited by examiner

*Primary Examiner*—Irakli Kiknadze
(74) *Attorney, Agent, or Firm*—William L. Androlia; H. Henry Koda

(57) ABSTRACT

A method of displaying a standard observational X-ray CT image for diagnostics for use in an X-ray CT apparatus or an X-ray CT image display apparatus and an apparatus for displaying the same image are disclosed. The standard observational X-ray CT image can be displayed as a display image of at least one of an X-ray CT sectional image and a three-dimensional CT volume image depending on its purpose. The present method involves a step of designating the interested area with respect to the maxillofacial area of the object, a step of producing the standard observational X-ray CT image of the designated interested area, based on the dental arch reference information prepared in advance, and a step of displaying on a display means the standard observational X-ray CT image of the object thus produced.

22 Claims, 32 Drawing Sheets

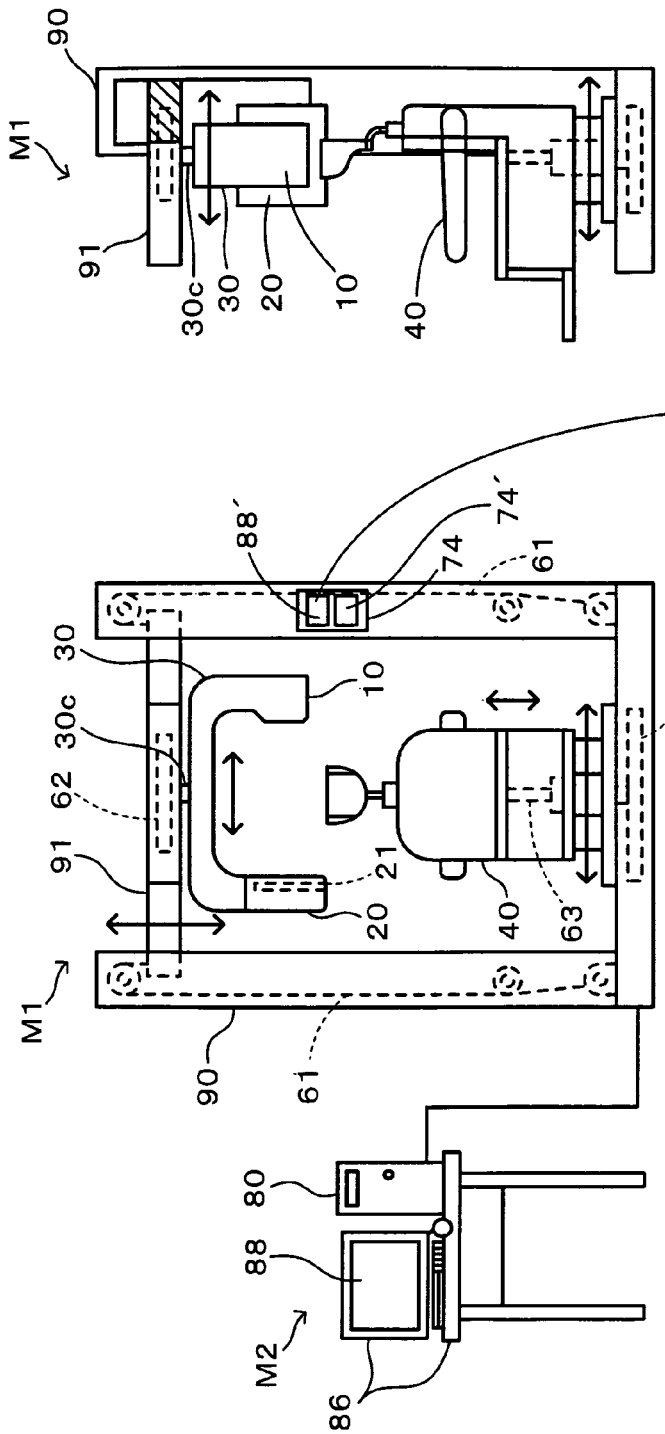
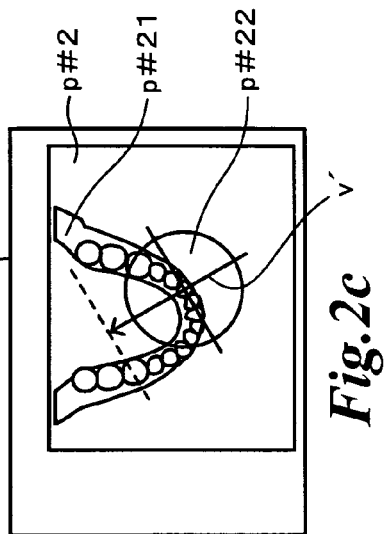
Fig.2b
Fig.2c
Fig.2a

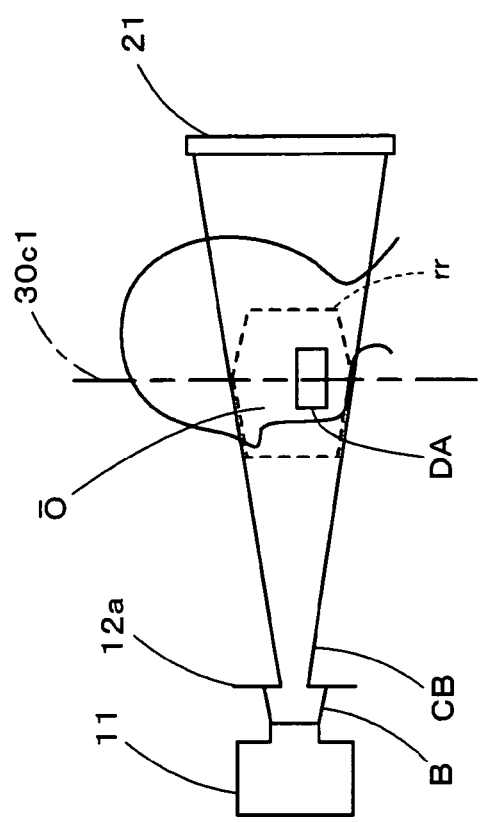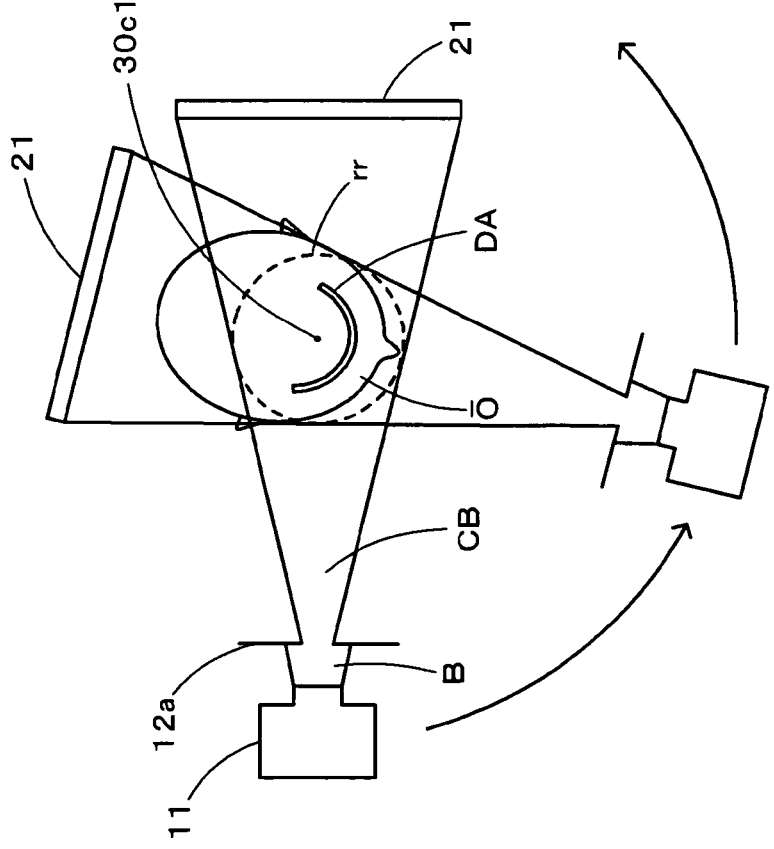
Fig.4Ab
Fig.4Aa

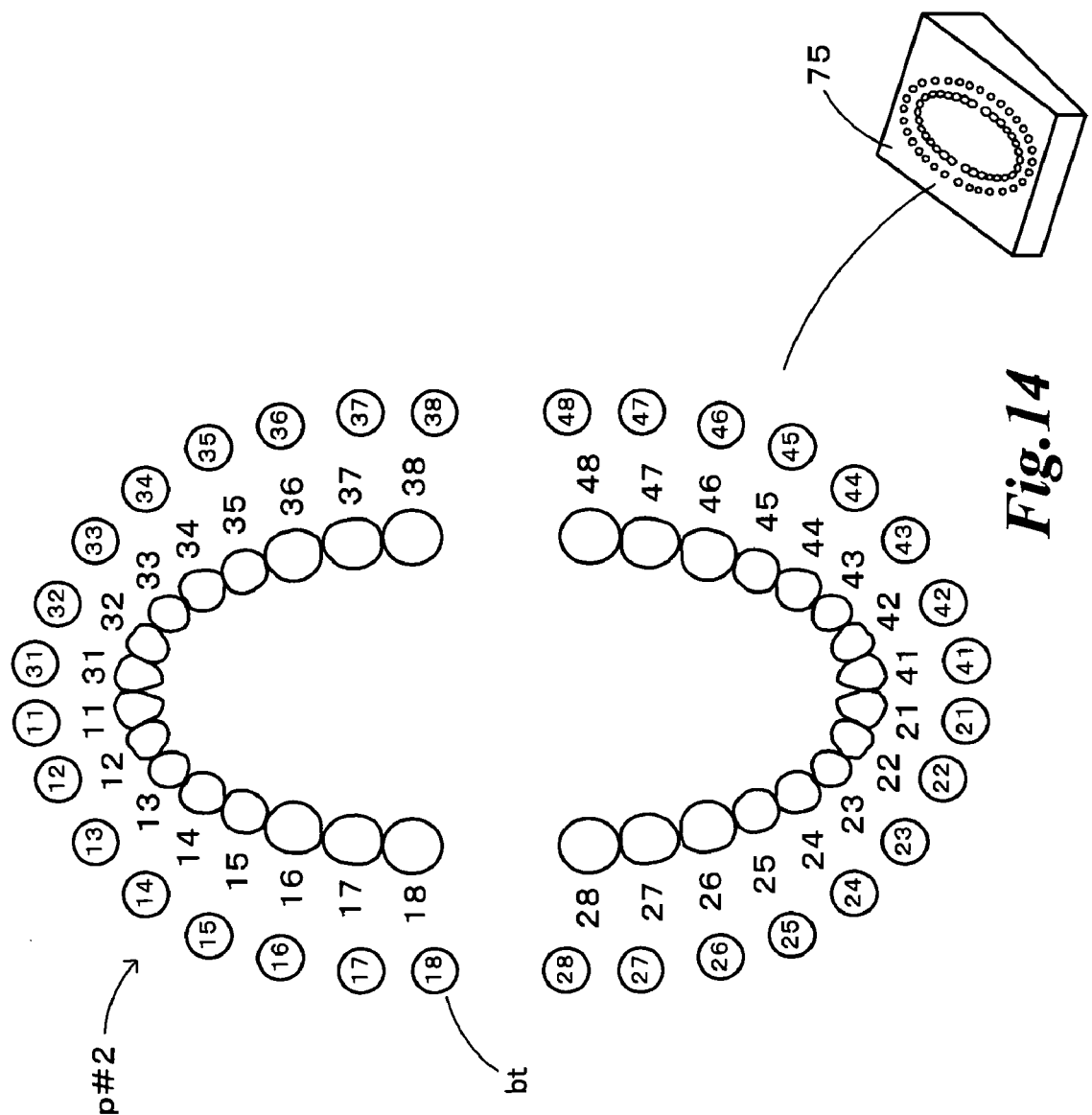

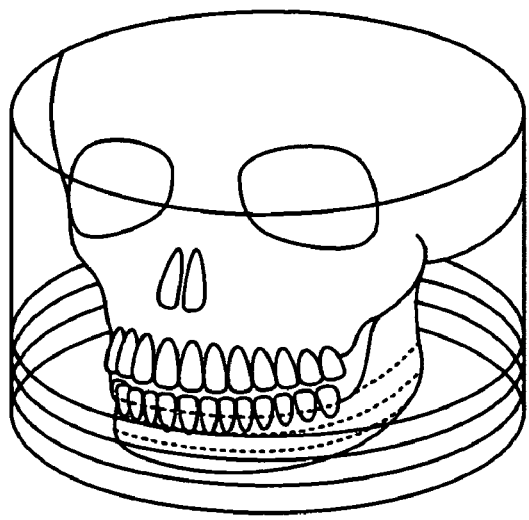
*Fig.16a*
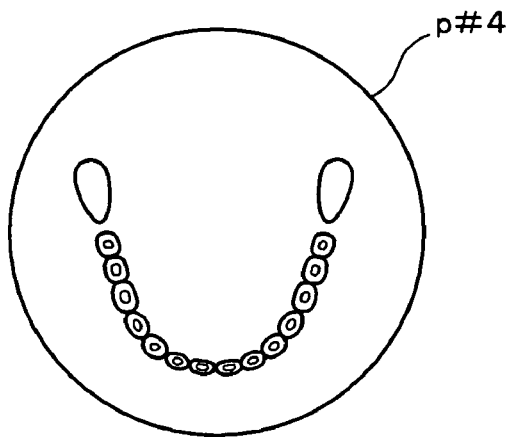
*Fig.16b*
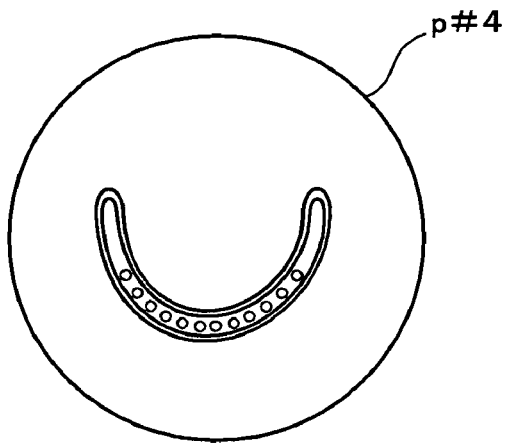 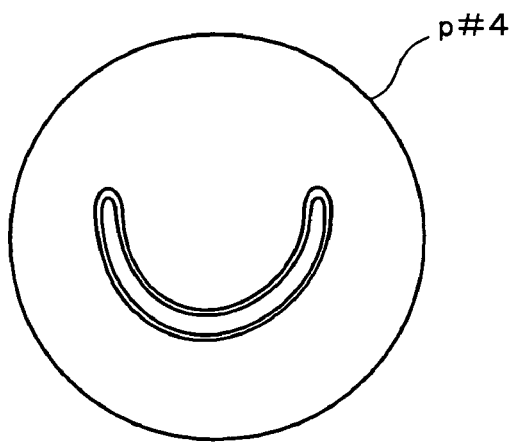
*Fig.16c*  *Fig.16d*

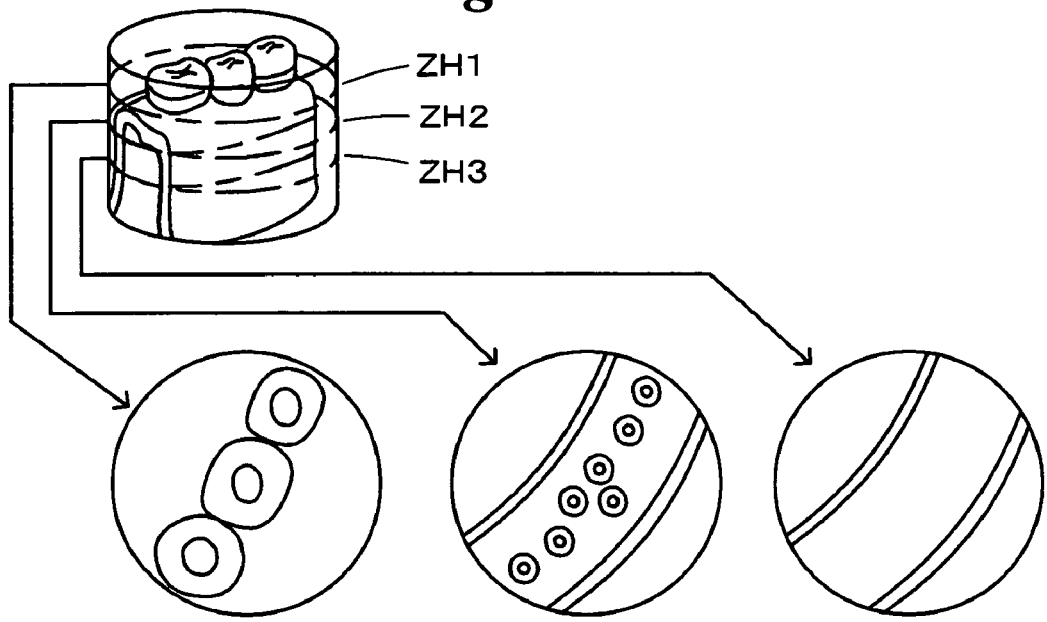
*Fig.21a*
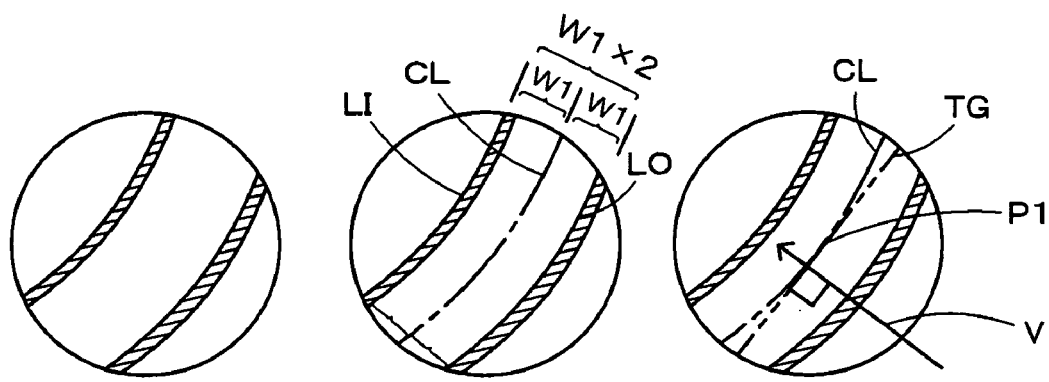
*Fig.21b*  *Fig.21c*  *Fig.21d*

DISPLAY METHOD OF X-RAY CT IMAGE OF MAXILLOFACIAL AREA, X-RAY CT APPARATUS AND X-RAY IMAGE DISPLAY APPARATUS

FIELD OF THE INVENTION

The present invention relates to a sectional image display method, a display apparatus and a radiography apparatus wherein an X-ray computer tomography is executed for an object to be examined and a CT image of a desired interested area of the object is produced from the obtained CT data.

PRIOR ART

When a CT image of an area to be radiographed is produced from the CT data of a radiographed object, an optional slice plane may be settable in principle. However, it has been troublesome operation that a slice plane is set in a desirable direction relative to the interested area to be observed which is a part of the area to be radiographed and such operations have required much time.

Similar prior art aiming to solve the problem is JP-A-2002-11000 which discloses a method in which CT images in a plurality of directions are cut out and prepared in advance from the three-dimensional data of a reconstructed area to be radiographed, a plurality of CT images of which slice planes are orthogonal each other are displayed in an array, and a cursor is moved on the displayed CT image to make the CT image of the slice plane corresponding to the cursor sequentially changed and displayed.

Further JP-A-8-215192 discloses an image diagnosis apparatus in which a panoramic image and an axial sectional plane (parallel to a Z-plane) of a dental arch are simultaneously displayed on one screen, and an oblique sectional plane corresponding to an oblique line is shown when the oblique line is selected with respect to the axial sectional plane.

[Patent Document 1] JP-A-2002-11000

[Patent Document 2] JP-A-H08-215192

However, according to the method of JP-A-2002-11000, it has a problem that the slice plane of the obtained CT image is different from the view which is familiar with a dentist and the position and direction of the region are hardly understood at once. Further according to the apparatus of JP-A-8-215192, it is required that an axial sectional plane is once displayed and the oblique line is selected relative to the image of the sectional plane, thereby causing troublesome task.

SUMMARY OF THE INVENTION

The present invention has been proposed in order to solve the above-mentioned problems and provides a method and an apparatus for displaying a CT image similar to a panoramic image which is familiar with a dentist.

As the first aspect of the present invention, according to a display method for an X-ray CT image of a maxillofacial area of an object to be examined which is obtained from an X-ray computer tomography, for use in an X-ray CT apparatus or an X-ray CT image display apparatus, the method comprising the steps of: designating an interested area with respect to the maxillofacial area of the object, producing by means of an image processing means a standard observational X-ray CT image of the designated interested area, based on a dental arch reference information prepared in advance for producing the standard observational X-ray CT image, the standard observational X-ray CT image of the designated interested area being an X-ray CT image seen in a direction substantially normal to a curve of a dental arch of the object through its cheek side to its tongue side, and displaying on a display means the standard observational X-ray CT image of the interested area thus produced.

The dental arch reference information includes a dental arch model which mathematically expresses the shape of the entire dental arch or a part thereof in the filed of anatomicus and a data table (look-up table) registering the standard observational direction "v" in advance with respect to the positional information of the entire or a part of the dental arc of the interested area. Such a dental arch reference information may be prepared in advance, may be produced by processing the radiographed image data of the dental arch, or may be produced by actually measuring the shape of the dental arch.

Further according to the second aspect of the present invention, in the first invention, the image data of the maxillofacial area of the object is obtained from an X-ray computer tomography for an entire jaw of the object.

Further according to the third aspect of the present invention, in the first and second aspects, the method further comprises a step of producing a sectional image of an X-sectional plane, a Y-sectional plane and a Z-sectional plane, which are orthogonal each other and produced from a three-dimensional CT data of the object produced by reconstructing image data of the X-ray computer tomography, and in the step of designating the interested area, at least one of the X-sectional plane, the Y-sectional plane and the Z-sectional plane thus produced is displayed to designate the interested area thereon.

Further according to the fourth aspect of the present invention, in the fist and second aspects, the method further comprises a step of displaying selectively some of X-ray transmitted images of the object in different angles obtained from the X-ray computer tomography, and in the step of designating the interested area, the interested area is designated on the X-ray transmitted images thus selectively displayed.

Further according to the fifth aspect of the present invention, in the first aspect, the image data of the maxillofacial area of the object is obtained from a local X-ray computer tomography for a part of jaw of the object.

Further according to the sixth aspect of the present invention, in the fist and second aspects, the method further comprises a step of producing a panoramic image from an X-ray panoramic radiography for the object executed in addition to the X-ray computer tomography, and in the step of designating the interested area, the X-ray panoramic image is displayed to designate the interested area thereon.

Further according to the seventh aspect of the present invention, in the first and second aspects, the method further comprises a step of producing a panoramic image by combining partial data of a plurality of X-ray transmitted image data of the object in different angles, the X-ray transmitted images being obtained when the X-ray computer tomography is executed, and in the step of designating the interested area, the panoramic image is displayed to designate the interested area thereon.

Further according to the eighth aspect of the present invention, in the first and second aspects, in the step of designating the interested area, an illustration image data is displayed to designate the interested area thereon.

Further according to the ninth aspect of the present invention, in the first through eighth aspects, the standard observational X-ray CT image is displayed as at least one of an X-ray CT sectional image and a three-dimensional CT volume image.

Further according to the tenth aspect of the present invention, in the first aspect, the standard observational X-ray CT image is a cross-sectional image of a plane tangential to a curve of the dental arch.

Further as the eleventh aspect of the present invention, according to an X-ray CT apparatus for displaying an X-ray CT image of a maxillofacial area of an object to be examined, having an X-ray generator, an X-ray detector, a moving means for relatively moving the X-ray generator and the X-ray detector relative to the maxillofacial area of the object, and an object holding means on which the object is set up, the apparatus comprising: a designation means of interested area for designating the interested area on the maxillofacial area with respect to the object; an image processing means for producing a standard observational X-ray CT image of the designated interested area, based on a dental arch reference information prepared in advance for producing the standard observational X-ray CT image, the standard observational X-ray CT image of the designated interested area being an X-ray CT image seen in a direction substantially normal to a curve of a dental arch of the object through its cheek side to its tongue side; and a display means for displaying the standard observational X-ray CT image of the interested area thus produced.

Further according to the twelfth aspect of the present invention, in the eleventh aspect, the X-ray computer tomography is executed for an entire jaw of the object by driving the moving means.

Further according to the thirteenth aspect of the present invention, in the eleventh and twelfth aspects, the image processing means produces to display a sectional image of an X-sectional plane, a Y-sectional plane and a Z-sectional plane, each of images being orthogonal each other, which are produced from a three-dimensional CT data of the object produced by reconstructing image data of the X-ray computer tomography; and the designation means of interested area receives operation for designation of the interested area on at least one of the X-sectional plane, the Y-sectional plane and the Z-sectional plane thus produced.

Further according to the fourteenth aspect of the present invention, in the eleventh and twelfth aspect, the display means selectively displays some of X-ray transmitted images of the object in different angles obtained from the X-ray computer tomography, and the designation means receives operation for designation of the interested area on the X-ray transmitted images thus displayed.

Further according to the fifteenth aspect of the present invention, in the eleventh aspect, the X-ray computer tomography is executed for a part of jaw of the object by driving the moving means.

Further according to the sixteenth aspect of the present invention, in the eleventh and twelfth aspect, X-ray panoramic radiography is executed in addition to the X-ray computer tomography by driving the moving means, and the image processing means produces a panoramic image and the designation means displays the panoramic image thus produced to receive an operation for designation of the interested area thereon.

Further according to the seventeenth aspect of the present invention, in the eleventh and twelfth aspect, the image processing means produces a panoramic image by combining partial data of the plurality of X-ray transmitted image data of the object in different angles, the X-ray transmitted images being obtained by executing the X-ray computer tomography, and the interested area designation means receives operation for designation of the interested area on the panoramic image.

Further according to the eighteenth aspect of the present invention, in the eleventh and twelfth aspects, the apparatus further comprises an illustration display means for displaying an illustration of the shape of the dental arch with respect to the object, prepared in advance, and the designation means receives operation for designation of the interested area on the illustration.

Further according to the nineteenth aspect of the present invention, in the eleventh to eighteenth aspects, the standard observational X-ray CT image is displayed as at least one of an X-ray CT sectional image and a three-dimensional CT volume image.

Further according to the twelfth aspect of the present invention, in the eleventh aspect, the standard observational X-ray CT image is a cross-sectional image of a plane tangential to a curve of the dental arch.

Further as the twenty-first aspect of the present invention, according to an X-ray CT image display apparatus for displaying a standard observational X-ray CT image from a maxillofacial area image of an object to be examined obtained by an X-ray computer tomography, the display apparatus comprising; designation means of interested area for designating the interested area on the maxillofacial area with respect to the object; an image processing means for producing a standard observational X-ray CT image of the designated interested area, based on a dental arch reference information prepared in advance for producing the standard observational X-ray CT image, the standard observational X-ray CT image of the designated interested area being an X-ray CT image seen in a direction substantially normal to a curve of a dental arch of the object through its cheek side to its tongue side; and a display means for displaying the standard observational X-ray CT image of the interested area thus produced.

Further according to the twenty-second aspect of the present invention, in the twenty-first aspects, the standard observational X-ray CT image is a cross-sectional image of a plane tangential to a curve of the dental arch.

The X-ray CT apparatus may be designed to receive the projection data stored in a portable storage medium to execute the similar display method.

According to the present invention, when the interested area is designated with respect to an object to be examined, the image processing means produces and displays a standard observational X-ray CT image of the interested area based on a dental arch reference information prepared in advance. According to such a standard observational X-ray CT image, the view direction of the interested area is similar to that of a panoramic image which is familiar with a dentist, so that he can intuitively understand where the interested area exists in a dental maxillofacial area.

Further, when an X-ray CT sectional image is shown as a standard observational X-ray CT image, a plurality of sectional planes of teeth are shown on the image, thereby further facilitating his understanding. Whereas, when a three-dimensional CT volume image is shown as a standard observational X-ray CT image, the interested area is displayed in a manner its front view faces the operator, thereby eliminating to find out it in the maxillofacial area of the object.

Still further, when the X-ray CT image display apparatus is designed to receive the projection data stored in a portable storage medium, collaborate work with the X-ray CT apparatus if it is located in a remote locations, may be available, and such X-ray CT image display apparatus may apply to flexible use.

BRIEF DESCRIPTION OF THE DRAWINGS

FIG. 2b is a side view more specifically showing an X-ray CT apparatus and FIG. 2c shows a display sample of an operation panel.

FIG. 2A shows an external view showing another specified embodiment of an X-ray CT apparatus.

FIG. 4Aa is a plan view and FIG. 4Ab is an elevation view explaining how a broad computer tomography is executed for a maxillofacial area.

FIG. 14 is other example of an illustration showing a dental arch.

FIG. 16a to FIG. 16d are explanatory views showing the principle of an image analysis.

FIG. 21a to FIG. 21d are explanatory views showing the principle of an image analysis.

DETAILED DESCRIPTION OF THE INVENTION

Figure 1:
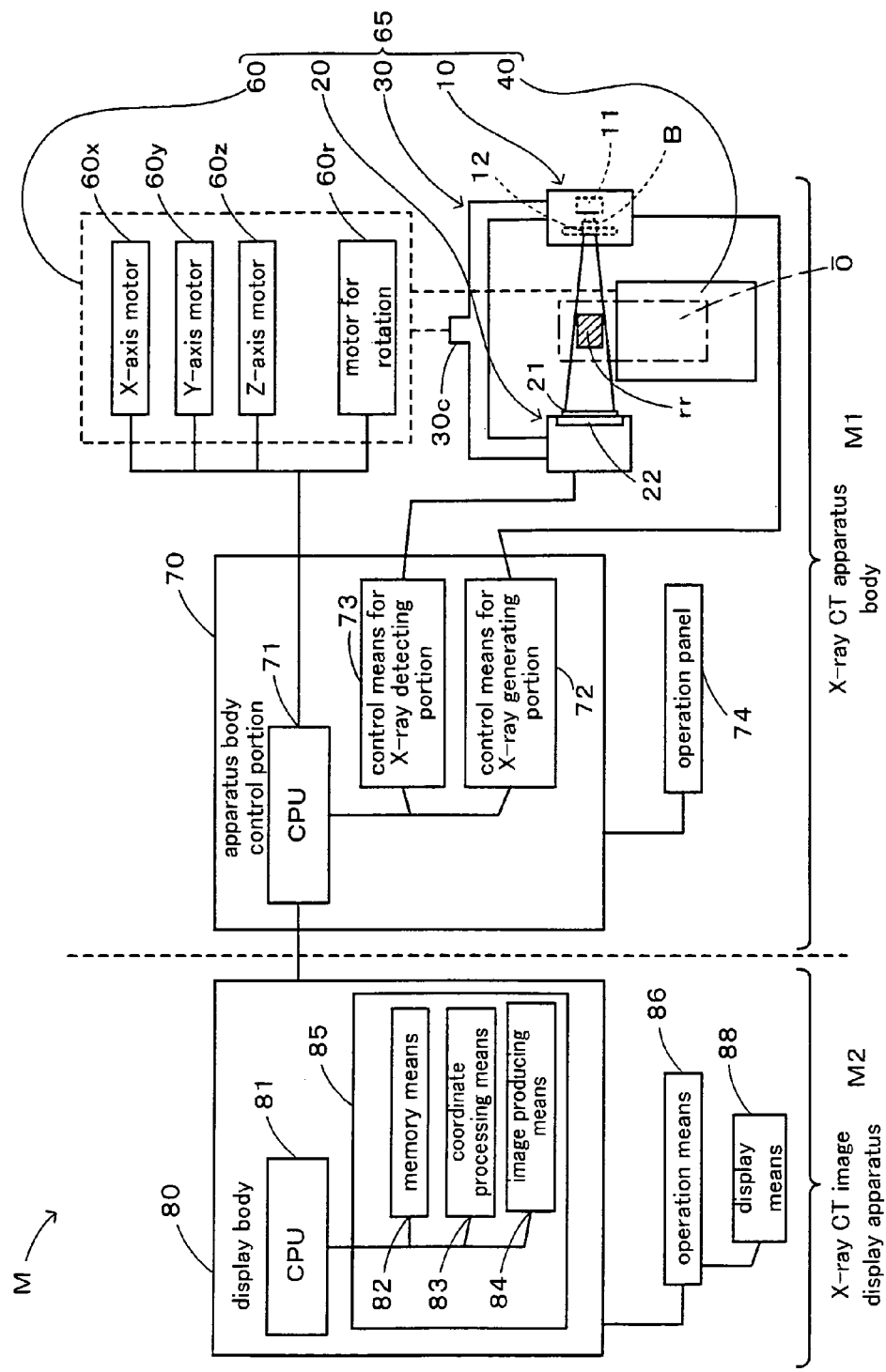
FIG. 1 is a block diagram showing a basic structure of an X-ray CT apparatus of the present invention.

Now, the embodiments of the present invention are explained referring to the drawings.

The embodiment of an X-ray CT apparatus for executing an X-ray computer tomography of a maxillofacial area of a patient is explained.

FIG. 1 is a block diagram showing a basic structure of an X-ray CT apparatus M. The X-ray CT apparatus M has an X-ray CT apparatus body M1 and an X-ray CT image display apparatus M2 and is designed to send and receive data via a communication cable.

The X-ray CT apparatus body M1 has a support means 30 for supporting an X-ray generating portion 10 and an X-ray detecting portion 20 facing each other, an object holding means 40 for holding a maxillofacial area being an object to be examined "o", a driving portion 60 for driving the support means 30 or the object holding means 40, and a main body control portion 70, to which an operation panel 74 is attached. The operation panel 74 may be used for designating an interested area "r" as mentioned later. In such a case, it may be functioned as an illustration display portion for showing an illustration p#2 of the shape of a dental arch DA as shown in FIG. 2c.

When the illustration is used as a scout image in the present invention, the operation panel 74, the display means 88, and the display means 88' as mentioned above function as an illustration display means.

The X-ray generating portion 10 includes an X-ray generator 11 comprised of an X-ray tube for irradiating X-rays and an irradiation field control means 12 comprised of a slit for regulating the field of X-ray beams B. The X-ray detecting portion 20 comprises a cassette 22 provided with an X-ray detector 21 such as a CCD sensor which expands two-dimensionally. The cassette 22 is detachable to the X-ray detecting portion 20, however, the X-ray detector 21 may be fixedly provided for the X-ray detecting portion 20 without the cassette 22. The driving portion 60 has an X-axis motor 60x and a Y-axis motor 60y for moving horizontally a rotary axis 30c of the support means 30 or the object holding means 40 in a cooperative manner, a Z-axis motor 60z for elevating the support means 30 or the object holding means 40 and a rotary motor 60r for rotating the support means 30. The main body control portion 70 has a CPU 71 for executing a several kinds of control programs including a program for controlling the driving portion 60, an X-ray generating portion control means 72 for controlling the X-ray generating portion 10, and an X-ray detecting portion control means 73 for controlling the X-ray detecting portion 20. The operation panel 74 comprises a compact liquid crystal panel or a plurality of operation buttons. An input means 74' of the operation panel 74 shown in FIG. 2 includes a keyboard, a mouse, a touch pen, and the like other than the operation buttons. The operation panel 74 may be provided with a display means 88' comprised of a display such as a liquid crystal monitor, as mentioned later referring to FIG. 2

For example, the display means 88' may be designed to show information such as characters or images required for operating the X-ray CT apparatus body M1 or to also show the content which is shown on the display 88 of the X-ray CT image display apparatus M2 by connecting with the X-ray CT image display apparatus M2 as mentioned later. Further, a several kinds of commands may be designed to be executed for the X-ray CT apparatus body M1 by means of a pointing operation with a mouse on the characters and images shown on the display 88.

The X-ray generating portion 10, the X-ray detecting portion 20, the supporting means 30, the object holding means 40 and the driving portion 60 function as a moving means 65 for moving the X-ray generator 11 and the X-ray detector 21 relative to the object "o".

The X-ray CT apparatus body M1 selectively executes a panoramic radiography of a dental arch DA, a local computer tomography for an area to be radiographed (objective radiography area) rr including a part of the dental arch DA, not the entire dental arch DA, and a broad computer tomography for the area to be radiographed (objective radiography area) rr including the entire dental arch DA. The apparatus body M1 receives several kinds of commands and coordinate data from the X-ray CT image display M2 and sends the obtained image data to the apparatus M2.

Figure 2A:
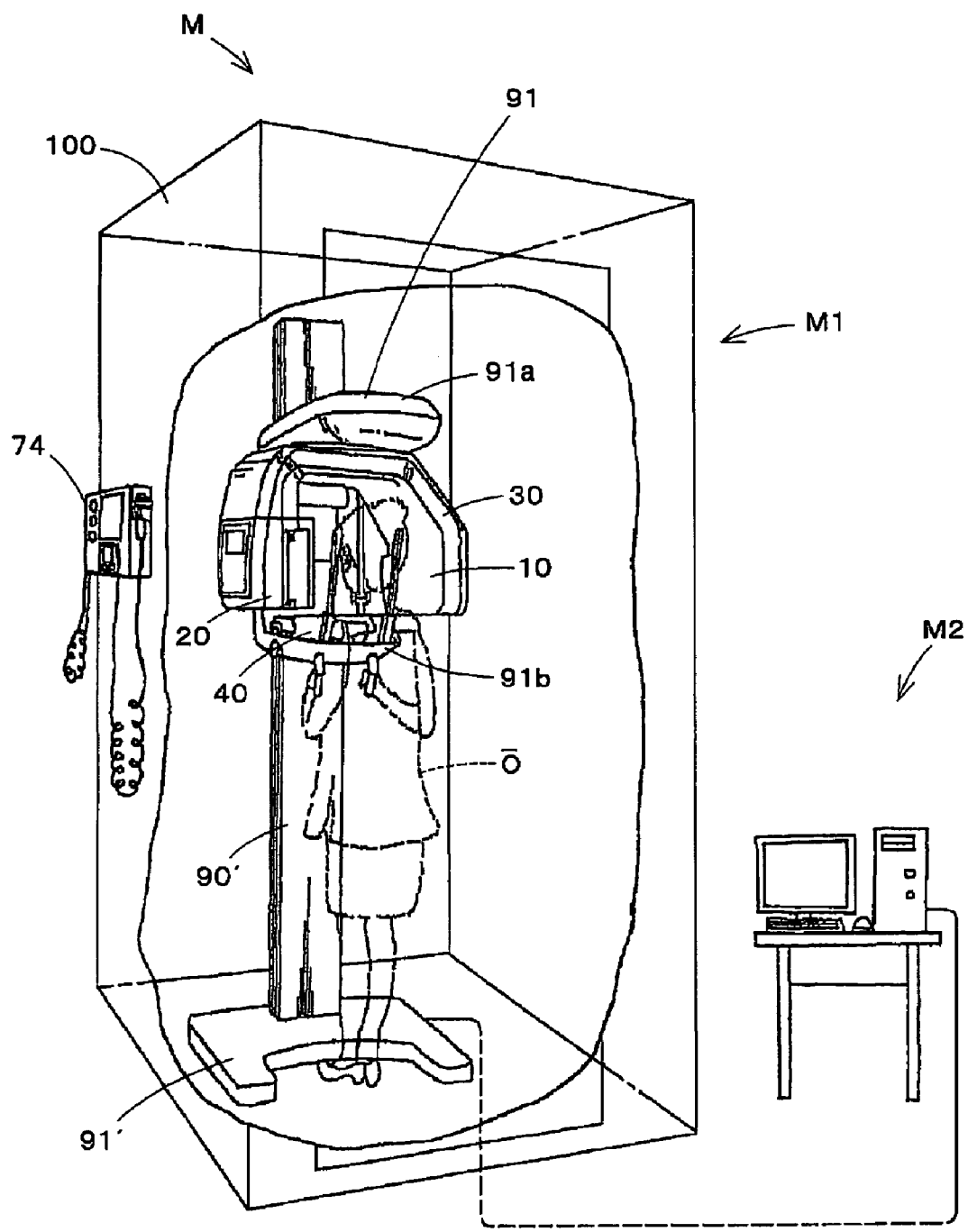
FIG. 2a is a front view.

FIG. 2a and FIG. 2b are a front view and a side view more specifically showing the X-ray CT apparatus M, respectively and FIG. 2c shows a display sample of the display means 88' of the operation panel 74.

The X-ray CT apparatus body M1 shown in FIG. 2a and FIG. 2b has the support means 30 which is constructed as a rotary arm including a rotary motor 60r and supports the X-ray generating portion 10 and the X-ray detecting portion 20 at the both ends thereof so as to be faced each other and the object holding means 40 formed like a sheet having a holder for fixing the head of a human body being an object to be examined "o". The supporting means 30 and the object holding means 40 are displaceably provided for a fixing frame 90 formed like an arch. More specifically, the supporting means 30 is attached to the fixing frame 90 via an elevation frame 91 movable up and down as shown in the vertical arrow in FIG. 2a by means of a chain driving portion 61. The elevation frame 91 includes an XY table 62 for horizontally moving the rotary axis 30c of the supporting means 30 in back and forth and in right and left as shown in the crosswise arrow in FIG. 2a and FIG. 2b. The bottom of the object holding means 40 is supported upwardly by means of an elevation means movable up and down as shown with the vertical arrow in FIG. 2a, and the bottom of the fixing frame 90 includes an XY table 64 for horizontally moving the elevation means 63 in back and forth and in right and left as shown with the crosswise arrow in FIG. 2a and FIG. 2b. A support pillar of the fixing frame 90 is provided with the operation panel 74 including the display means 88' such as a liquid crystal monitor and a compact liquid crystal panel and the input means 74' like a plurality of operation buttons. The driving portion 60 includes the rotary motor 60r, the chain driving portion 61, the X-axis motor 60x and the Y-axis motor 60y of the XY table 62, the elevation means 63, and the X-axis motor 60x and the Y-axis motor 60y of the XY table 64.

FIG. 2A shows another specified embodiment of an X-ray CT apparatus M.

The X-ray CT apparatus body M1 in FIG. 2A has the support means 30 which is constructed as a rotary arm including the rotary motor 60r and supports the X-ray generating portion 10 and the X-ray detecting portion 20 at both ends so as to be faced each other, like the X-ray CT apparatus body M1 shown in FIG. 2a and FIG. 2b.

The elevation frame 91 formed like a letter "c" which projects forward from an upper frame 91a and a lower frame 91b while suspending the support means 30 is provided so as to be movable up and down with respect to a pillar 90' established on a base board 91' by means of an elevation mechanism which is not shown in the figure. The elevation frame 91 includes the XY table 62, not shown, for horizontally moving a rotary axis of the supporting means 30, like the X-ray CT apparatus body M1 in FIG. 2a and FIG. 2b.

The lower frame 91b includes the object holding means 40 having an ear rod for fixing a human head being an object to be examined "o" from side to side and a chin rest for fixing the jaw.

The X-ray CT apparatus body M1 in FIG. 2A is housed in an X-ray shielding room 100 and the operation panel 74 having a compact liquid crystal panel is provided for the outside wall of the room 100 like the X-ray CT apparatus body M1 shown in FIG. 2a and FIG. 2b.

The X-ray CT apparatus body M1 in FIG. 2A has the X-ray CT image display apparatus M2 to send and receive data therebetween via a communication cable like the X-ray CT apparatus body M1 in FIG. 2a.

The moving means 65 of the X-ray apparatus M shown in FIG. 1 can be carried out other than the above-mentioned structure.

The first alternative structure 1: The X-axis motor 60x and the Y-axis motor 60y for horizontally moving the rotary axis 30c of the support means 30, the rotary motor 60r for rotating the support means 30, and the Z-axis motor 60z for elevating the support means 30 are provided, but the driving means for moving the object holding means 40 is not provided.

The second alternative structure 2: The X-axis motor 60x and the Y-axis motor 60y for horizontally moving the rotary axis 30c of the support means 30, the rotary motor 60r for rotating the support means 30, and the Z-axis motor 60z for elevating the object holding means 40 are only provided.

The third alternative structure 3: The rotary motor 60r for rotating the support means 30, the X-axis motor 60x and the Y-axis motor 60y for horizontally moving the object holding means 40, and the Z-axis motor 60z for elevating the object holding means 40 are only provided.

The forth alternative structure 4: The rotary motor 60r for rotating the support means 30, the Z-axis motor 60z for elevating the support means 30, and the X-axis motor 60x and the Y-axis motor 60y for horizontally moving the object holding means 40 are only provided.

The fifth alternative structure 5: The rotary motor 60r for rotating the support means 30 and the Z-axis motor 60z for elevating the support means 30 are provided. One of the X-axis motor 60x and the Y-axis motor 60y is provided for the support means 30 and the other of them is provided for the object holding means 40 so as to horizontally move the X-ray generator 11 and the X-ray detector 21.

The sixth alternative structure 6: The rotary motor 60r for rotating the support means 30 and the Z-axis motor 60z for elevating the object holding means 40 are provided. One of the X-axis motor 60x and the Y-axis motor 60y is provided for the support means 30 and the other of them is provided for the object holding means 40 so as to horizontally move the X-ray generator 11 and the X-ray detector 21.

There may be other various alternative structures by changing the whole parts of the apparatus or partial part of the apparatus. The element for driving the support means 30 and the element for driving the object holding means 40 may be redundant or one of them may be omitted if the X-ray generator 11 and the X-ray detector 21 are moved in the same direction relative to the object "o".

And if both of them are provided, the moving amount can be put together, thereby enabling its relative moving amount to be enlarged or their movement pattern to be varied.

Further if one of them is omitted, thereby enabling its cost and control load to be reduced.

Figure 3:
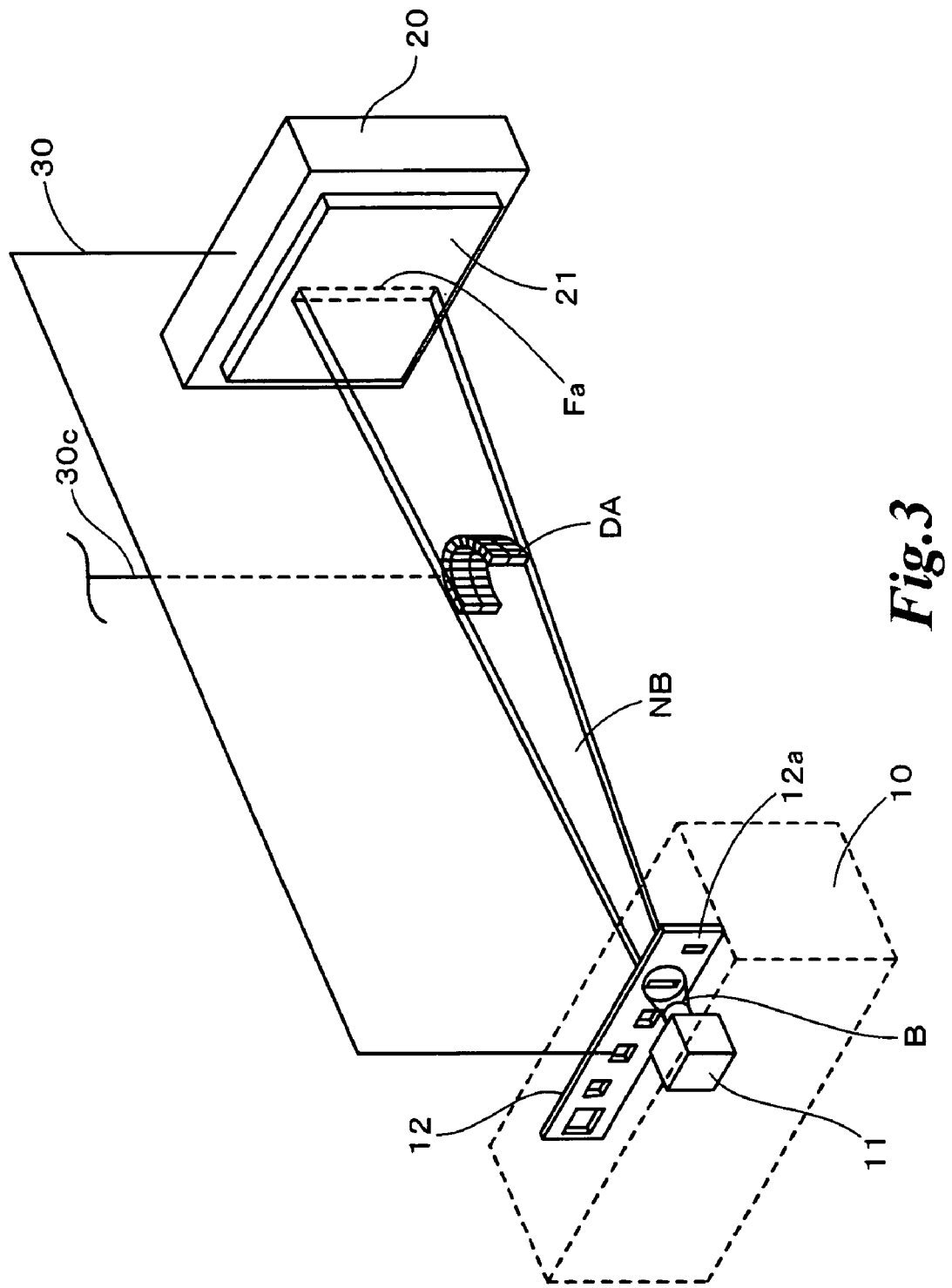
FIG. 3 is an explanatory view showing the structure of a panoramic radiography of a maxillofacial area.

FIG. 3 is an explanatory view showing the principle of a mechanism of a panoramic radiography of a maxillofacial area by means of the X-ray CT apparatus body M1. The irradiation control means 12 provided forward the X-ray generator 11 in the X-ray generating portion 10 is constructed with a slit plate 12a having a plurality of slits with different shape in such a manner that any one of slits is selected by sliding the slit plate 12a right and left and the field of the X-ray beam B irradiated from the X-ray generator 11 is controlled by the selected slit. A narrow slit is selected in case of a panoramic radiography and an X-ray slit beam NB corresponding to the selected slit is irradiated to the X-ray detector 21 of the X-ray detecting portion 20. Then the supporting means 30 is rotated under such condition, the maxillofacial area is scanned by the X-ray slit beam NB, and the transmitted images projected on the area Fa on a detection plane of the X-ray detector 21 are accumulated as panoramic radiography data, thereby executing a panoramic radiography.

Figure 4:
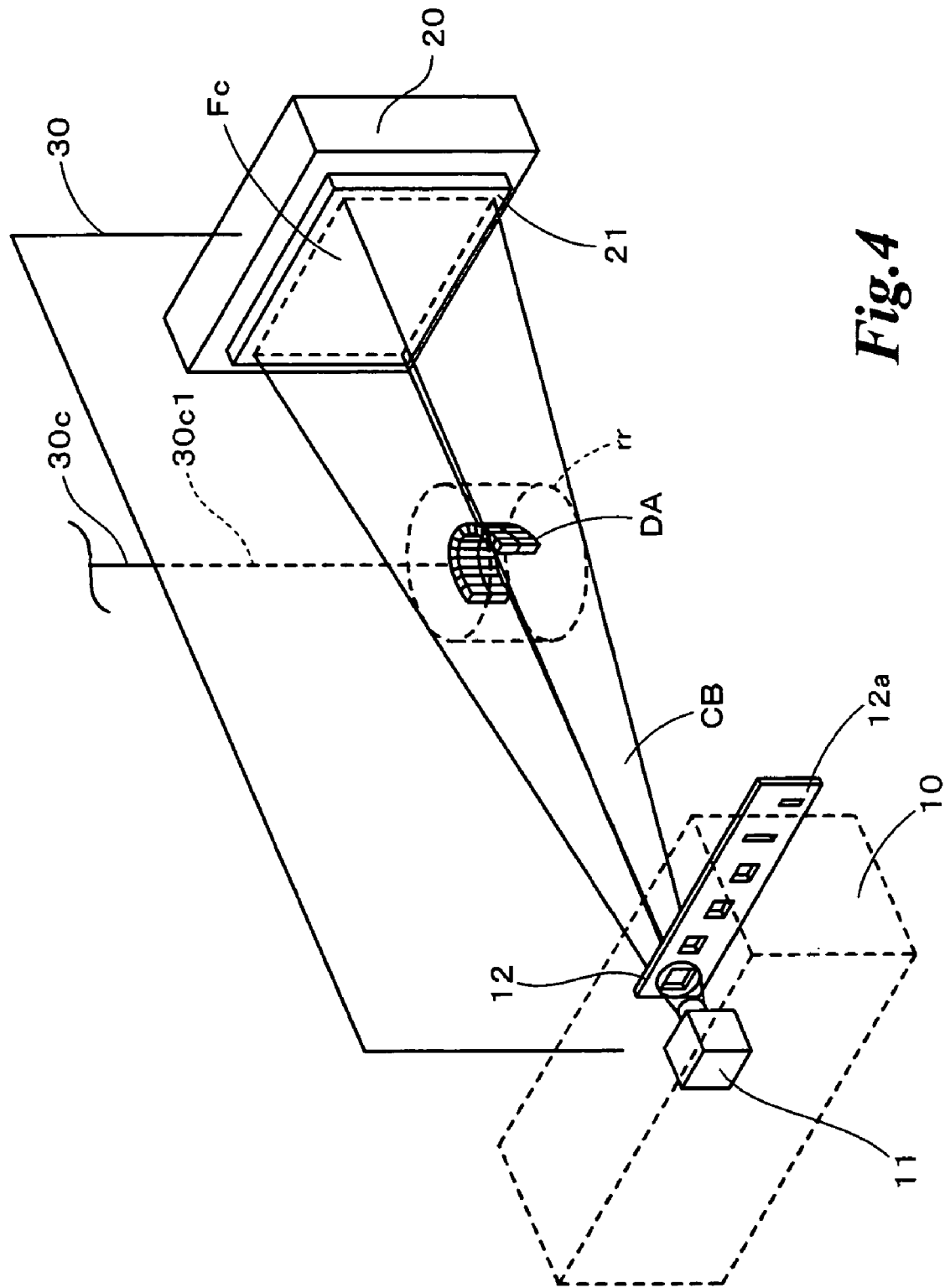
FIG. 4 is an explanatory view showing the structure of a broad computer tomography of a maxillofacial area.

FIG. 4 is an explanatory view showing the principle of a mechanism of a broad computer tomography of a maxillofacial area by means of the X-ray CT apparatus body M1. A rectangular slit is selected from the plurality of slits formed on the slit board 12a in case of a broad computer tomography, a rectangular broad X-ray beam CB according to the shape of the selected slit is irradiated to the X-ray detector 21 of the X-ray detecting portion 20. As shown in FIG. 4Aa and FIG. 4Ab, the area to be radiographed (objective radiography area) rr by the broad X-ray beam CB is the entire jaw, so that the beam CB spreads so as to include the entire-dental arch DA. The supporting means 30 is rotated at least more than a half-turn while fixing the extended line 30cl of the rotary axis 30c of the supporting means 30 inside of the dental arch DA and irradiating the broad X-ray beam CB, and the transmitted image projected on the area Fc of the detection plane of the X-ray detector 21 is accumulated as CT data of the object to be examined "o", thereby executing a broad computer tomography.

FIG. 4Aa is a view when the head of the object "o" during radiography is seen from the top and FIG. 4Ab is a view when the head is seen from the right. The X-ray generator 11 and the X-ray detector 21 rotate around the extended line 30cl of the rotary axis 30c and the X-ray generator 11 rotates in the direction shown with arrows in the figure in the embodiment of FIG. 4Aa. When the supporting means 30 rotates at 360 degrees during computer tomography, the area having a hexagonal section seen from the side which is surrounded with dotted lines in FIG. 4Ab is always irradiated with the broad X-ray beam CB and the area becomes the area to be radiographed (objective radiography area) rr.

Figure 5:
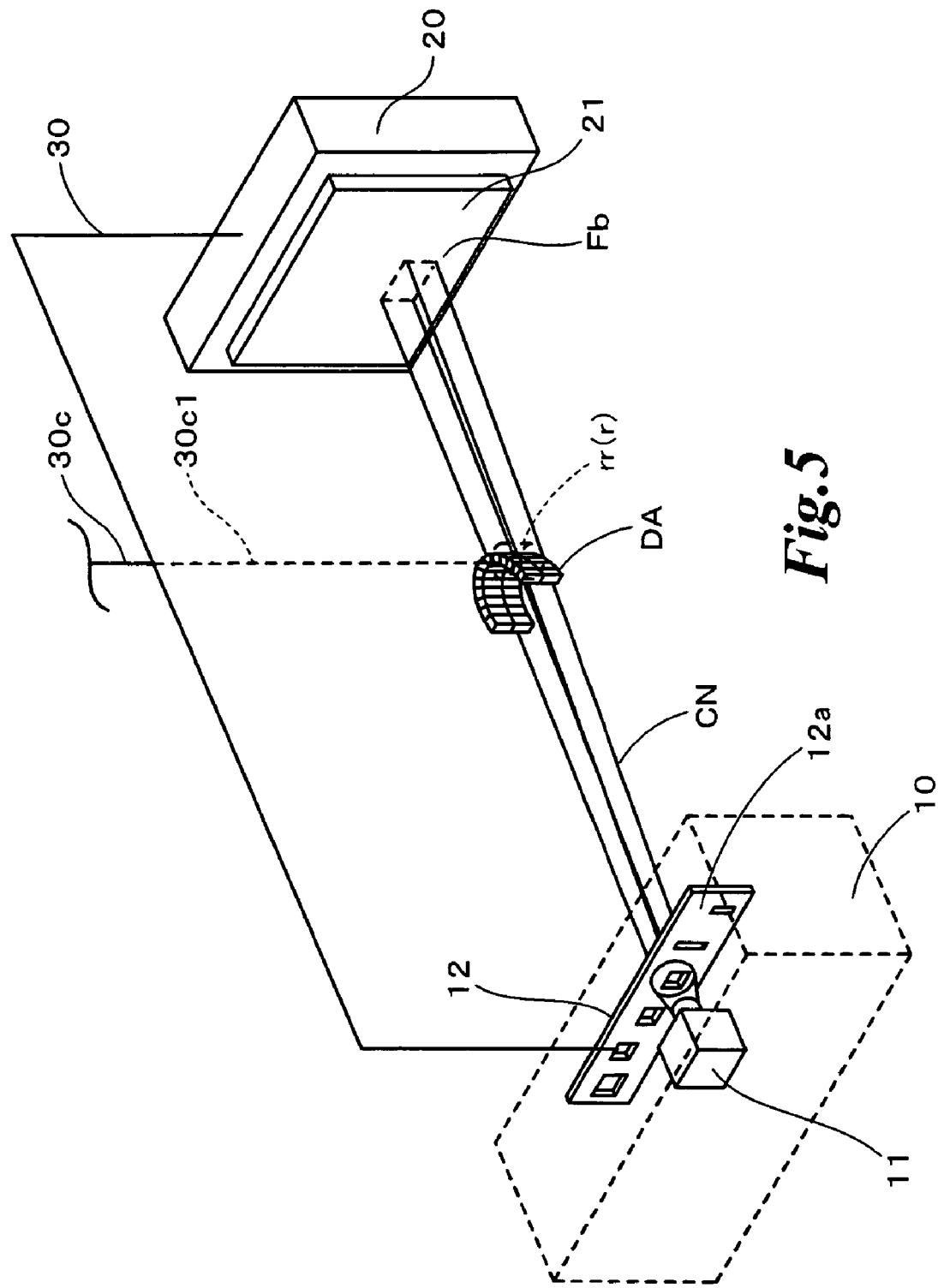
FIG. 5 is an explanatory view showing the principle of a local CT of a maxillofacial area.

FIG. 5 is an explanatory view showing the principle of a mechanism of a local computer tomography of a maxillofacial area by means of the X-ray CT apparatus body M1. A small rectangular slit is selected from the plurality of slits formed on the slit board 12a in case of a local computer tomography, a rectangular local X-ray beam CN corresponding to the selected shape is irradiated to the X-ray detector 21 of the X-ray detecting portion 20. A plurality of small rectangular slits may be provided at various height of the slit board 12a in order to control the height of the local X-ray beam CN. The area to be radiographed (objective radiography area) rr by the local X-ray beam CN is not the entire dental arch DA as the interested area "r", but spreads so as to include the part thereof.

Figure 5A:
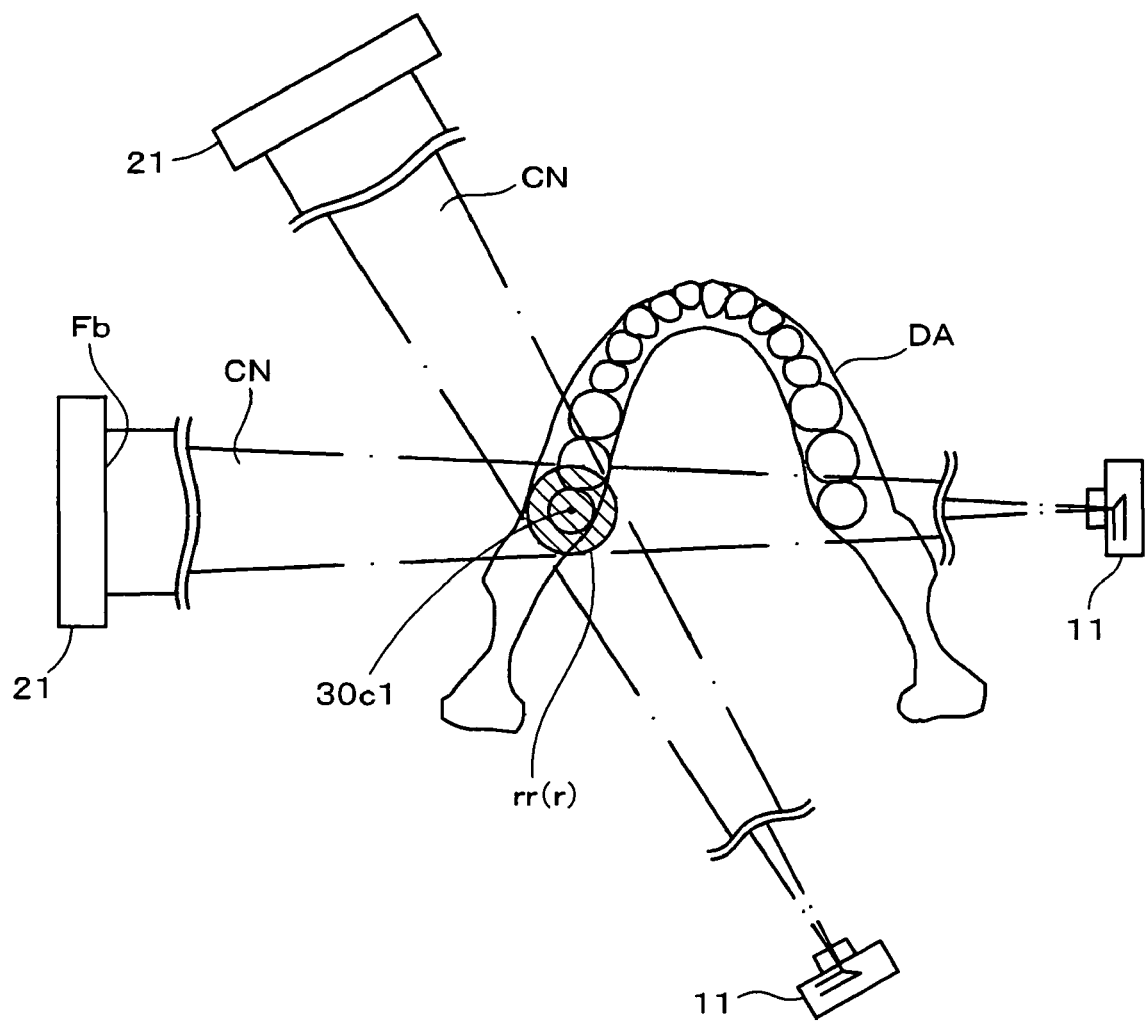
FIG. 5A is a plan view explaining the structure of a local computer tomography of a maxillofacial area.

As shown in FIG. 5A, the supporting means 30 is rotated at least more than a half turn while fixing the extended line 30cl of the rotary axis 30c of the supporting means 30 at the center of the interested area "r" and irradiating the local X-ray beam CN, and the transmitted images projected on an area Fb on an imaging plane of the X-ray detector 21 are accumulated as CT data, thereby executing a local computer tomography.

In either case of the broad computer tomography and the local computer tomography, it is possible to use a method without fixing the rotary axis 30c at the center of the interested area "r" during computer tomography. For example, it is controlled such that the rotary axis 30c is moved by means of the above-mentioned X-Y table 62 but the rotary center of the X-ray generator 11 and the X-ray detector 21 arises other than the rotary axis 30c during computer tomography and the rotary center may be the center of the interested area "r".

Further, a well-known offset scan method may be used in such a manner that the X-ray on the symmetric axis of the field of the X-ray cone beam is designed so as to pass through a position away from the center of the objective radiography area, a part of the objective radiography area is radiographed, and the X-ray radiography data of the entire objective radiography area at more than 180 degrees is obtained.

Namely, it is preferable that the rotary center of the irradiation field of rotating X-ray cone beam goes to the center of the interested area "r".

The X-ray CT image display apparatus M2 is constructed with, for example, a computer and a work station and a display apparatus body 80 has the display means 88 comprised of a display apparatus such as a liquid crystal monitor and an operation means 86 comprised of a keyboard and a mouse. The operation means 86 functions as a means for designating the interested area "r". When it is designed to designate the interested area "r" by adding the operation by the operation means 86 to the image displayed on the screen of the display means 88, the operation means 86 and the display means 88 function as the designation means of interested area. Accordingly, the designation means of interested area includes such a means so as to be used for designating the interested area "r" in any ways. Several kinds of commands can be given by operating a pointer with a mouse on the image and the character on the display means 88. The display means 88 may be a touch panel and in such a case the display means 88 is also served as the operation means 86. The display apparatus body 80 is comprised of a CPU 81 for executing several kinds of programs, a hard disk and so on and has a storage means 82 for storing several kinds of radiography data and images, a coordinate processing means 83 for executing a coordinate calculation, and an image producing means 84. The storage means 82, the coordinate processing means 83 and the image producing means 84 comprise an image processing means 85. The storage means 82 also stores the dental arch reference information, as mentioned later.

The storage means 82 may store the panoramic radiography data obtained by a panoramic radiography, the CT data obtained by a computer tomography, an illustration image data producing an illustration shown as a scout image, a projection image obtained by irradiating a broad X-ray beam from two directions, the dental arch reference information, the produced standard observational X-ray CT image, and so on as mentioned later.

The display means 88 shows images including characters and symbols. The display means 88 displays a scout image showing the dental arch DA as an interested area designating means, receives designation of the interested area "r" on the scout image, and displays the standard observational X-ray CT image (mentioned later) produced from the CT data. The coordinate processing means 83 executes calculation of the coordinate and position of the interested area "r" relative to the coordinate and position of a dental arch model dm in case of a broad CT, and executes calculation of the coordinate and position of the interested area "r" relative to the coordinate and position of the dental arch model dm in case of a local computer tomography. Further, the coordinate processing means 83 executes the coordinate calculation based on the position of the specified interested area "r" for the dental arch model dm in such a manner that the interested area "r" is included in the area to be radiographed (objective radiography area) rr and sends the calculated coordinate data to the X-ray CT apparatus body M1, thereby executing positioning of the object to be examined "o". A scout image may be shown on the display means 88' of the operation panel 74 of the X-ray CT apparatus body M1.

The positioning of the object "o" is executed in such a manner that the rotary center (rotary axis 30c) of the supporting means 30 and the object "o" are arranged at a predetermined position in a space for radiography and the supporting means 30 and the object holding means 40 are moved based on the coordinate data sent from the coordinate processing means 83 so as to include the interested area "r" in the area to be radiographed (objective radiography area) rr. It only requires that the object "o" and the supporting means 30 satisfy a relative positional relation, so that either one of the object holding means 40 or the supporting means 30 may be moved.

The X-ray CT apparatus M is constructed as mentioned above, so that it can execute a display method of X-ray CT image of a maxillofacial area as mentioned below.

The X-ray CT image display means M2 may be connected with a plurality of X-ray CT apparatus bodies M1 as mentioned above in many-to-one relation, or may be designed so as to execute a display method by receiving the radiography data obtained by the other X-ray CT apparatus body M1 which is not connected with a cable via a portable storage medium such as a CD-ROM.

The display method of X-ray CT image of a maxillofacial area according to the present invention is executed in a display apparatus of X-ray CT image by processing the CT data of the object to be examined "o" including a dental arch DA and the X-ray computer tomography is largely divided into a broad computer tomography and a local computer tomography.

The broad computer tomography is for the entire area of a maxillofacial area including the entire dental arch DA. The area shown as a standard observational X-ray CT image of the interested area "r" (hereinafter called as a standard observational X-ray CT image), namely a standard observational objective area, is specified by designating the interested area "r" on the maxillofacial area, and the CT data obtained in advance is rendered to an image process, thereby displaying the standard observational X-ray CT image of the objective area. The interested area "r" may be designated on the displayed images or by designating a tooth th by means of a code without using the images.

On the other hand, the local computer tomography is for locally radiographing a maxillofacial area including a part of the dental arch DA such as an area including a few teeth, not the entire dental arch DA. When the designation of the interested area "r" is received, the radiography conditions are set so as to include the interested area "r" in the actual area to be radiographed (objective radiography area) rr, thereby executing a local X-ray computer tomography. The interested area "r" may be designated on the displayed images, designated by specifying a tooth th by means of a code without using the images, or may be executed visually using a visible light beam being a guide beam for positioning or a graduated scale. Thereafter, the standard observational X-ray CT image of the interested area "r" designated in a normal direction from its cheek to its tongue is produced from the obtained CT data to be displayed.

In either case of the broad computer tomography and the local computer tomography, the standard observational direction "r" of the interested area "r" in a normal direction from its cheek to its tongue can be obtained by the three-dimensional dental arch model dm of the dental arch DA or obtained by referring a data table (look-up table) in which the standard observational direction "v" is registered in advance per the region of the interested area "r", as mentioned later. The dental arch model dm can be defined as a function which mathematically expresses the entire or a part of the dental arch DA. The dental arch model dm may be defined by assuming the shape of a standard dental arch or individually defined by the shape data obtained by image processing the image data of the obtained dental arch. Otherwise it may be individually defined by the data obtained by actually measuring the shape of the dental arch.

According to the present invention, the information on a standard observation such as the dental arch model dm, the coordinate data of the data table based on the dental arch model dm, necessary information for introducing the standard observational direction "v", the standard observational direction "v" itself, and the like is generally called as the dental arch reference information.

Since the dental arch DA is curved, the standard observational direction "v" may be different in each objective region. The dental arch reference information is defined as such an information for seeing a desired objective area from its front. The dental arch reference information is such an information for seeing the objective area from its front so that a specific standard observational direction "v" is not always required and it may be such an information of a slice position which can see the objective area from the front.

In a three-dimensional space in which the X-ray CT apparatus M, more specifically the X-ray CT apparatus body M1 exists, the position where the dental arch model dm is assumed or set can be understood as the coordinate information and the positional information. Also the position in a three-dimensional space of the interested area "r" to be designated can be understood as the coordinate information and the positional information. Therefore, according to the present invention, the standard observational X-ray CT image at the interested area "r" is produced based on the coordinate information and positional information of the dental arch model dm and the coordinate information and positional information of the interested area "r".

The process of obtaining the CT data relating to the object to be examined "o" from the CT data obtained by a broad CT is explained as an example. In this process, the coordinate information and positional information of the dental arch model dm and the coordinate information and positional information of the interested area "r" are understood, so that the coordinate and position of the interested area "r" relative to the coordinate and position of the dental arch model dm can be identified by designating the interested area "r" by the method mentioned later. When the coordinate and position of the interested area "r" relative to the coordinate and position of the dental arch model dm is identified, the standard observational direction "v" and the slice position sl can be set as mentioned later. When the standard observational direction "v" and the slice position sl are set, the CT data are rendered to an image processing and the standard observational X-ray CT image of the interested area "r" can be reconstructed.

Next explained is the process for obtaining the CT data of the object to be examined "o" from the CT data obtained by a local CT. In this process, when the interested area "r" is designated by the method mentioned later, the positioning of the object can be achieved by the mechanical structure of the X-ray CT apparatus body M1 and a local CT is executed for the designated interested area "r" as a radiography object. In this process, the coordinate information and positional information of the dental arch model dm and the coordinate information and positional information of the interested area "r" are understood, so that the coordinate and position of the interested area "r" relative to the coordinate and position of the dental arch model dm can be identified. When the coordinate and position of the interested area "r" relative to the coordinate and position of the dental arch model dm is identified, the standard observational direction "v" and the slice position sl can be set as mentioned later. When the standard observational direction "v" and the slice position sl are set, the CT data are rendered to an image processing and reconstructed to produce the standard observational X-ray CT image of the interested area "r".

Referring to FIG. 23 and FIG. 23A to FIG. 23E, the basic relation of the dental arch model dm and the interested area "r" is detailed. They are plan views explaining a designation method of the interested area "r" according to different embodiments in which the slice plane showing the cross-section of the tooth th constituting the tooth row of a lower jaw is seen from the top, for easy understanding. The generally shaped dental arch DA comprised of a tooth th, a jaw bone jb and a jaw joint jj is diagrammatically shown and the dental arch model dm is set relative to the dental arch DA.

The shape of the dental arch model dm can be varied as mentioned later referring to FIG. 15 and it is curved along the dental arch DA or is at least curved along the dental arch DA. In detail, the dental arch model dm is like a horseshoe or is substantially like a horseshoe cutting across the center of each tooth th of the dental arch DA, for example, and it is the same as or similar to the panoramic section in case of dental panoramic radiography. It is for example assumed or set at a spatial position in the three-dimensional space shown in FIG. 17b, mentioned later. The obtaining method of the dental arch model dm may be varied as mentioned later. The dental arch model dm may be formed based on the generally shaped dental arch DA, obtained by the actually measured value of respective dental arch DA, or obtained by the image analysis, of which detail is explained later.

The dental arch DA is curved being convex into a cheek along the array of the tooth th and is opened outward into the cheek from around the innermost tooth th48 directing to the jaw joint jj as shown in FIG. 23 and FIG. 23A to FIG. 23E.

The dental arch model dm is curved along the shape of the dental arch DA connecting the substantial centers between the tongue side and the cheek side of the dental arch DA. More specifically, the dental arch model dm is comprised of a parabolic curve connecting the center points of a plurality of teeth th of the dental arch and forming convex into the cheek side and a line forming convex into the tongue side from around the innermost tooth th 48 to the jaw joint jj and connecting the center of the tooth th48 and the center of the jaw joint jj, thereby forming a curved shape.

There may of course exist a specially shaped dental arch DA depending on the object. In such a case, the dental arch model dm may be formed depending on such a specially shaped dental arch DA.

As understood from the above description, the present invention may be applicable to a jaw joint jj. The jaw joint jj is an important diagnosis region and may be specifically noticed as a diagnosis object.

The interested area "r" has an outer edge of a perfect circle when seen from the top and is cylindrical in three-dimension by extending the outer edge vertically. The center is referred as rc.

Figure 23:
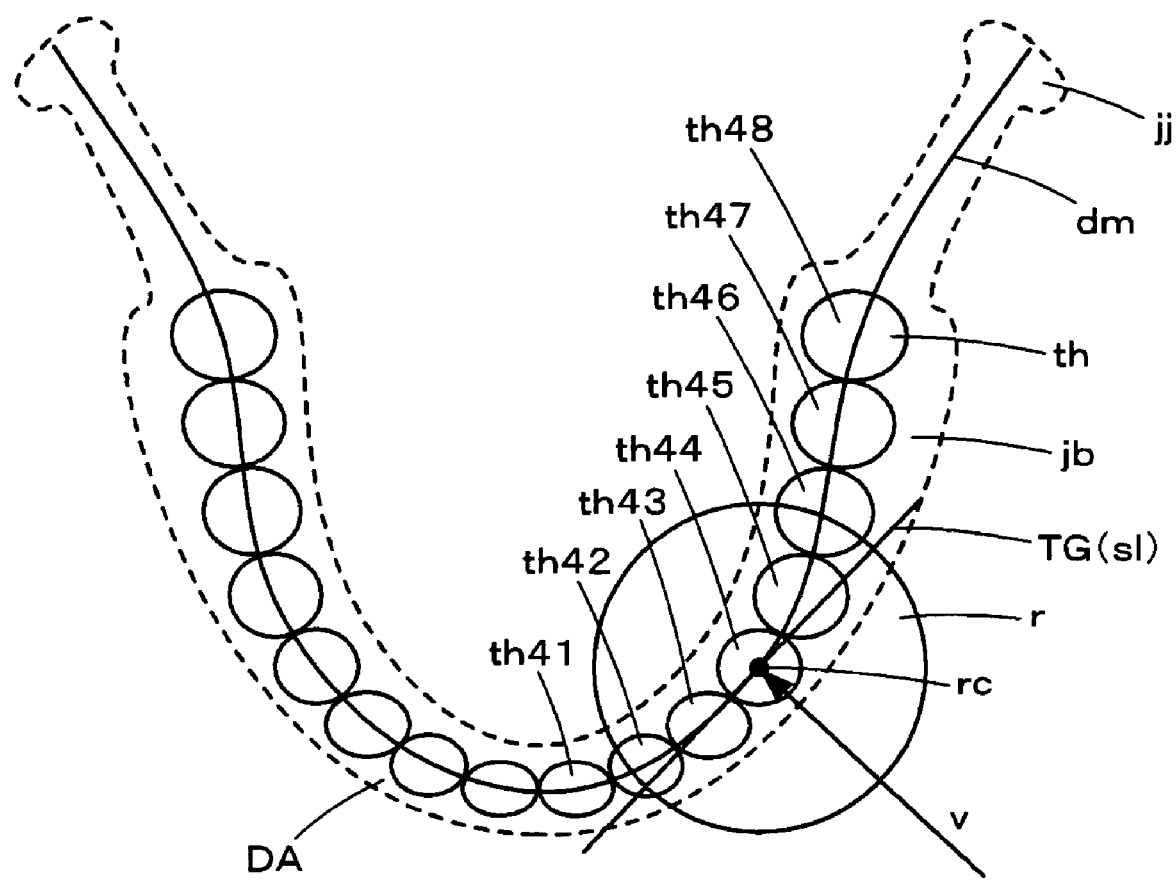
FIG. 23 is a plan view explaining the relation of a dental arch model and an interested area.

In the embodiment of FIG. 23, the tooth th44 is focused and the circular interested area "r" is designated conforming the center rc thereof to the center of the tooth th44 on the line forming the dental arch model dm. In this case, a tangent line TG of the dental arch model dm at the center rc is calculated or set, and the direction in which the dental arch is designated from a normal direction from the cheek to the tongue and which is perpendicular to the tangent line TG can be calculated or set as the standard observational direction "v".

The standard observational direction "v" is basically a normal line direction relative to the curve of the dental arch DA. It is a direction orthogonal to the tangent line TG in the figure, however, it is not necessarily a strict normal direction and it may be almost normal direction. However, it is required to set the standard observational direction "v" so as to give a feeling of viewing the interested area "r" from its front.

Specifically, the allowable range of the angle of the observational direction "v" relative to the tangent line TG is within plus or minus 30 degrees relative to the standard observational direction "v" as shown in FIG. 23, preferably within plus or minus 10 degrees, or more strictly within plus or minus 5 degrees. Namely, when the angle of the standard observational direction "v" to the tangent line TG is 90 degrees, the allowable range is from 60 degrees to 120 degrees, preferably from 80 degrees to 100 degrees, more strictly from 85 degrees to 95 degrees.

If such a standard observational direction "v" is calculated or set, namely it is determined, the CT data is reconstructed to produce an X-ray image seen from the standard observational direction, and a sectional image in which a desired slice position sl seen from the standard observational direction "v" is a sectional plane can be produced or a three-dimensional CT volume image seen from the standard observational direction "v" can be produced. The three-dimensional CT volume image referred in this application is a volume rendering image.

When the standard observational X-ray CT image is produced from the sectional image, the slice plane at each slice position, namely the sectional plane, may be set on an optional curved plane such as a curved plane along the curve of the dental arch DA or on a flat plane.

Figure 23A:
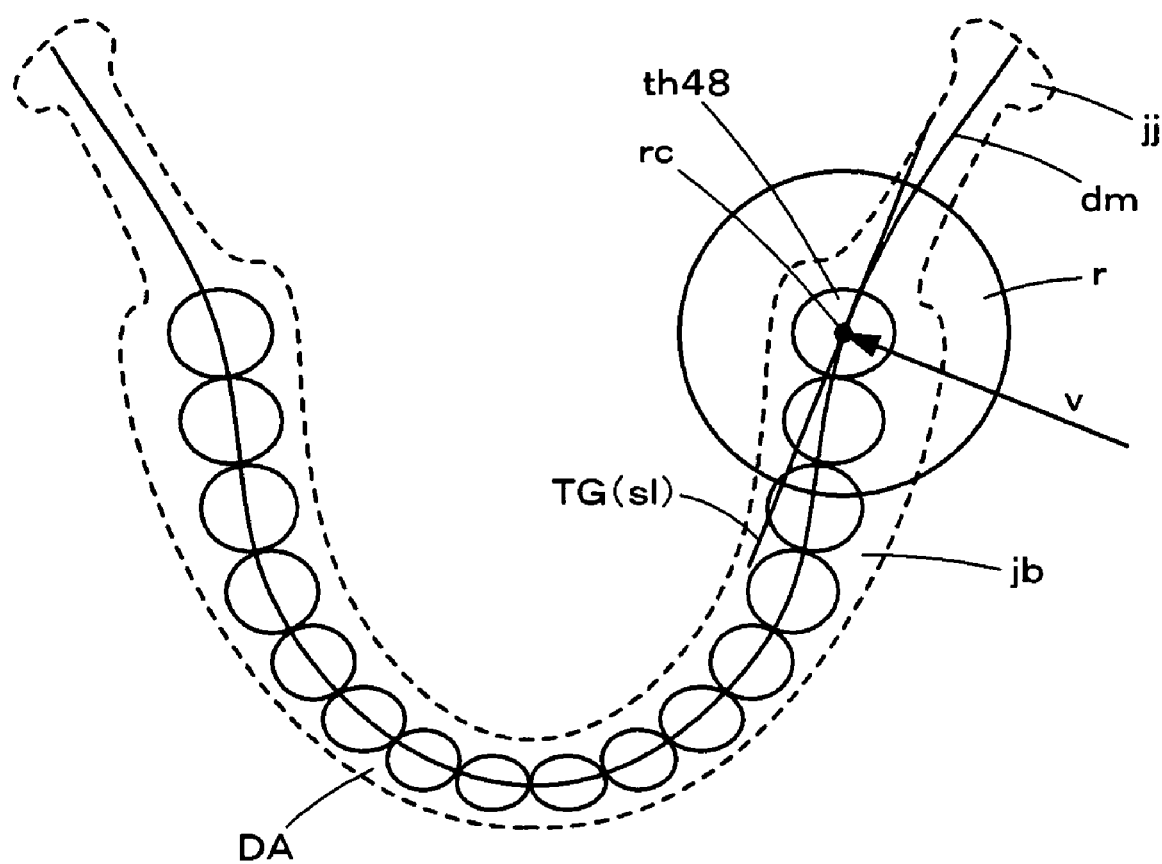
FIG. 23A is other plan view explaining the relation of a dental arch model and an interested area.

In FIG. 23A, the innermost tooth th48 is designated as an interested area "r". In this case, the tangent line of the dental arch model dm is not a line being convex to the cheek side, but a line being convex to the tongue side. However, it is similar to FIG. 23 in that the direction which is perpendicular to the tangent line TG and in which the dental arch is designated in a normal direction from the cheek to the tongue can be calculated or set as the standard observational direction "v".

The term "normal direction through cheek side to tongue side of the dental arch" includes such a case that dental arch is observed from its back side to front side, accordingly the present invention does not exclude such a case.

Also in such a case, the direction means a minus direction from its tongue side to its cheek side. Therefore, a minus vector may be included as a normal direction vector directing through its cheek side to its tongue side.

Figure 23B:
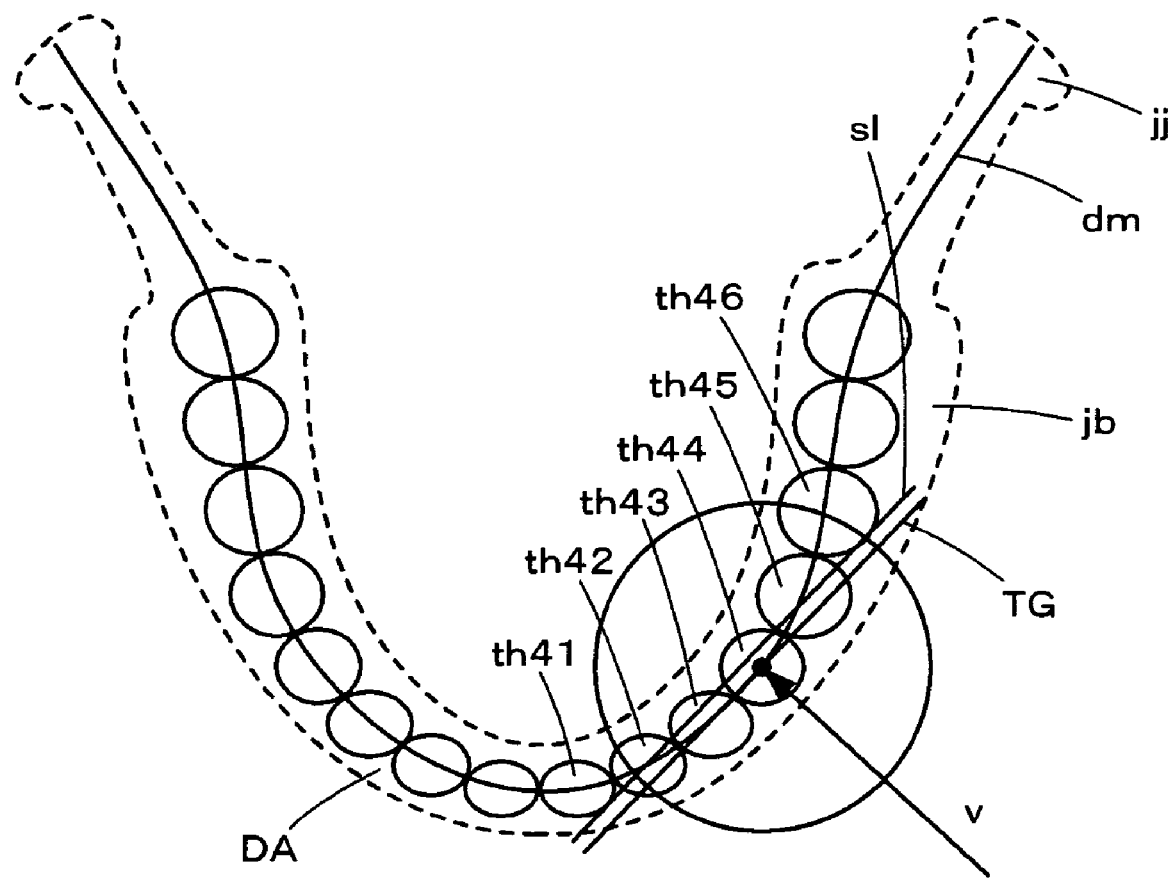
FIG. 23B is other plan view explaining the relation of a dental arch model and an interested area.

When producing a sectional image of the interested area "r" from the standard observational direction "v", the position of a sectional plane, namely the slice position sl, is optional and may be set at the tangent line TG or at the position where the tangent line TG of FIG. 23 is slightly moved in parallel into the tongue as shown in FIG. 23B. It is possible to reconstruct CT data to produce a sectional image developing vertically at the slice position sl by means of an image processing.

When the slice position sl is set at the tangent line TG in FIG. 23, the tooth th to be sliced is only a tooth th42, th43, th45 around the tooth th44 other than the tooth th44. However, if the slice position sl is set at the position shown in FIG. 23B, the teeth th41, th42, th43, th44, th45, and th46 become an object to be sliced, so that the area of teeth th to be sliced can be larger. The slice position sl is preferably set at the position where a plurality of teeth th are shown on the sectional image to be a standard observational X-ray CT image, not the position which is entirely apart from the tooth th.

Figure 23C:
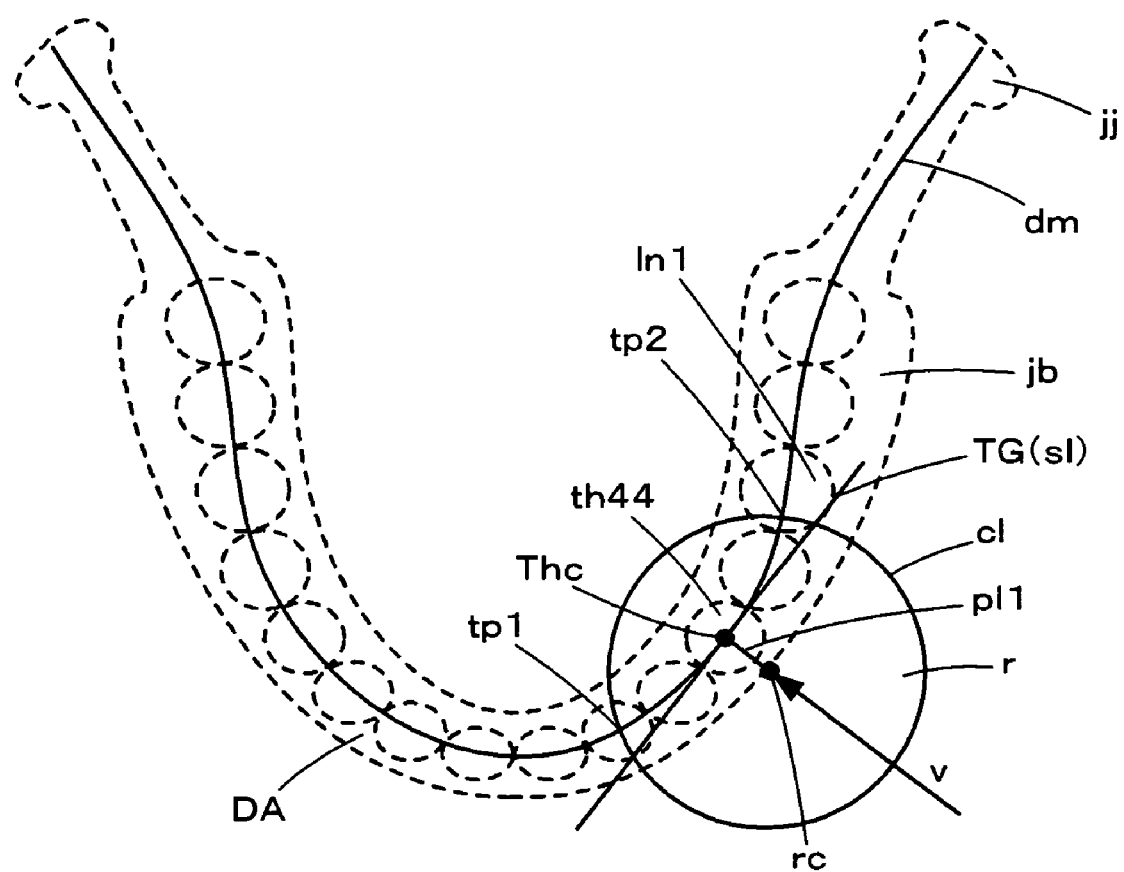
FIG. 23C is other plan view explaining the relation of a dental arch model and an interested area.

In the embodiment of FIG. 23C, a tooth th44 is focused and the center rc of the interested area "r" does not conform to the point Thc at the center of the tooth th44 on the line of the dental arch model dm, but is vaguely specified in such a manner that the interested area "r" includes the tooth th44. In this way, it does not always necessary to designate the interested area "r" so as to accord the center rc of the circular interested area "r" with the center of an objective tooth th. In this case, the tangent line TG to which a foot of a perpendicular pl1 can be drawn downward from the center rc to the dental arch model dm may be calculated and the slice position sl with the tangent line TG as a standard may be set. If a plurality of foot of perpendiculars pl1 may be drawn downward depending on the positional relation of the dental arch model dm and the circle center rc of the interested area "r", it may be dealt appropriately by setting a priority order in advance such as by selecting one closer to the center of the front tooth. In the condition shown in FIG. 23C, the direction of the foot of a perpendicular pl1 and the standard observational direction "v" are accorded.

Figure 23D:
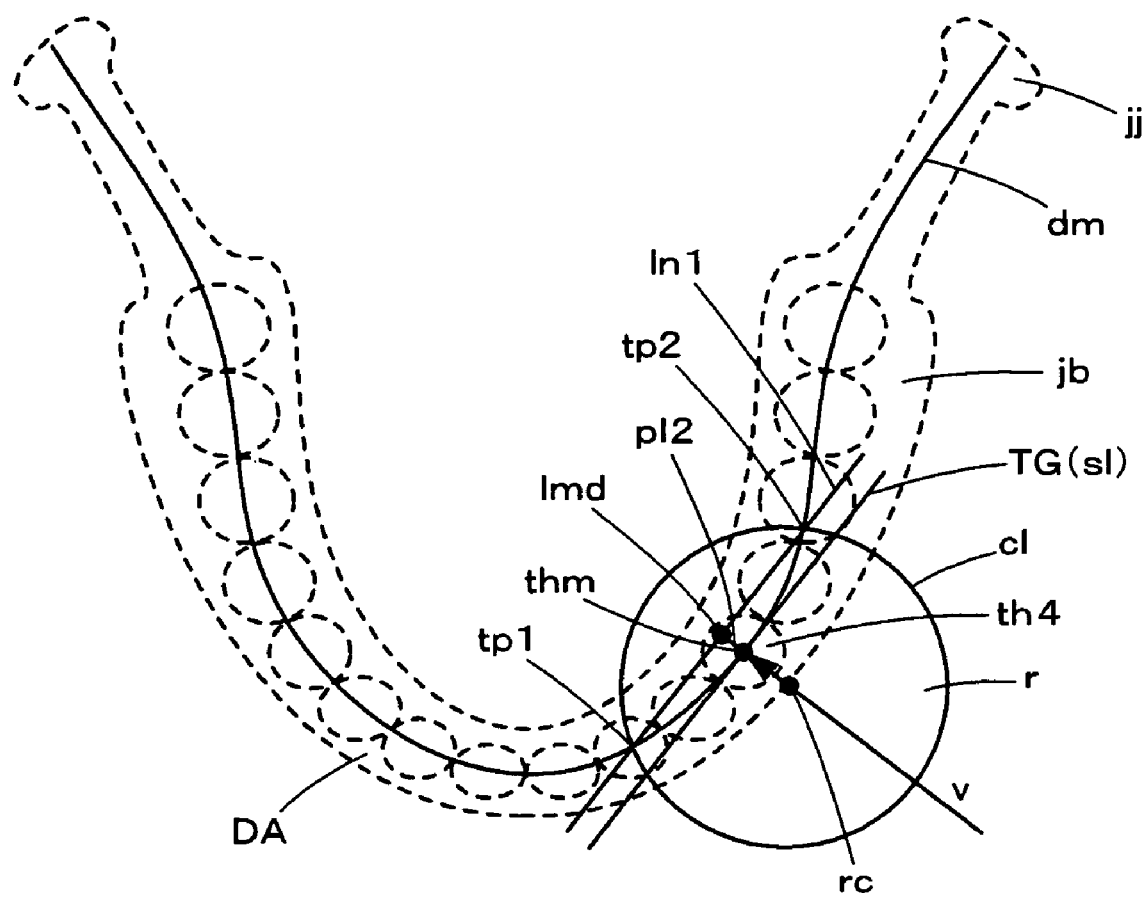
FIG. 23D is other plan view explaining the relation of a dental arch model and an interested area.

In the embodiment of FIG. 23D, an intermediate point lmd between intersecting points tp1, tp2 of a straight line ln1 passing the two intersecting points tp1, tp2 of the outer edge circle cl of the interested area "r" and the dental arch model dm is calculated, a point thm on the dental arch model dm from which a foot of a perpendicular is drawn downward to the intermediate point lmd is obtained, and the tangent line TG at the point thm to the dental arch model dm is calculated or set, thereby setting a slice position sl being the tangent line TG as a reference as mentioned before.

Setting of the slice position sl is optional, so it is not detailed, but there are many other setting methods. Although the shape of the interested area "r" is assumed to be a perfect circle and a cylindrical, a point rc' around the center of the interested area "r" corresponding to the center rc of the circle may be set in the interested area "r". Further, the shape of the interested area "r" includes a dot.

In case of FIG. 23D in which the slice position sl is set based on the line ln1 passing the intersecting points tp1, tp2 of the line cl of the outer edge of the interested area "r" and the dental arch model dm, even if the shape of the interested area "r" is optionally set, it only requires to understand the outer edge line of the interested area "r" and it does not require to provide the center rc of the circle or the point corresponding to the center rc.

Figure 23E:
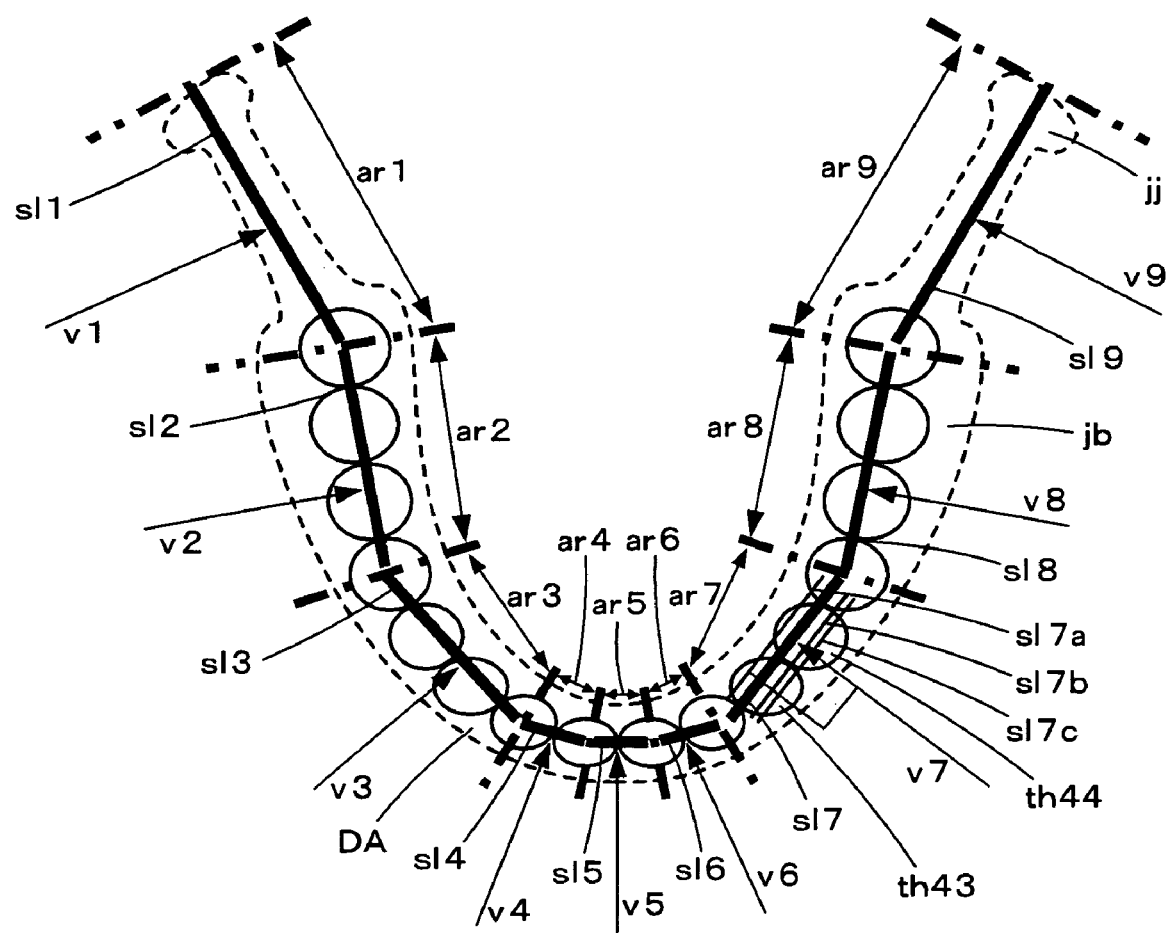
FIG. 23E is still other plan view explaining the relation of a dental arch model and an interested area.

There is a method of obtaining the standard observational direction "v" and the slice position sl without calculating each time. One of them is shown in FIG. 23E in which the area of the dental arch model dm where a plurality of teeth th are arranged along a relatively straight line is focused, and is divided into zones ar1-9 shown with dotted lines and arrows. The standard observational directions v1-9 and the slice positions sl1-9 may be set in advance per zones respectively.

As shown in the embodiment of FIG. 23, the interested area "r" is a perfect circle or cylindrical and is designated by confirming the center rc of the perfect circle or the cylinder with the line forming the dental arch model dm. In this case, if the center rc of the circular interested area "r" is in the zone ar7 of the dental arch model dm, it may be designed to automatically select the standard observational direction v7. Further, it may be constructed to produce a sectional plane sliced at an appropriate position such as slice positions s17a, s17b, s17c which are orthogonal to the standard observational direction v7. Further it may be designed such that the slice position s17 may be automatically selected, not by selecting the standard observational direction "v".

The slice position s17 is not necessarily calculated from the standard observational direction v7. For example, a line connecting one point around the tooth axis of a tooth th43 and one point around the tooth axis of a tooth th44 may be set in the zone ar7, and the slice position sl may be set on the line. The slice position sl may be set at an optional angle, however, it is required to give a feeling of viewing the interested area "r" from the front.

The standard observational direction "v" and the slice position sl may be obtained by calculation per an interested area "r" from the shape of the dental arch model dm based on the three-dimensional shape of the dental arch DA and may be obtained by referring to a data table (look-up table) in which the standard observational direction "v" and the slice position sl are set in advance per the region of the interested area "r".

The straight lines showing the slice positions sl1-9 are shown with short lines in order not to complicate the drawings, however, it does not mean slice processing is executed within the zone ar1-9 shown with the straight lines in the figure. For example, slice at the slice position s17 may be executed other than the zone ar7.

Further, the standard observational direction "v" and the slice position sl may be set per a tooth th, otherwise the dental arch model dm may be comprised of an aggregate of dots and the standard observational direction "v" and the slice position sl may be set per a dot. Still further, the standard observational direction "v" and the slice position sl may be set per a tooth th. The shape of the interested area "r" may include dot, as mentioned above. Namely, the interested area "r" may be designated as a dot not as an area extending two-dimensionally. The image of the sliced section to be produced may be an image of only the area within the interested area "r" or an image including other than the interested area "r".

Next the method of obtaining the standard observational direction "v" is supplementary explained according to the structure of FIG. 23 and FIG. 23A to FIG. 23E.

Figure 15A:
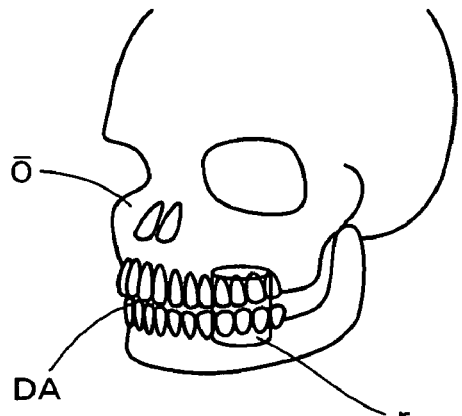
FIG. 15a shows a dental arch and FIG. 15b to FIG. 15e show a specific embodiment of a dental arch model, respectively.
Figure 15B:
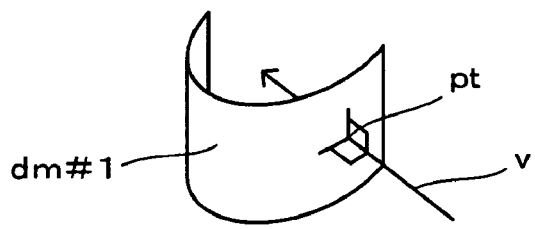
Figure 15C:
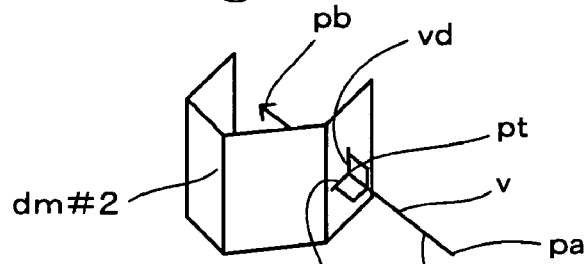

A method of obtaining the standard observational direction "v" using the dental arch model dm is explained. The dental arch model dm is defined as function mathematically expressing the shape of the entire or a part of the dental arch DA. Namely, the shape of the dental arch model dm is function obtained by simplifying the shape of the dental arch DA. As shown in FIG. 15a, the basic shape of the dental arch model dm is formed like a horseshoe-like standard curved plane dm#1 comprising a well-known panoramic section of the dental arch DA or a central layer between the tongue side and the cheek side of the dental arch DA. However, if it is a shape along the dental arch DA, optional shape can be set as the dental arch model dm. For this purpose, the dental arch model dm may be a standard curved plane dm#1 having a horseshoe-shaped curvature like the dental arch DA as shown in FIG. 15b, or may be a standard composite plane dm#2 formed by rendering mountain fold at plural points of the flat plane as shown in FIG. 15c. The standard curved plane dm#1 and the standard composite plane dm#21 may be a thin layer or may be a thick layer.

When the dental arch model dm is considered to be such a plane, the standard observational direction "v" can set as a direction orthogonal to the plane of the dental arch model dm therearound at a specific point on the dental arch model dm. It is explained referring to FIG. 15c. The standard observational direction "v" is understood that it goes along a line pv connecting a specific point pa and a specific point pb in a three-dimensional space. The line pv intersects at a specific one point pt with respect to the dental arch model dm#2 and the point pt is located at the center or around the center of the interested area "r".

There considered a direction vd along the body axis direction connecting the top of head and the leg relative to the point pt and a direction hd orthogonal to the body axis on the plane of the dental arch model dm#2. The line pv is orthogonal to the direction vd and the direction hd on the plane of the dental arch model dm#2. The standard observational direction "v" is set in a direction along the line pv. The standard observational direction "v" is preferably set to give a feeling to an operator seeing the interested area "r" from its front, so that it is not always necessary to set a strictly orthogonal direction but it is enough to set a substantially orthogonal direction. The standard observational direction "v" is also a direction of a normal line or a substantial normal direction relative to the curve of the dental arch DA.

As to FIG. 15b, the standard observational direction can be considered similar to FIG. 15c. In a precise sense, the dental arch model dm#1 in FIG. 15b is a curved plane, so that the tangent line contacting with the plane of the dental arch model dm#1 is assumed on the point pt on which the dental arch model dm#1 and the standard observational direction "v" (line pv) intersect and the direction orthogonal to the tangent line is set as a standard observational direction "v". In case of panoramic radiography, the X-ray slit beam has been incident so as to be orthogonal to the dental arch as far as possible in the prior art and the incident direction may be set as a standard observational direction "v".

Figure 15D:
Figure 15E:

The dental arch model dm may be a standard curve dm#3 in FIG. 15d in which the standard curved plane dm#1 is further simplified, namely is projected on a two-dimensional plane or a standard composite line dm#4 in FIG. 15e in which the standard composite plane dm#2 is further simplified, namely is projected on a two-dimensional plane. The standard one may be prepared as a dental arch model dm, however, more preferable result may be obtained by enlarging or downscaling depending on the physical size, age and sex of a patient. The dental arch model dm includes a standard one prepared in advance, a respective one obtained by processing the image data of the dental arch DA such as the above-mentioned CT data, or a respective one obtained by actually measuring the shape of the dental arch DA of the object "o" to be examined.

The dental arch model dm is set as a space coordinate at a spatial position of the X-ray CT apparatus body M1, or at a spatial position relative to a spatial coordinate occupying the X-ray CT apparatus body M1. The spatial position or the spatial coordinate of the dental arch model dm may be called as the spatial position or the spatial coordinate of the place where X-ray computer tomography is executed.

FIG. 15a is a specific embodiment of the dental arch DA, and FIG. 15b to FIG. 15e show a specific embodiment of the dental arch model dm, respectively. They show the standard curved plane dm#1, the standard composite plane dm#2, the standard curved line dm#3 and the standard composite line dm#4.

The dental arch model dm is not limited to a simple horseshoe. For example, in FIG. 24a only the teeth th among the dental arch DA1 of an upper jaw are shown with solid lines when seen from the right side, FIG. 24b is a view seen from the front. The teeth th11, th31 of the dental arch DA of the upper jaw obliquely extend forward from the apex of root to the dental cervix, so it is preferable to make the area of the dental arch model dm corresponding to the front teeth is spread toward the bottom in accordance with the shape shown in FIG. 24c.

Figure 24A:
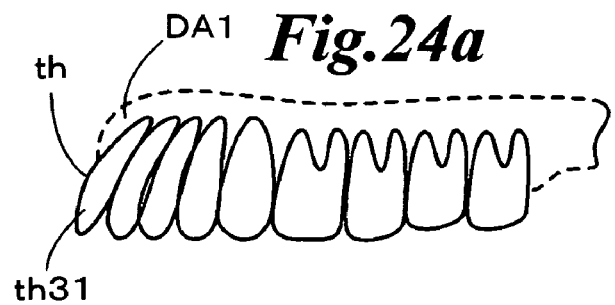
FIG. 24a is a front view of a dental arch.
Figure 24B:
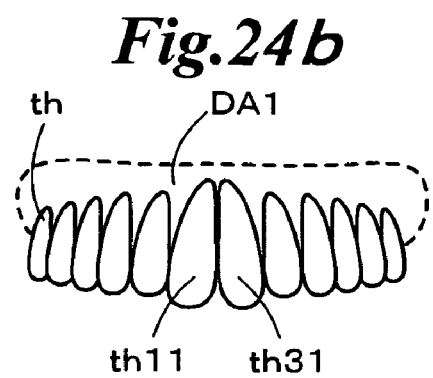
FIG. 24b is a side view of a dental arch.
Figure 24C:
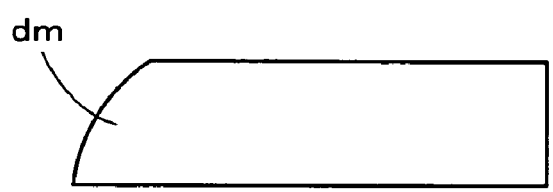
FIG. 24c is a side view of a dental arch model.
Figure 24D:
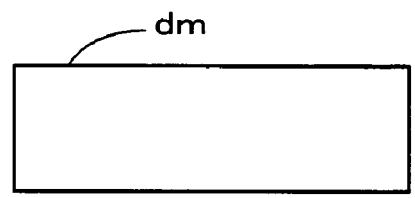
FIG. 24d is a front view of a dental arch model.
Figure 24E:
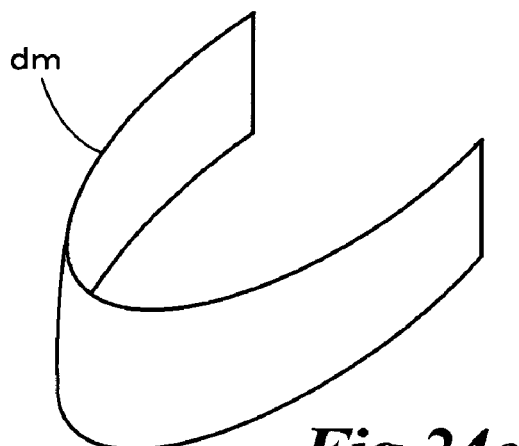
FIG. 24e is a perspective view of a dental arch model.

FIG. 24c to FIG. 24e show an example of the dental arch model dm in accordance with the dental arch DA shown in FIG. 24a and FIG. 24b. FIG. 24c shows the dental arch model dm seen from right, FIG. 24d is a view seen from the front and FIG. 24e is a perspective view of the dental arch model dm. The shape of the dental arch model dm may be appropriately set in this way depending on the actual conditions.

Next, procedures for obtaining the dental arch model dm by image analysis are explained. If the three-dimensional CT data of a maxillofacial area reconstructed from CT data is sliced in a direction of height, an X-ray CT sectional image p#4 in which a cross section of each tooth th is distributed in a form of horseshoe and an X-ray CT sectional image p#4 of the cross section of a jaw bone can be obtained for the dental arch DA. When the distribution pattern of the cross sections is rendered to image analysis, the shape of the dental arch DA can be understood, so that a standard curved plane dm#1 of which difference between the obtained shape becomes smallest may be determined by a method of least squares.

FIG. 16a to FIG. 16d show an example of a plurality of X-ray CT sectional images p#4(b)-(d) which are obtained by slicing the three-dimensional CT data (a) reconstructed with the CT data at different height. In these figures, CT data obtained by a broad computer tomography can be used as shown in the figure, however, the CT data obtained by a local computer tomography may be used as mentioned later referring to FIG. 21.

The X-ray CT sectional image p#4(b) in the figure shows that the cross sections of the center of each tooth th are distributed in a form of horseshoe. The X-ray CT sectional image p#4(c) shows that the cross section of the dental root of each tooth th and the cross section of a lower jaw are distributed in a form of horseshoe, and the X-ray CT sectional image p#4(d) shows the cross section of a lower jaw is distributed in a form of horseshoe. By detecting these distribution pattern by image analysis, the shape of the dental arch DA can be obtained and the dental arch model dm is determined according the shape.

Figure 17A:
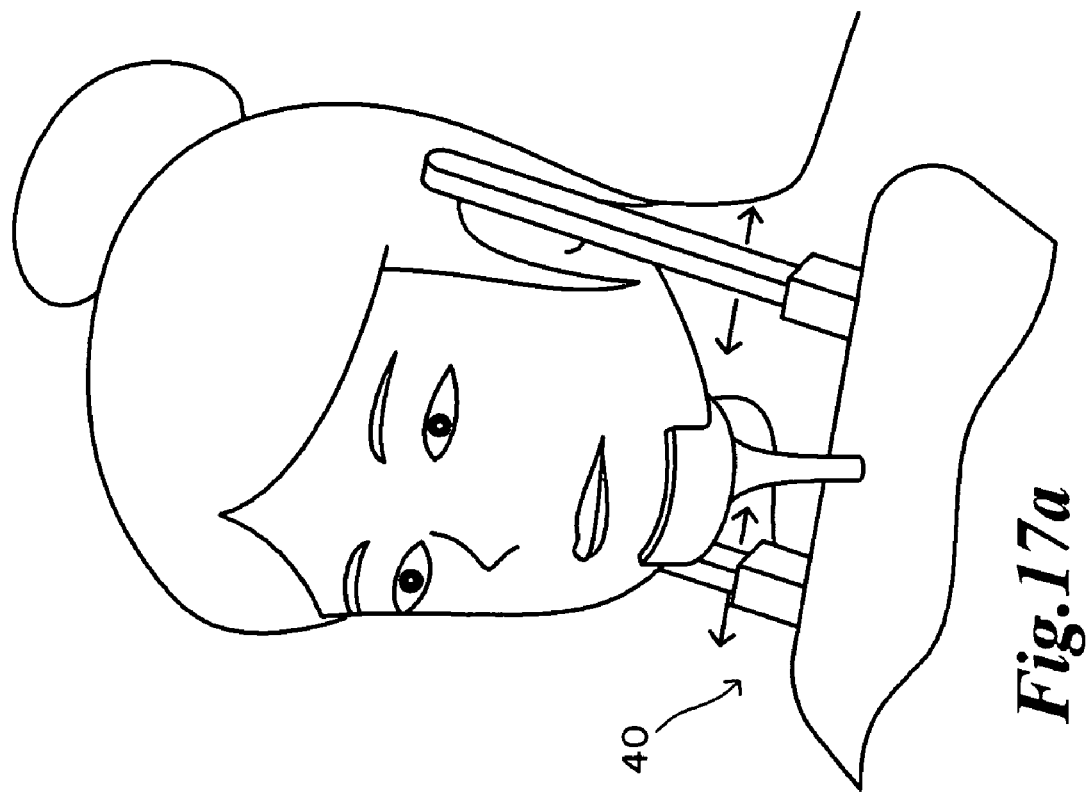
FIG. 17a is an explanatory view showing the mechanism of an object holding means for assuming the shape of a dental arch and FIG. 17b is an explanatory view showing the positional relation of an object holding means and a dental arch model.
Figure 17B:
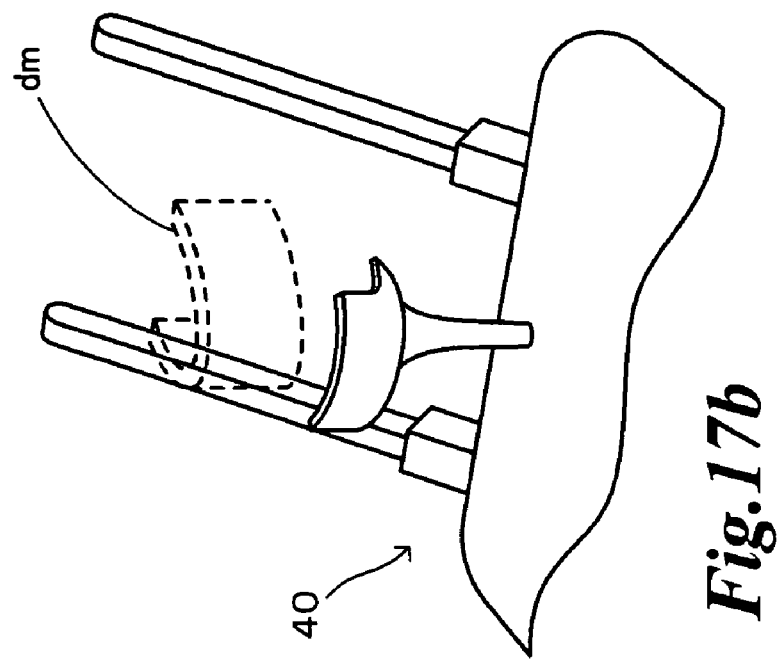

The dental arch model dm may be obtained by actually measuring the dental arch DA of the object "o". For example, as shown in FIG. 17a and FIG. 17b, a holder part of the object holding means 40 for holding the object "o" during radiography may be designed to be movably adjustable according to the object "o" and the shape of the dental arch DA may be assumed by the adjustment value. In such a case, it is required to study and prepare the relative relation of the adjustment value of the holder part of the object holding means 40 depending on the object "o" and the dental arch model dm.

In FIG. 17a and FIG. 17b, two ear rods for holding a head are movable and its width can be enlarged or reduced according to the size of the head. The shape of the dental arch model dm may be varied depending on the open degree of the two year rods. Specifically, when the open degree of the two year rods is large, a dental arch model dm having a large arc is set, and when it is small, a dental arch model dm having a small arc is set.

As shown in the figure, the dental arch model dm is set in the three-dimensional space where the X-ray CT apparatus body M1 is provided relative to the spatial position of the object holding means 40, namely the spatial position of the X-ray CT apparatus body M1. The spatial position of the dental arch model dm may be called as the spatial position where X-ray computer tomography is executed. The actual measurement of the shape of the dental arch DA may be achieved by another method. For example, a flat pressure-sensitive switch is bit by a patient with the head fixed and the curved shape of the dental arch DA may be detected by obtaining the two-dimensional coordinate information or the three-dimensional coordinate information at the point where a high pressure is measured.

Figure 6:
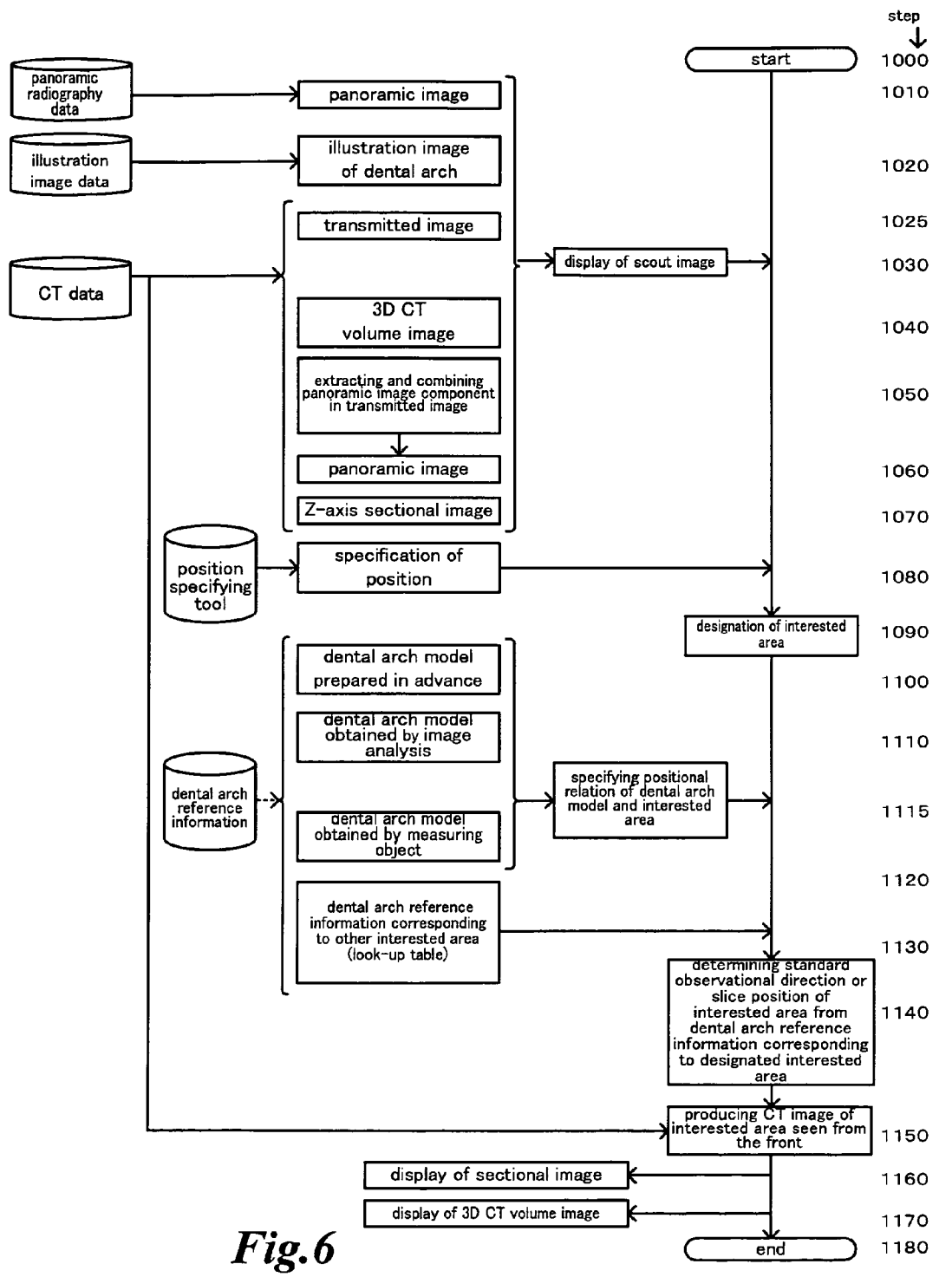
FIG. 6 is a flow chart explaining basic structure of broad computer tomography according to the present invention.

FIG. 6 is a flow chart explaining the basic procedures of the above-mentioned broad computer tomography.

The basic procedures comprise a step (1090) of designating of an interested area "r", a step (1140) of determining the standard observational direction "v" of the interested area "r" from the dental arch reference information corresponding to the designated interested area "r", a step (1150) of producing a sectional image or a three-dimensional CT volume image from the CT data, the images being the standard observational X-ray CT image of the interested area "r", and a step (1160 or 1170) of showing the produced standard observational X-ray CT image. The interested area "r" is the area to be seen from the front, namely the standard observational objective area and is designated in a part of a maxillofacial area, specifically a part of the dental arch DA.

Designating of the interested area "r" may be a method of designating the interested area "r" on the image (step 1030) such as a method of designating of the interested area "r" on the scout image showing the dental arch DA on the display means 88 or a method without using a scout image on the display means 88 such as a designation method of the interested area "r" by means of a code allotted to each region of the dental arch DA. These methods are detailed later.

The standard observational direction "v" and the slice position sl may be calculated from the shape of the dental arch model dm based on the three-dimensional shape of the dental arch DA (step 1100, 1110, 1120→1115→1140) and the data table (look-up table) which provides the standard observational direction "v" and the slice position sl per each region of the interested area "r" may be referred (step 1130→1140).

Next explained is a designation method of the interested area "r". Designating the interested area "r", namely the objective display area, there are a method using a scout image and a method without using a scout image. The former one is explained at first.

As the scout image for designating the interested area "r", the following images can be used, for example, a panoramic image p#1 of the maxillofacial area produced from the panoramic radiography data of the object "o" to be examined radiographed in advance, an illustration P#2 of the dental arch comprised of the illustration image data such as a plan view of the dental arch DA prepared in advance, a panoramic image p#1 of the maxillofacial area produced from the CT data radiographed in advance, an X-ray transmitted image p#3, an X-ray CT sectional image p#4, and a three-dimensional CT volume image p#5.

They are explained referring to each step shown in the flow chart in FIG. 6.

The production of the panoramic image p#1 is shown in the step 1010 in the flow chart of FIG. 6, the production of the illustration p#2 is shown in the step 1020, the production of the transmitted image p#3 is in step 1025, the production of the three-dimensional CT volume image p#5 in the step 1040, and the production of the panoramic image p#1 is in the step 1060.

The scout image is displayed in the step 1030 and designation of the interested area "r" using the scout image is done in the step 1090.

When the interested area "r" is specified on the scout image and the range of the interested area "r" is shown as a frame on the scout image, the area can be intuitively understood, thereby being advantageous.

Figure 7:
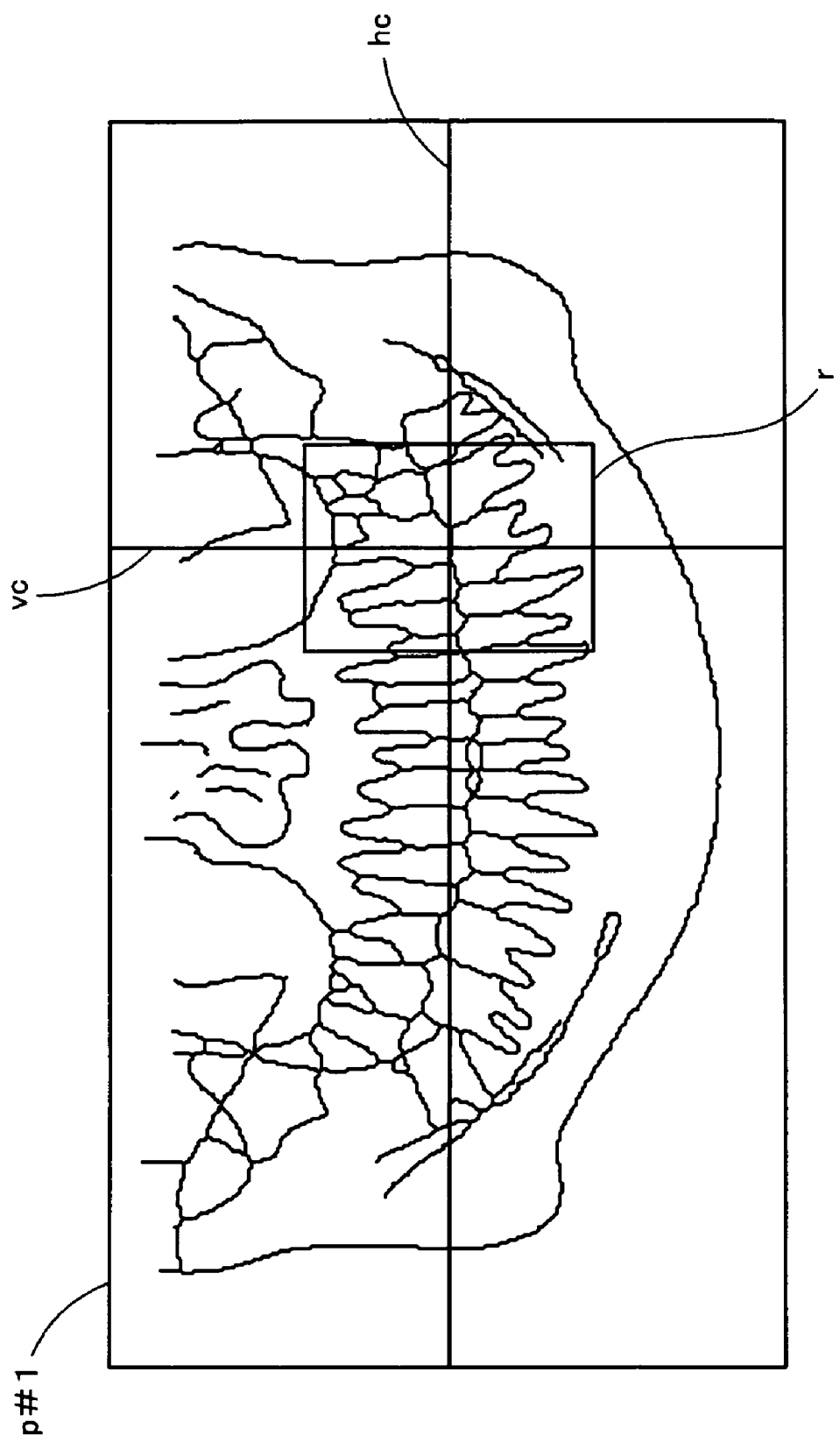
FIG. 7 shows an example of a panoramic image as a scout image.

FIG. 7 shows an example of the panoramic image p#1 as a scout image and the dental arch DA which is actually curved three-dimensionally is developed and shown as a plan view. A horizontal cursor hc and a vertical cursor vc moving according to the manipulation of an operator are overlapped on the panoramic image p#1, the interested area "r" is designated at the intersecting point thereof, and the area is shown with a rectangular frame. In spite of the panoramic image p#1, the illustration p#2 of the dental arch, not shown, which is illustrated from the panoramic image p#1 may be used. The illustration p#2 can be produced from the illustration image data stored in a storage means 82 and the produced illustration p#2 is displayed as a scout image like the panoramic image p#1. The production of the illustration p#2 is shown in the step 1020 in the flow chart of FIG. 6 and the display of the illustration p#2 as a scout image is shown in the step 1030.

Figure 8:
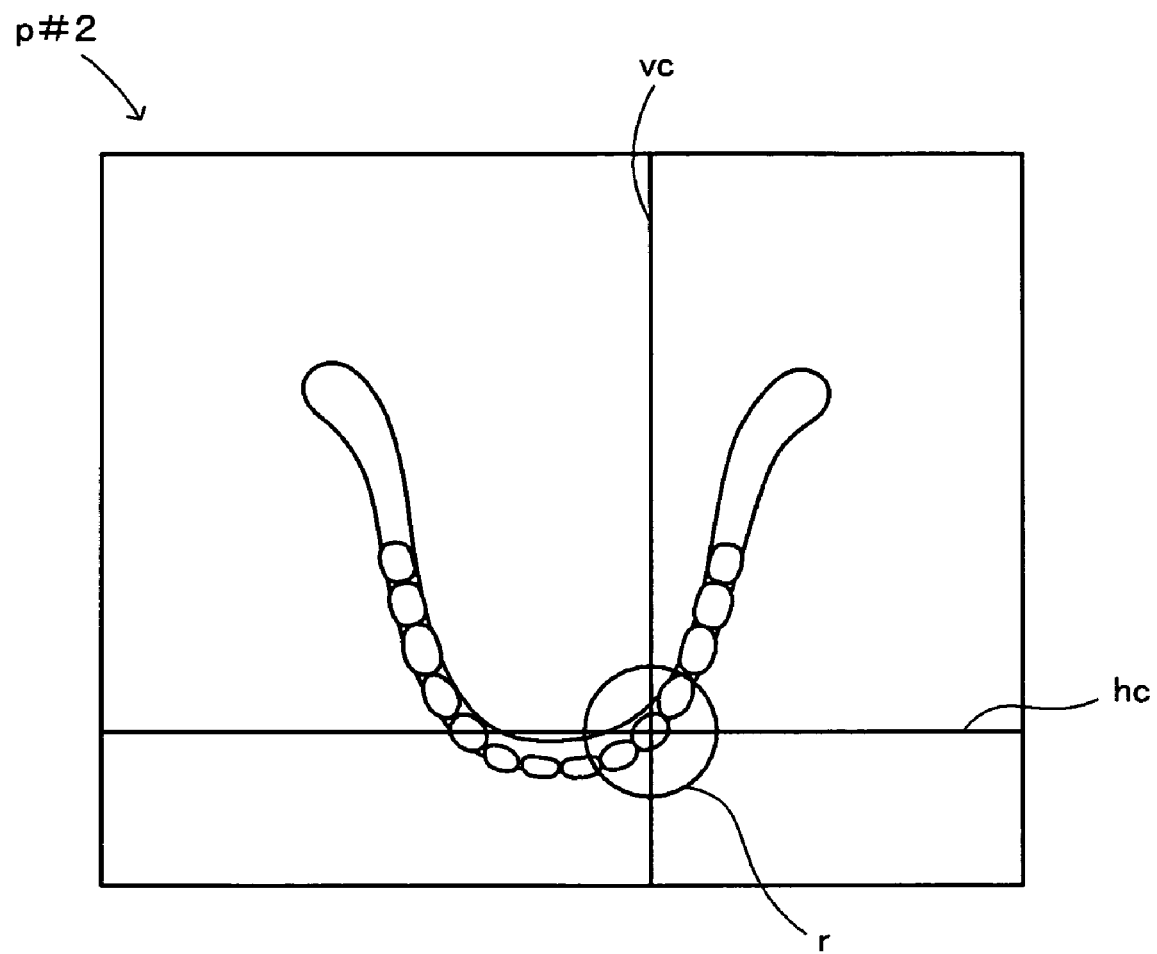
FIG. 8 shows an example of an illustration as a scout image.

FIG. 8 shows other example of the illustration p#2 being a scout image and is a plan view of a standard dental arch DA in which a horizontal cursor hc and a vertical cursor vc which are moved depending on the manipulation of an operator are overlapped and shown and the interested area "r" surrounded with a circular frame is designated at the intersecting point thereof. In this case, the vertical position and area of the interested area "r" become those set in advance including upper and lower tooth portions.

Figure 9:
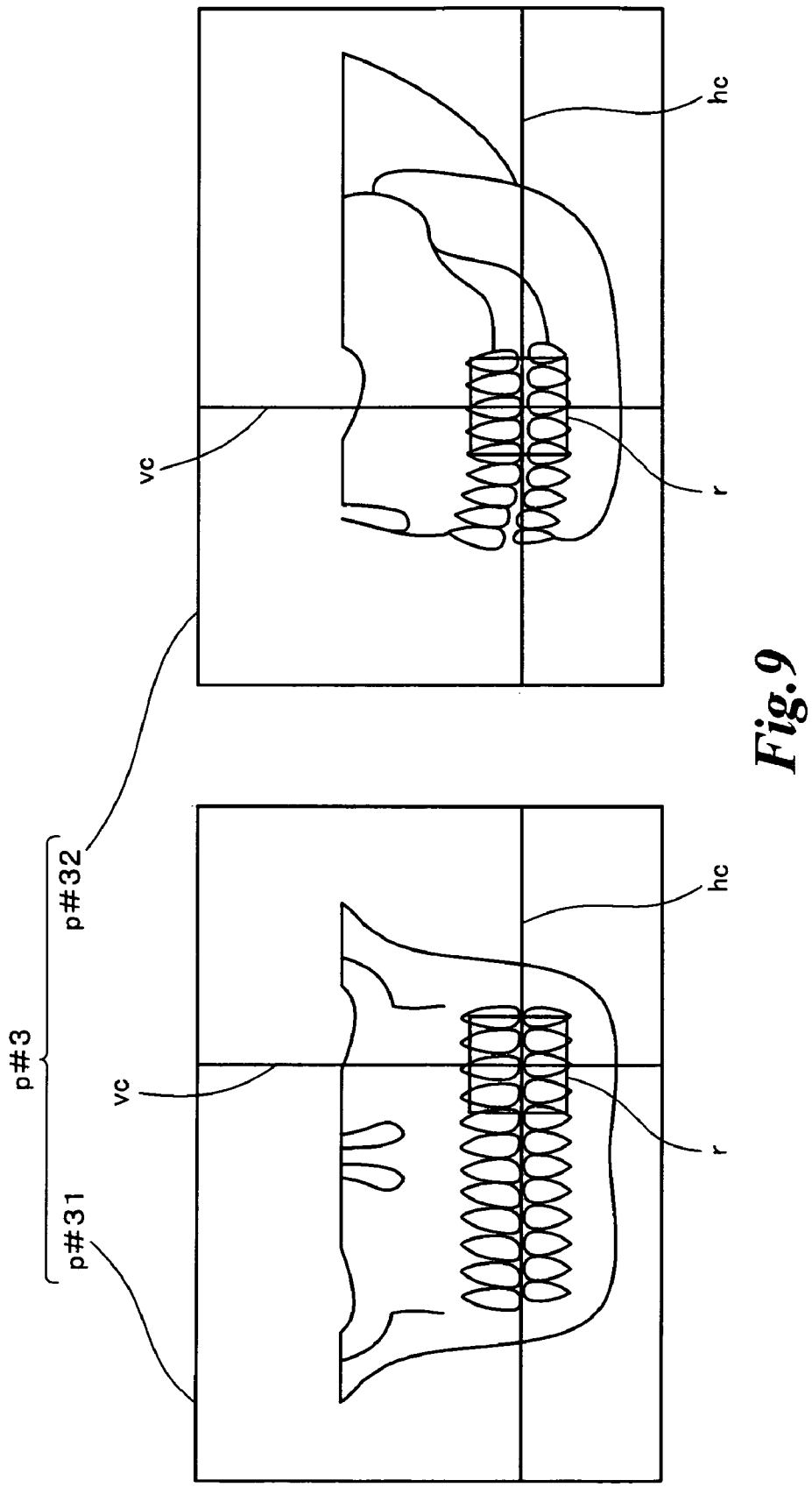
FIG. 9 shows an example of an X-ray transmitted image as a scout image.

FIG. 9 shows an example of an X-ray transmitted image p#3 being a scout image and shows a front X-ray transmitted image p#31 and a side X-ray transmitted image p#32 in which a horizontal cursor hc and a vertical cursor vc which are moved according to the manipulation of an operator are overlapped, and the interested area "r" is designated by the intersecting points thereof as a rectangular frame in the figure.

In case of X-ray computer tomography, the transmitted image p#3 of the object "o" to be examined is obtained per a minute angle of the rotation of the support means 30 as CT data, so that the transmitted image p#3 in the front and the side can be obtained respectively.

Figure 10:
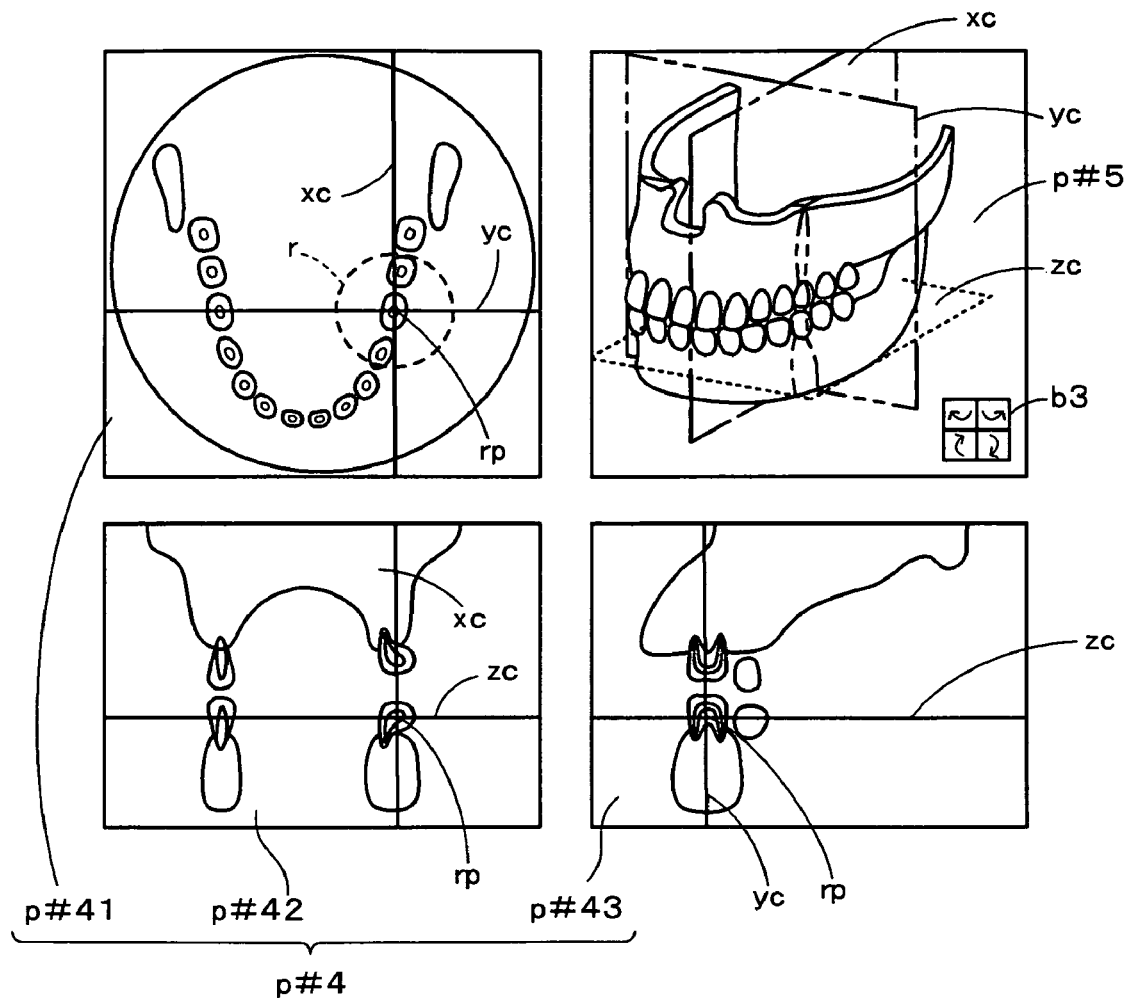
FIG. 10 is an example of an X-ray CT sectional image as a scout image.

FIG. 10 is an example of an X-ray CT sectional image p#4 as a scout image.

The three-dimensional CT data of the three dimensional area of the object to be examined "o" obtained by reconstructing the CT data are produced and an X-ray CT sectional image showing the image of a Z-section (Z-section image) p#41, an X-ray CT sectional image showing the image of a Y-section (Y-section image) p#42, and an X-ray CT sectional image showing the image of an X-section (X-section image) p#43 are displayed in combination as an X-ray CT sectional image p#4 of the sectional plane orthogonal each other for the three-dimensional area. An X cursor xc, a Y cursor yc, and a Z cursor zc which are moved according to the manipulation of an operator are overlapped and shown on these three X-ray CT sectional images p#4. The cursors xc-zc are shown as a projection line of the X-section, the Y-section and the Z-section, respectively. The initial setting is designed such that front teeth are shown directing right below in the figure on the X-ray CT section image p#41.

Referring to each step in the flow chart of FIG. 6, the production of the Z-section image p#41 is shown in the step 1070 in the flow chart of FIG. 6, the display of the Z-section image p#41 as a scout image is shown in the step 1030, and the designation of the interested area "r" using the scout image is shown in the step 1090.

The interested area "r" is designated by the intersecting point rp of the cursors xc, yc, zc. When any one of the cursors xc, yc, zc is operated to be moved, the X-ray CT sectional image p#4 is changed and displayed according to the operation of the cursors xc, yc, zc so as to display the image of the sectional plane corresponding to the operated cursors. At this time the designation of the interested area "r" is received, and it is executed by double-click on the intersecting point rp with a mouse.

A three-dimensional CT volume image p#5 is shown in array as another scout image with the X-ray CT sectional image p#4. The three-dimensional CT volume image p#5 is obtained by a rendering process in which the color information and the clearness information are added to each pixel constituting the three-dimensional CT data depending on the density value and are then overlapped along the display direction. A rotation button b3 for rotating up and down and right and left is also shown on the three-dimensional CT volume image p#5, so that the image can be freely rotated by means of the button b3. It is executed in such a manner that the display direction for the three-dimensional CT data is changed according to the rotating operation and the screen is revised and displayed by the re-rendered image of the three-dimensional CT data according to the changed display direction. Further, the cursors xc, yc, zc are also shown on the three-dimensional CT volume image p#5. The cursors xc, yc, zc show an X-sectional plane, a Y-sectional plane and a Z-sectional plane respectively, so that they are shown as a plane on the three-dimensional CT volume image p#5 respectively. By optionally operating the rotation button b3 and the cursors xc, yc, zc, the interested area "r" can be designated at a desired position.

Here, the panoramic image p#1 as a scout image is supplementary explained. The panoramic image p#1 may be produced by the panoramic radiography data of the object to be examined "o" which is radiographed in advance, however, if there are broad CT data, a part of them may be used. Other method is explained hereinafter.

Figure 11:
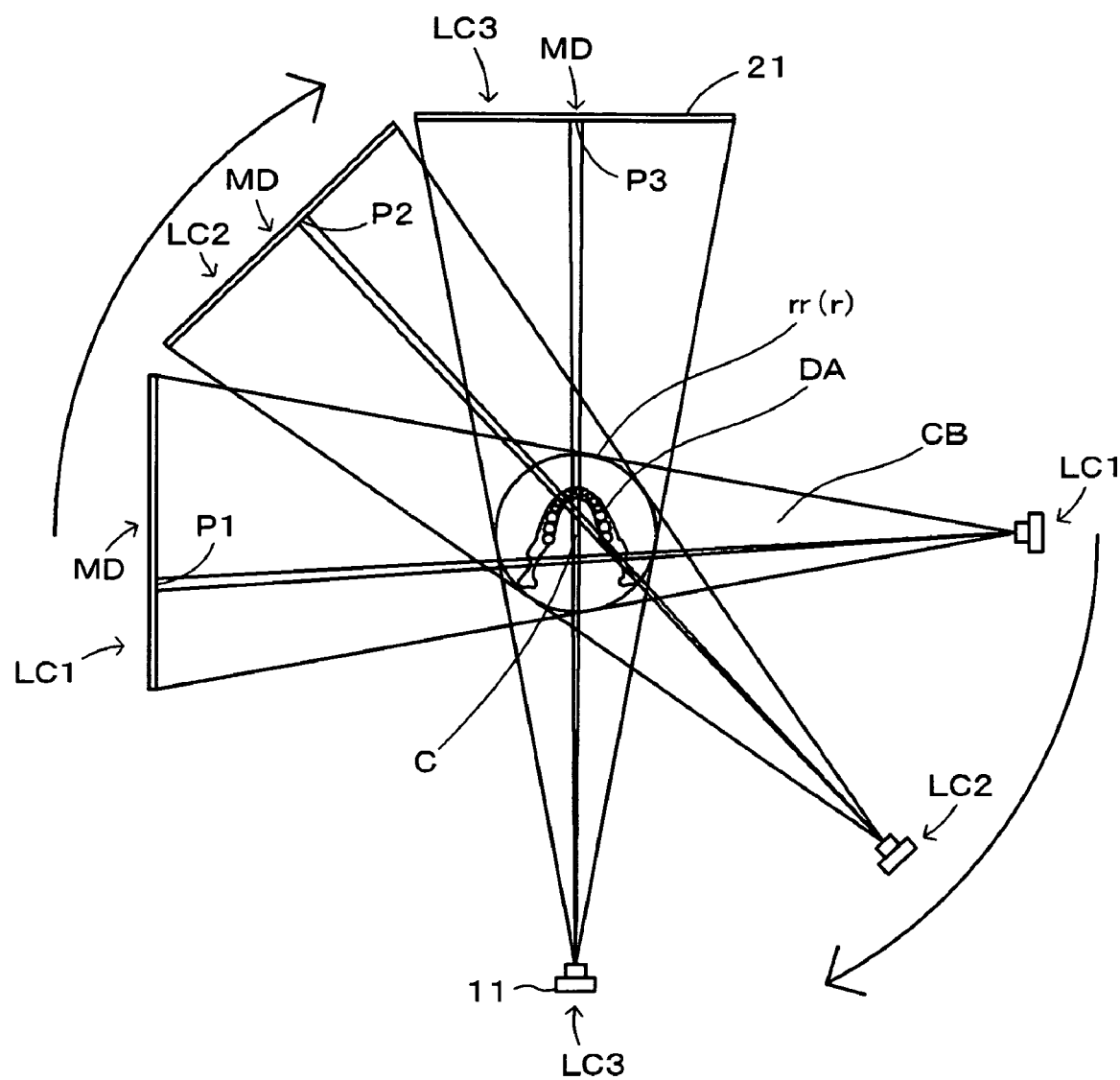
FIG. 11 is a plan view when an object to be examined, an X-ray generator and an X-ray detector are seen from the top in case of broad computer tomography.

FIG. 11 is a plan view when the object "o" to be examined, the X-ray generator 11 and the X-ray detector 21 are seen from the top in case of broad computer tomography. The positional relation of the X-ray generator 11 and the X-ray detector 21 relative to the object "o" is changed from positions LC1 to LC2 to LC3 according to the rotation of the X-ray generator 11 and the X-ray detector 21 around a rotary center "C" of the object "o". The X-ray generator 11 and the X-ray detector 21 rotate around the center "C". In the example of FIG. 4Aa, the X-ray generator 11 and the X-ray detector 21 rotate in a direction shown with arrows in the figure. In case of X-ray computer tomography, the transmitted image p#3 of the object "o" is obtained per a minute rotary angle of the support means 30 as CT data, so that the transmitted image p#3 at each position LC1, LC2, LC3 can be obtained.

In is understood a component P1 is included in the position LC1, P2 in LC2 and P3 in LC3 in the transmitted image p#3 obtained by detecting a broad X-ray beam CB on the detection plane of the X-ray detector 21. The components P1, P2, P3 are those of an elongated X-ray slit beam NB along the body axis of a patient. When the middle point of the detection plane of the X-ray detector 21 is set as MD, the component P1 is at rather right from the middle point MD facing the detection plane at the position LC1, the component P2 is at rather left from the middle point MD facing the detection plane at the position LC2, and the component P3 is at substantially the same position with the middle point MD facing the detection plane.

Figure 12:
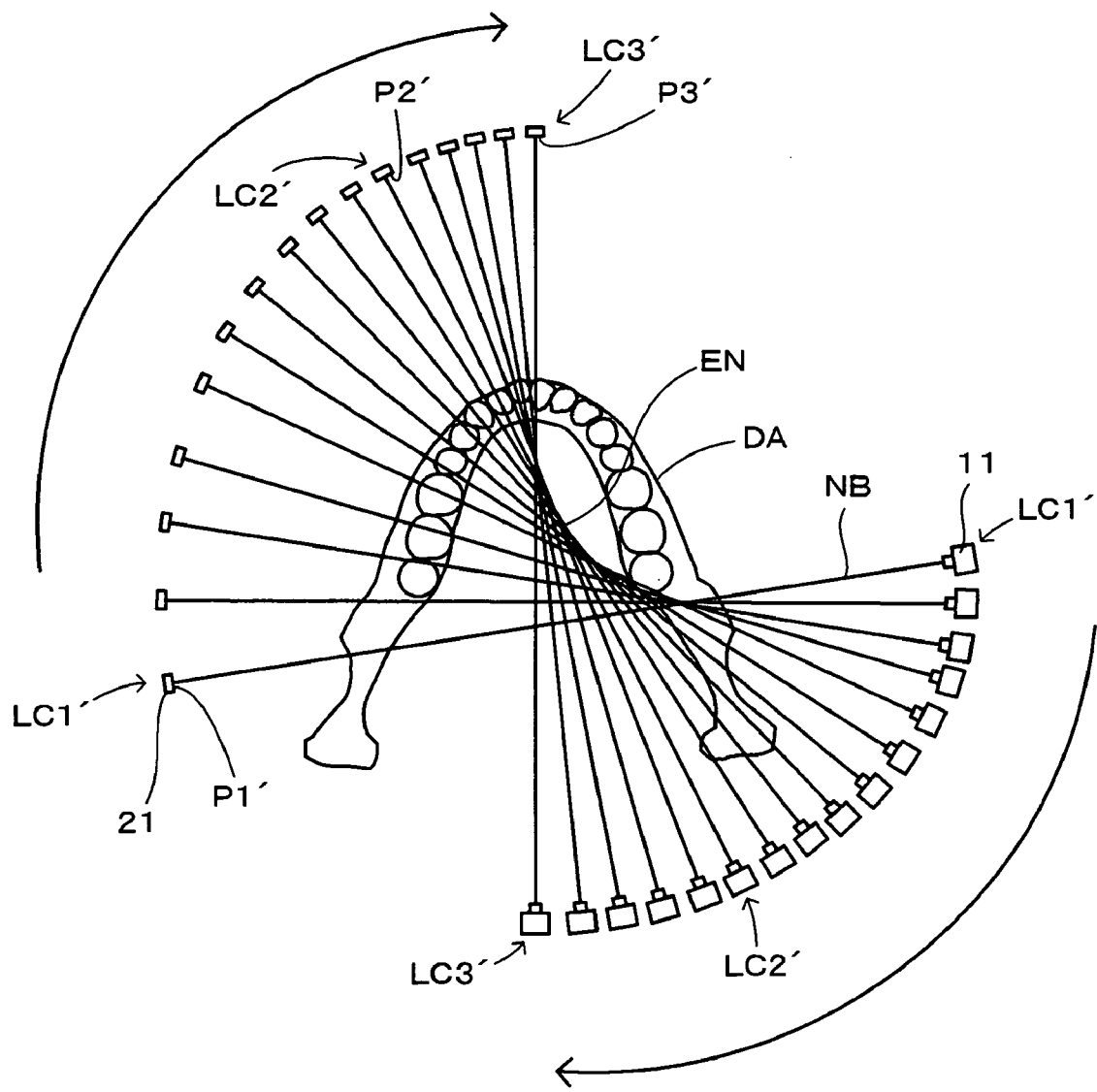
FIG. 12 is a plan view showing a panoramic radiography along a prior orbit.

On the other hand, FIG. 12 is a plan view showing a panoramic radiography along a prior orbit. The positional relation of an X-ray generator 11' and an X-ray detector 21' relative to a dental arch DA' is changed from LC1' to LC2' and to LC3', namely from the position where X-rays are irradiated on a left jaw and to the position where X-rays are irradiated on the center of the front teeth according to the rotation of the X-ray generator 11' and the X-ray detector 21' interposing the dental arch DA. Curved line EN is an envelope curve drawn by an orbit of the X-ray slit beam NB. In the example of FIG. 12, the X-ray generator 11 and the X-ray detector 21 rotate around the rotary axis 30c of the support means 30, namely the extended line 30cl of the rotary axis 30c to be displaced while interposing the dental arch DA.

Figure 13:
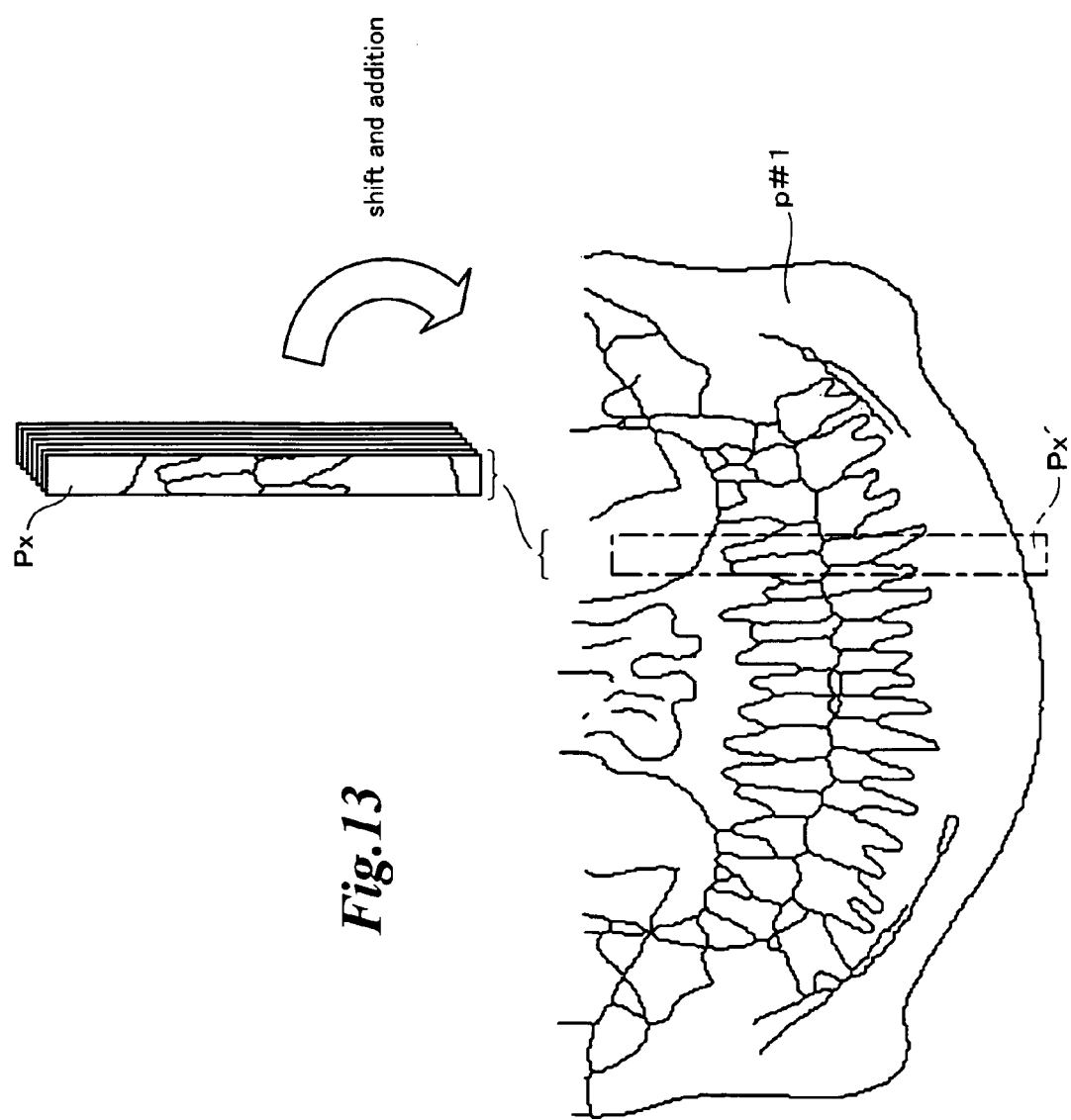
FIG. 13 is an explanatory view showing the principle how a panoramic image is produced from the component of a panoramic image.

Comparing FIG. 11 with FIG. 12, the component P1 is almost the same as P1', the component P2 is almost the same as P2', and the component P3 is almost the same as P3'. Therefore, as shown in FIG. 13, the components of the panoramic image p#1 such as the components P1, P2, P3 are slid to be overlapped and combined (shift and add) to produce the panoramic image p#1. A portion Px' of the panoramic image p#1 is basically comprised of the part corresponding to the component Px in the figure and the neighboring component is shifted and added to the component Px to produce the portion Px'. The technology using an ortho-X-ray cone beam as disclosed in JP-A-2000-139902, which is a prior art of the applicant of the present invention, may be put into practice for producing the panoramic image p#1.

The above is explained referring to each step in the flow chart of FIG. 6.

The production of the panoramic image p#1 by extracting and combining the components of panoramic image p#1 such as the components P1, P2, P3 is shown in the steps 1050, 1060 in the flow chart of FIG. 6. The display of the panoramic image p#1 as a scout image is shown in the step 1030, and the designation of the interested area "r" with the scout image is shown in the step 1090.

The X-ray CT apparatus body M2 may of course execute the panoramic radiography according to the prior orbit shown in FIG. 12 by the total movement of the support means 30 and either one of the XY table 62 or the XY table 64, mentioned above.

More specifically, the support means 30 is rotated while fixing the object holding means 40, the rotary axis 30c of the support means 30 is moved by the XY table 62, and a panoramic radiography according to the prior orbit may be executed in such a manner that a straight line connecting the focal spot of generated X-ray generation from the X-ray tube of the X-ray generator 11 and the middle point MD of the detection plane of the X-ray detector 21 draws an envelope line.

Otherwise, the support means 30 is rotated with the rotary axis 30c fixed and the object holding means 40 is moved by the XY table 64, and a panoramic radiography may be executed in such a manner that the supporting means 30 is moved relatively and that the straight line connecting the focal point of X-ray generation from the X-ray tube of the X-ray generator 11 and the middle point MD of the detection plane of the X-ray detector 21 draws an envelope line when seen from the object "o" to be examined.

Still further, the rotary axis 30c is moved by the XY table 62 and the object holding means 40 is simultaneously moved by the XY table 64 while the support means 30 is rotated, and a panoramic radiography may be executed in which the supporting means 30 is moved relatively in such a manner that the straight line connecting the focal point of X-ray generation from the X-ray tube of the X-ray generator 11 and the middle point MD of the detection plane of the X-ray detector 21 draws an envelope line when seen from the object "o" to be examined.

Next, other method of designating the interested area "r" on the illustration p#2, not on the scout image shown on the display means will be described.

FIG. 14 is an example of illustration p#2 showing the dental arch DA provided on the operation panel 74 shown in FIG. 2a. The illustration p#2 may be drawn with paint, formed with a resin of thin layer and attached thereon, or a three-dimensional model. Codes "11"-"18", "31"-"38", "21"-"28", and "41"-"48" are allotted for each tooth th, and further a button bt is provided for each tooth therearound, and the same codes are allotted on each button bt. Any one of buttons bt is operated, the interested area "r" is designated at a standard position of each tooth th allotted with the code. For this purpose, the standard position is set in advance for each tooth th.

Referring to the steps in the flow chart of FIG. 6, the codes "11"-"18", "31"-"38", "21"-"28", and "41"-"48" are a position specifying tool and the specifying this tool is executed in the step 1080 in the flow chart of FIG. 6, and the designation of the interested area "r" by specifying the position is executed in the step 1090.

For designating the interested area "r", a method without using an image is possible, so the method is explained hereinafter. The illustration p#2 is used for designating the interested area "r" in the example of FIG. 14, however, if the above-mentioned codes are allotted for each tooth th in advance, it is not necessary to provide the illustration on the operation panel 74, so that the interested area "r" may be designated by selecting the code allotted to the tooth th by means of the operation panel 74 or the operation means 86.

In this case, the illustration p#2 may be shown on an optional place of the apparatus in order that an operator may refer when necessary.

The illustration p#2 and the buttons bt may be provided for the operation panel 74, or a further operation box 75 may be provided for or connected with the X-ray CT apparatus M separately and they may be provided on the operation box 75.

Referring to each step in the flow chart of FIG. 6, the code allotted for the tooth th is a position specifying tool and the specifying of the position with this tool is executed in the step 1080, and the designation of the interested area "r" by specifying the position is executed in the step 1090.

As mentioned already, an optionally shaped dental arch model dm can be prepared in advance. Preparing a dental arch model dm in advance is shown in the step 1100 in the flow chart of FIG. 6.

As also mentioned already, the dental arch model dm may be obtained by image processing. Having the dental arch model dm obtained by image analysis is shown in the step 1110 in the flow chart of FIG. 6. Further, it is already described that the dental arch model dm may be obtained by actually measuring the object body "o" and the dental arch DA.

Having the dental arch model dm obtained by actual measurement of the object "o" and the dental arch DA is shown in the step 1120 in the flow chart of FIG. 6.

On the other hand, the standard observational direction "v" of the interested area "r" can be obtained by specifying the position of the interested area "r" for the dental arch model dm, but it is required that the designated position on the scout image, namely the coordinate, is to be corresponded to or to be converted to the coordinate of the dental arch model dm for specifying the position of the interested area "r" for the dental arch model dm.

The coordinate process for this purpose can be defined in advance. For example, the scout image is a panoramic image p#1, the panoramic section to be produced as an image is set in a three-dimensional space in case of a panoramic radiography. The panoramic section can be a dental arch model dm.

The panoramic image p#1 in which the panoramic section is imaged corresponds to that in which a standard curved plane of the dental arch model dm is extended on a flat plane, so that the specified position, namely the coordinate, on the panoramic image p#1 can be corresponded to the coordinate of the dental arch model dm and the specific coordinate of the corresponding dental arch model dm can be specified by selecting a specific position (coordinate) of the panoramic image p#1.

As mentioned above, if the illustration p#2 of the dental arch, not shown, in which the panoramic image p#1 is illustrated is used instead of the panoramic image p#1, it corresponds to that in which a standard shaped dental arch model dm is extended on a flat plane as mentioned above and the specific coordinate of the corresponding dental arch model dm can be designed to be specified by selecting a specific position (coordinate) of the illustration p#2.

If the scout image is the illustration p#2 which is modeled by the flat plane of the dental arch DA, its shape corresponds to such a shape that the standard curved plane of the dental arch model dm is seen from the top, and the dental arch model dm is set to be overlapped on the part corresponding to the panoramic section at the substantial center of the dental arch DA shown by the illustration. It can be set that a specific coordinate of the corresponding dental arch model dm can be specified by selecting a specific position (coordinate) of the illustration p#2.

Although explanations are given referring to FIG. 23, and FIG. 23A to FIG. 23E, it is preferable the standard observational direction "v" of the standard observational X-ray CT image is a normal line direction of the dental arch model dm relative to a central curved line and is shown with arrows in FIG. 15b-FIG. 15e. When the position of the interested area "r" is designated relative to the dental arch model dm, the standard observational direction "v" can be easily calculated or set based on the shape of the dental arch model dm.

Specifying the position of the interested area "r" relative to the dental arch model dm is shown in the step 1115 in the flow chart of FIG. 6. The standard observational direction "v" is not necessarily a strict normal line direction, however, it is required to give a feeling of viewing the interested area "r" from its front. As described referring to FIG. 23 and FIG. 23A to FIG. 23E, when the coordinate and position of the interested area "r" relative to the coordinate and position of dental arch model dm are specified, the standard observational direction "v" and the slice position sl can be set.

It is possible to directly obtain the standard observational direction "v" from the selection information of the tooth th and the positional information of the interested area "r", and its method will be explained.

Figure 18A:
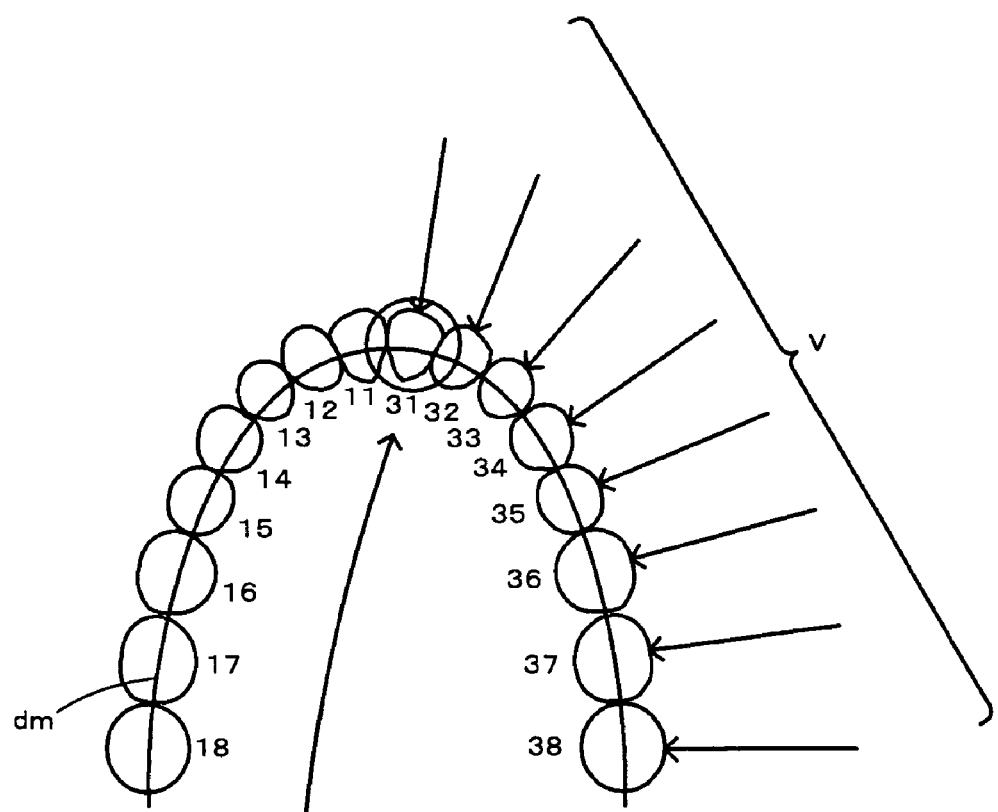
FIG. 18a shows a standard observational direction with respect to each tooth of a dental arch and FIG. 18b is an enlarged view of tooth.
Figure 18B:
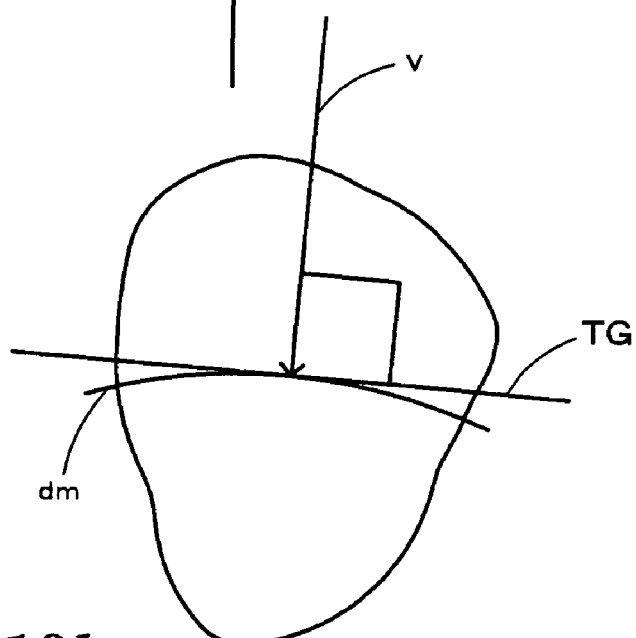

FIG. 18a shows a standard observational direction "v" relative to each tooth th of a standard dental arch DA and the codes are allotted similar to FIG. 14. In FIG. 18a, only an upper jaw is shown and the standard observational direction "v" is only indicated for the tooth th allotted with codes "31"-"38" respectively, but it will be also indicated for other tooth th. The curve of the dental arch DA is shown with a dental arch model dm. FIG. 18b is an enlarged view of the tooth th allotted with the code "31" and shows the standard observational direction "v" which is perpendicular to the curve of the dental arch DA, namely the tangent line TG to the dental arch model dm. As shown in these figures, the standard observational direction "v" for each tooth th is determined in advance, so that if a look-up table which provides each tooth and the corresponding standard observational direction "v" thereof is prepared in advance, the standard observational direction "v" is immediately obtained by selecting the tooth th to be seen from the front. Otherwise, a look-up table which provides each tooth th and the corresponding slice position sl thereof as described referring to FIG. 23 and FIG. 23A to FIG. 23E may be prepared. Or the look-up table may provide each position capable of designating the interested area "r", and the standard observational direction "v" and the slice position sl at the position. Selection of the code allotted for the tooth th may be executed by the operation panel 74 or the operation means 86.

Providing such a look-up table is shown in the step 1130 in the flow chart of FIG. 6.

On the other hand, the code for the tooth th to be viewed from the front and the interested area "r" may be specified cooperatively. Namely, when a tooth th is selected by operating the button bt or inputting the codes shown in FIG. 14, the interested area "r" including the tooth th is automatically designated, and the look-up table is referred according to the positional information of the interested area "r". Or, when an interested area "r" is designated, the tooth th at the center of the interested area "r" is automatically selected, and the look-up table is referred depending on the selection information of the tooth th. Such a look-up table may be obtained by the image processing of the image data of the dental arch DA and by measuring the shape of the dental arch DA like the dental arch model dm.

Referring to the step in the flow chart of FIG. 6, there are many methods for specifying the interested area "r" as mentioned already, however, determining the standard observational direction "v" or the slice position sl from the dental arch reference information corresponding to the designated interested area "r" in any cases is shown in the step 1140 in the flow chart of FIG. 6.

Next, the standard observational X-ray CT image which is displayed according to the present invention is explained. The standard observational X-ray CT image is an image produced by the three-dimensional CT data of the three-dimensional area of the object "o" to be examined which is reconstructed by backprojecting the CT data by means of a convolution method and includes an X-ray CT sectional image p#4 in which the three-dimensional CT data is sliced and a three-dimensional CT volume image p#5 in which the three-dimensional CT data is rendered, however, it is not limited to such images. The positioning of the dental arch DA of the reconstructed three-dimensional CT data is known because the positioned object "o" to be examined is radiographed in case of computer tomography. Therefore, in order to produce the X-ray CT sectional image p#4 as a standard observational X-ray CT image, the sectional plane is selected relative to the standard observational direction "v" and the three-dimensional CT data may be sliced at the position of the interested area "r" by the selected slice plane. In this case the standard observational X-ray CT image is produced as any one of three X-ray CT sectional images p#41-p#43 like the X-sectional plane, the Y-sectional plane and the Z-sectional plane which are produced from the CT data and are orthogonal each other and they may be combined and simultaneously displayed. The X-ray CT sectional image p#4 to be the standard observational X-ray CT image may be a broad image including the interested area "r" of the maxillofacial area or may be a local one limited to the interested area "r".

Figure 19A:
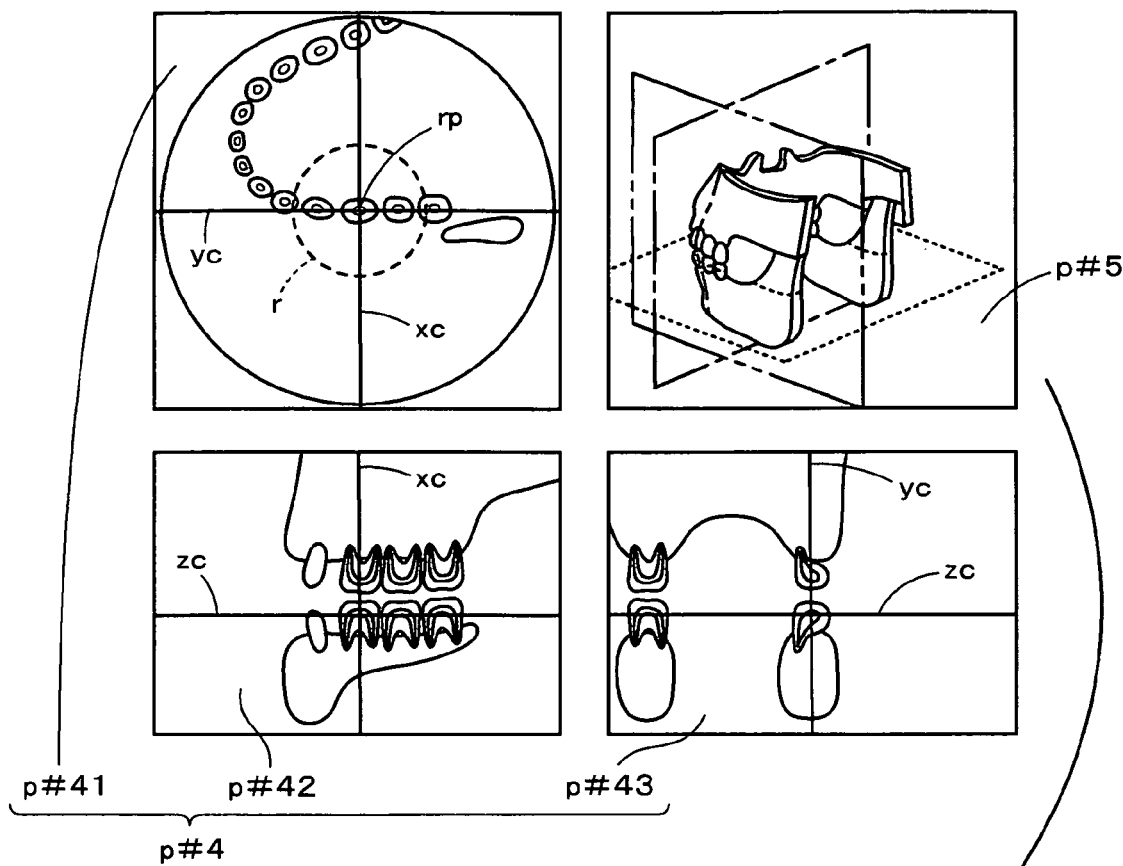
FIG. 19a is an example of a standard observational X-ray CT sectional image of an interested area and FIG. 19b is an example of a standard observational three-dimensional CT volume image of an interested area.

FIG. 19a is an example of the X-ray CT sectional image p#4 being the standard observational X-ray CT image and the X-ray CT sectional image p#42 among the three X-ray CT sectional images p#41-p#43 is a standard observational X-ray CT image. Therefore, on the X-ray CT sectional image p#42 the longitudinal direction of the dental arch DA in the interested area "r" is shown with an angle so as to go along the Y-cursor yc shown on the X-ray CT sectional image p#41. Comparing the X-ray CT sectional image p#42 with the X-ray CT sectional images p#42, p#43 shown as an example of a scout image in FIG. 10, they are different in that the Y-axis of the former directs to be perpendicular to the dental arch DA in the interested area "r" (standard observational direction "v") but the Y-axis of the latter directs so as to diagonally intersect the dental arch DA in the interested area "r". Therefore, the interested area "r" on the X-ray CT sectional image p#42 being a standard observational X-ray CT image is displayed in an extremely similar manner to the corresponding portion of the panoramic image p#1 which is familiar with a dentist.

Figure 19B:
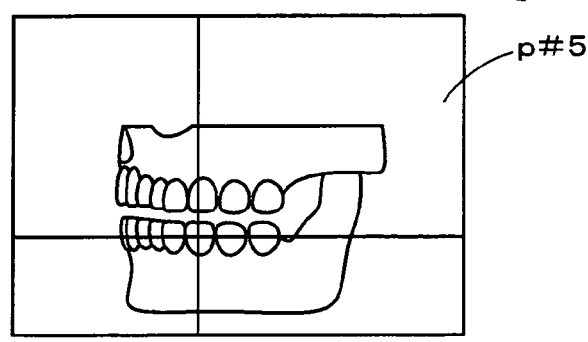

FIG. 19a also shows the three-dimensional CT volume image p#5 of the maxillofacial area seen obliquely which is produced from the CT data in combination with other images. On the other hand, the three-dimensional CT volume image (standard observational three-dimensional CT volume image) p#5 produced as a standard observational X-ray CT image as shown in FIG. 19b may be displayed. Such a three-dimensional CT volume image p#5 is obtained by adding the color information and the clear information depending on the density value to each pixel constituting the three-dimensional CT data and by being overlapped so as to become an image which is seen in a standard observational direction "v". The three-dimensional CT volume image p#5 may be a broad image including the entire maxillofacial area or may be a local one limited to the interested area "r".

For displaying a standard observational X-ray CT image, a broad computer tomography and a local computer tomography may be used as mentioned above. The image such as FIG. 19 may be displayed or the image such as FIG. 22 mentioned later may be displayed.

Referring to the step in the flow chart of FIG. 6, producing a standard observational X-ray CT image of the interested area "r" is shown in the flow chart of FIG. 6.

Further, displaying the sectional image p#4 as a standard observational X-ray CT image is shown in the step 1160 and displaying the standard observational three-dimensional CT volume image as a standard observational X-ray CT image dp is shown in the step 1170.

Although the explained above are embodiments in which almost the entire maxillofacial area including the entire dental arch DA is radiographed, they may be applicable to a computer tomography in which a part of the dental arch DA, not the entire area, is radiographed. For example, in case of computer tomography for the right half of the dental arch DA, for the left half, for the area close to the front teeth, or for the area close to back teeth, the standard observational X-ray CT image can be obtained in the same manner only if the dental arch model dm which fits to the area is prepared.

Figure 20:
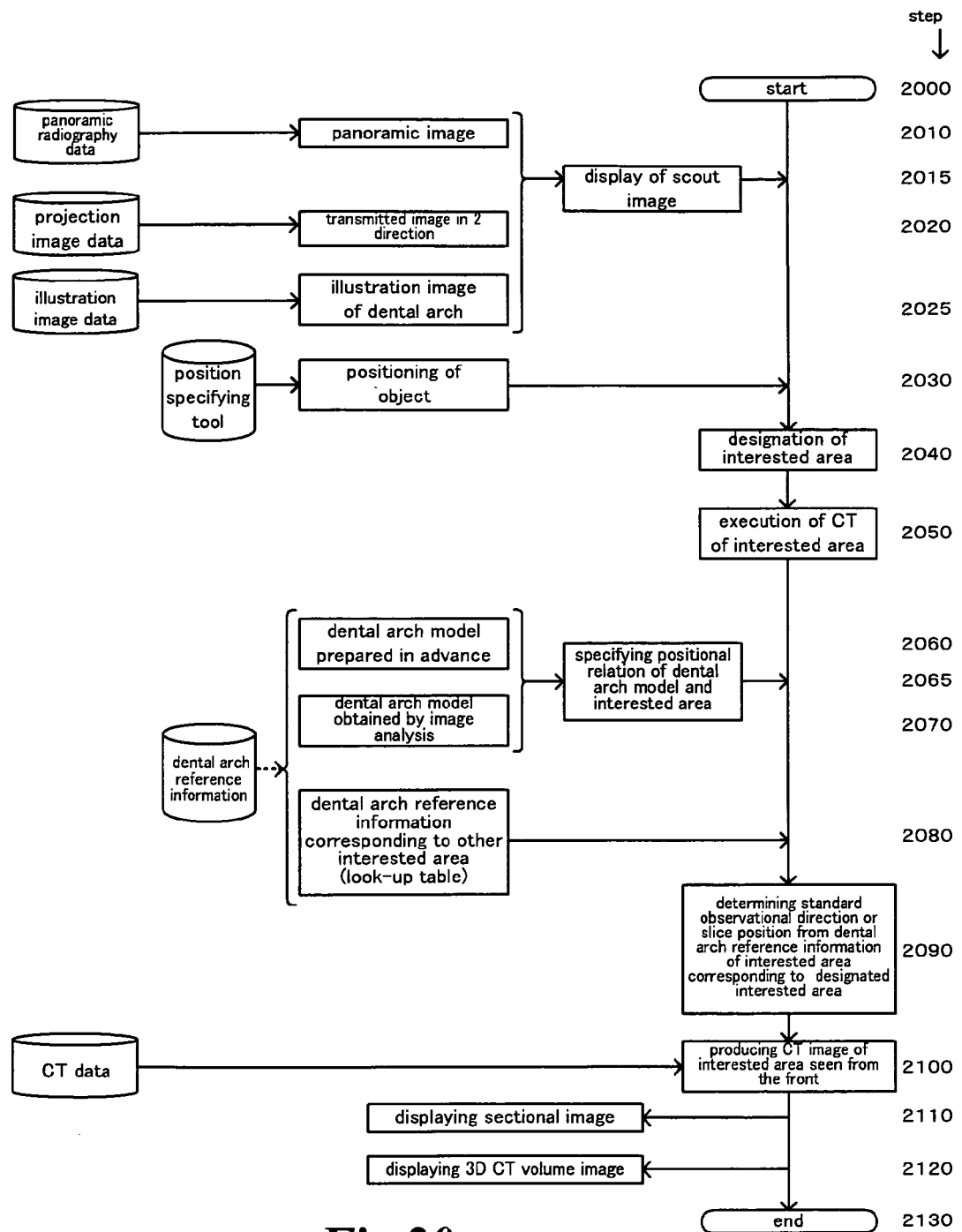
FIG. 20 is a flow chart explaining the basic procedure of a local X-ray computer tomography according to the present invention.

Next, the structure according to the flow chart of FIG. 20 is explained. This flow chart explains the basic procedure in which a local radiography is executed for the area designated as the interested area "r" and the standard observational X-ray CT image is produced from the obtained CT data.

The basic procedure are: a step of designating the interested area "r" (2040); a step of executing a computer tomography so as to include the interested area "r" in the area to be radiographed (objective radiography area) rr depending on the position of the designated interested area "r"; a step of determining the standard observational direction "v" or the slice position sl of the interested area "r" from the dental arch reference information corresponding to the designated interested area "r" (2090), a step of producing the sectional image being the standard observational X-ray CT image from the CT data (2100), and a step of displaying the three-dimensional CT volume image being a standard observational X-ray CT image (2110 or 2120). The dental arch reference information includes the above-mentioned dental arch model dm and look-up table.

The method of designating the interested area "r" may include a method of designating the interested area "r" by a scout image (step 2015) or a method of designating the interested area "r" by means of a partial code of the dental arch DA without using the image (step 2030).

The standard observational direction "v" may be calculated from the shape of the dental arch model dm based on the three-dimensional shape of the dental arch DA (step 2060, 2070→2065→2090) or may be obtained by referring to the look-up table by the positional information of the interested area "r" (step 2080→2090).

A method of designating the interested area "r" is explained in detail. At first a designation method of the interested area "r" on the scout image showing the dental arch DA is described.

The panoramic image p#1 of the maxillofacial area produced from the panoramic radiography data of the object "o" to be examined which is radiographed in advance and the illustration p#2 such as a plan view of the dental arch DA prepared in advance, and the X-ray transmitted image p#3 in two directions can be used as a scout image. When the interested area "r" is designated on the displayed scout image, the position of the interested area "r" is specified on the dental arch model dm and simultaneously the area of the interested area "r" is shown as a frame on the scout image. A standard dental arch model dm prepared in advance and a respective dental arch model dm obtained by actually measuring the shape of the dental arch DA of the object "o" can be of course used as a dental arch model dm.

The illustration p#2, not shown, which is illustrated from the panoramic image p#1 can be used in stead of the panoramic image p#1.

The embodiment in which a panoramic image p#1 is used as a scout image is explained. A panoramic radiography data can be obtained by moving the X-ray generator 11 and the X-ray detector 21 along the panoramic section radiography orbit stored in advance according to the above-mentioned panoramic radiography method for irradiating an X-ray slit beam BN. A panoramic image p#1 of the maxillofacial area is produced from thus obtained panoramic radiography data and is displayed on the display means 88 as explained referring to FIG. 7. The example of the panoramic image which is shown as a scout image is the panoramic image same as the image p#1 in FIG. 7. An operator moves and arranges a pointer by operating a mouse and designates the interested area "r" on the panoramic image p#1.

When a specific position is specified on the panoramic image p#1 displayed as the scout image, the rotary center of the X-ray generator 11 and the X-ray detector 21 is set according to the coordinate of the position. Then at least one of the supporting means 30 or the object holding means 40 is moved and controlled in such a manner that the rotary center of the X-ray generator 11 and the X-ray detector 21 goes to the center of the interested area "r" by designating the interested area "r".

Thereafter, the X-ray generator 11 and the X-ray detector 21 are rotated around the object "o" to be examined, thereby executing a local computer tomography. CT data can be obtained by executing a local CT so as to include the interested area "r" in the area to be radiographed (objective radiography area) rr based on the position of the designated interested area "r".

In the local computer tomography, at least one of the supporting means 30 and the object holding means 40 is moved and controlled in such a manner that the rotary center of the X-ray generator 11 and the X-ray detector 21 goes to the center of the interested area "r" of the interested area "r", as mentioned above. When the center of the X-ray generator 11 and the X-ray detector 21 accords with the rotary center of the supporting means 30, the rotary center of the supporting means 30 is set.

For setting the rotary center, the supporting means 30 is moved and controlled by the above-mentioned XY table 62, the object holding means 40 is moved and controlled by the above-mentioned XY table 64, or the supporting means 30 and the object holding means 40 are simultaneously moved and controlled by the XY table 62 and by the XY table 64 respectively, thereby controlling the position of the objective radiography area of the object "o" relative to the dental arch DA.

According to the present invention, to position at least one of the object "o" to be examined and the supporting means 30 at a preferable place for radiography of the object "o" is called as positioning of the object. To move and control at least one of the supporting means 30 and the object holding means 40 as mentioned above is positioning of the object. When it is not required to move the object "o", the supporting means 30, or both the object "o" and the supporting means 30, it only needs to hold the object "o" with the object holding means 40. In this case, holding the object "o" with the object holding means 40 is included in positioning of the object.

The illustration p#2 as shown in FIG. 8 may be used as a scout image. The illustration p#2 is a plan view of a standard dental arch DA on which a horizontal cursor hc and a vertical cursor vc are overlapped and displayed and the interested area "r" surrounded with a circular frame is designated where they intersects. Local computer tomography after designating the interested area "r" is the same as that after the interested area "r" is designated in the above-mentioned structure in which the panoramic image p#1 is produced and displayed as a scout image.

Referring to each step in the flow chart of FIG. 20, producing a panoramic image p#1 is shown in the step 2010, and displaying the panoramic image p#1 as a scout image is shown in the step 2015.

In case that the illustration of p#2, not shown, of the dental arch which is illustrated from the panoramic image p#1 is used instead of the panoramic image p#1, production of the illustration p#2 is shown in the step 2025. Displaying the illustration p#2 as a scout image is shown in the step 2015.

In case of using the illustration p#2 as shown in FIG. 8 as a scout image, production of the illustration p#2 is shown in the step 2025. Displaying the illustration p#2 as a scout image is shown in the step 2015.

According to the local computer tomography which is designed to be executed here, the area to be irradiated is limited to the interested area "r", so that such a radiography is desirable in view of reducing the exposed dosage.

The transmitted image p#3 as shown in FIG. 9 can be used as a scout image as described referring to FIG. 9. The transmitted image p#3 to be used here can be obtained as a projection image when the above-mentioned broad X-ray beam is irradiated from two directions. An operator moves and controls a pointer by operating a mouse on the transmitted image p#3 in two directions to designate the interested area "r". The local computer tomography to be executed thereafter is the same as that after the position of the interested area "r" is specified on a scout image in the structure that the above-mentioned panoramic image p#1 is produced and displayed as a scout image.

The direction to be irradiated to obtain the transmitted image p#3 is not limited to two, however, it is not always two as far as the transmitted image projected from a plurality of directions can be obtained.

It is required to set the coordinate of the dental arch model dm in the coordinate of the space for executing computer tomography in order to specify the position of the designated interested area "r" relative to the dental arch model dm.

The similar dental arch model dm as mentioned referring to a broad computer tomography can be basically used as a dental arch model dm as mentioned later, so that the dental arch model dm may be set relative to the special position of the object holding means 40 as shown in FIG. 17*a* and FIG. 17*b* when the transmitted image p#3 from two directions is used as a scout image.

Referring to the flow chart of FIG. 20, production of the transmitted image p#3 in two directions is shown in the step 2020 in the flow chart of FIG. 20, display of the produced transmitted image p#3 in two directions is shown in the step 2015, designation of the interested area "r" is shown in the step 2040, and execution of a local computer tomography is shown in the step 2050.

In the prior art, it is known that in case of executing a local computer tomography by means of the X-ray CT apparatus M a guide light at Z-position spreading horizontally so as to guide the position of the area to be radiographed (objective radiography area) rr in a Z-axis direction and a guide light at Y-position spreading perpendicularly so as to guide the position of the area to be radiographed (objective radiography area) rr in a Y-axis direction are irradiated from the forward of the object "o", a guide light at X-position spreading perpendicularly so as to guide the area to be radiographed (objective radiography area) rr in an X-axis direction is irradiated from the right side and the left side of the object "o", and the area to be radiographed (objective radiography area) rr is set at the intersecting point of these guide lights (the actual common intersecting point is not seen from an operator so that its position is presumed).

The common intersecting point of the guide light at Z-position, the guide light at Y-position and the guide light at X-position is set so as to display the position of the area to be radiographed (objective radiography area) rr from a position designating data. The operator controls and positions the object "o" in such a manner that the interested area "r" is included in the area to be radiographed (objective radiography area) rr.

Referring to the flow chart of FIG. 20, the guide light at Z-position, the guide light at Y-position and the guide light at X-position are tools for specifying position, and positioning of the object to be examined "o" is shown in the step 2030 in the flow chart of FIG. 20. The interested area "r" is designed to be included in the area to be radiographed (objective radiography area) rr by such a positioning, thereby executing a local computer tomography. Therefore, specifying of position is designating of the interested area "r" and corresponds to the step 2040. Execution of a local computer tomography is shown in the step 2050.

For positioning the object to execute a local computer tomography, a positioning method using the pattern diagram of the dental arch is applicable and is also capable of designating the interested area "r" by such positioning.

The illustration p#2 for positioning, which is shown with an illustration p#21 of the pattern diagram of the dental arch DA, is displayed on the display means 88' of the operation panel 74 in FIG. 2 as shown in FIG. 2*c*. A circular illustration p#22 showing the objective radiography area is overlapped and shown on the illustration p#21. The direction display v' showing the standard observational direction "v" may be overlapped and displayed on the illustration p#22 of the objective radiography area as shown with an arrow.

The position of the objective radiography area of the object "o" can be relatively controlled relative to the dental arch DA by the movement control of the support means 30 by the above-mentioned XY table 62, the movement control of the object holding means 40 by the above-mentioned XY table 64, and the movement control of the total movement of both the support means 30 by the above-mentioned XY table 62 and the object holding means 40 by the above-mentioned XY table 64. According to the displacement amount of the movement control, the position of the illustration p#22 of the objective radiography area is designed to be moved relative to the illustration p#21 of the pattern diagram of the dental arch.

The position of the illustration p#22 of the objective radiography area may be moved relative to the illustration p#21 of the pattern diagram of the dental arch by operating the input means 74' and the movement control of the support means 30 by the above-mentioned XY table 62 and the movement control of the object holding means 40 by the above-mentioned XY table 64 may be executed in conjunction with the movement control of the illustration p#22.

The illustration p#21 of the pattern diagram of the dental arch corresponds to the dental arch model dm, so that when the objective radiography area is designated as the interested area "r", the positional relation of the interested area "r" relative to the dental arch model dm can be specified.

According to such a structure, the standard observational direction "v" can be specified by designating the objective radiography area by positioning the object "o" so as to execute a local computer tomography of the interested area "r". After such positioning, a local computer tomography is executed and the standard observational X-ray CT image of the interested area "r" can be displayed from the obtained CT image data.

Referring to each step in the flow chart of FIG. 20, the illustration p#21 of the pattern diagram of the dental arch, the illustration p#22 of the objective radiography area, and the input means 74' are tools for specifying position, and specifying of the position is executed in the step 2030 in the flow chart of FIG. 20 because positioning of the object "o" is specifying of the position. The interested area "r" is included in the area to be radiographed (objective radiography area) rr by such a positioning and then a local computer tomography is executed, so that specifying of position is designation of the interested area "r" and corresponds to the step 2040. A local computer tomography is executed in the step 2050.

As explained referring to FIG. 14, the operation panel having the illustration p#2 may be used for designating the interested area "r". When the code is specified by operating the button bt, the standard position of each tooth th allotted with the code is specified and positioning is executed. For this purpose, a standard position is set in advance for each tooth th.

A method without using an image can be used for designating the interested area "r". For example, the code allotted for the tooth th is selected by means of the operation means 86 for specifying the position and the interested area "r" may be designated. The interested area "r" is positioned at the standard position of the selected tooth th. A local computer tomography thereafter is the same as mentioned above.

Referring to each step in the flow chart of FIG. 20, the illustration p#2, the button bt of the operation panel 75, the operation means 86 and the code allotted for a tooth th are tools for specifying position, and positioning of the object "o" is specifying of position. Therefore, it corresponds to the step 2030 in the flow chart of FIG. 20. The interested area "r" is included in the area to be radiographed (objective radiography area) rr by such a positioning and then a local computer tomography is executed, so that specifying of position is designating of the interested area "r" and corresponds to the step 2040. A local computer tomography is executed in the step 2050.

The dental arch model dm which is explained referring to a broad computer tomography can be basically used as a dental arch model dm in a method of obtaining the standard observational direction "v".

Designation of the interested area "r" in case of a broad computer tomography means specifying of an objective area to be displayed. However, designation of the interested area "r" in a local computer tomography means specifying of the area to be radiographed (objective radiography area) rr. In spite of such difference, it requires to make the area to be radiographed (objective radiography area) rr the objective area to be displayed in case of a local computer tomography, so that designation of the area to be radiographed (objective radiography area) rr in case of a local CT may be considered to designate the objective area to be displayed. It may be possible that the operations are separately executed, namely designating of the interested area "r" which means designating of the area to be radiographed (objective radiography area) rr and designating of the interested area "r" for designating the coordinate and position of the interested area "r" relative to the coordinate and position of the dental arch model dm. However, in such a case, designating of the interested area "r" should be executed two times. Therefore, it is preferable to execute by one time designating of the area to be radiographed (objective radiography area) rr and designating of the interested area "r" for designating the coordinate and position of the interested area "r" relative to the coordinate and position of the dental arch model dm. The structure of specifying the position of the interested area "r" relative to the dental arch model dm is common, so that setting of the standard observational direction "v" and slice position sl is basically same in case of a broad computer tomography.

Accordingly, the structures shown in FIG. 23, FIG. 23A to FIG. 23E, and FIG. 15 can be used for setting the standard observational direction "r" and the slice position sl.

As mentioned above, if the interested area "r" is designated, the object is positioned and a local computer tomography is executed for the designated interested area "r" as the radiography object according to the mechanical structure of the X-ray CT apparatus body M1. The coordinate information and positional information of the dental arch model dm and the coordinate information and positional information of the interested area "r" can be figured out, so that the coordinate and position of the interested area "r" can be specified relative to the coordinate and position of the dental arch model dm. When the coordinate and position of the interested area "r" relative to the coordinate and position of the dental arch model dm are specified, the standard observational direction "v" and the slice position sl can be set.

If a scout image is a panoramic image p#1, the panoramic section to be produced as an image is set in a three-dimensional space in case of a panoramic radiography. The panoramic section can be used as a dental arch model dm. The panoramic image p#1 which is an image of the panoramic section corresponds to an extended standard curved plane of the dental arch model dm, so that the objective radiography area can be designated by corresponding the specified position, namely coordinate, of the panoramic image p#1 and the coordinate of the dental arch model dm and by specifying a specific position (coordinate) of the panoramic image p#1. It can be designed to specify a specific coordinate of the corresponding dental arch model dm at the same time.

The interested area "r" may be designated for specifying the coordinate and position of the interested area "r" relative to the coordinate and position of the dental arch model dm separately from designating of the interested area "r" as an objective radiography area. For example, the objective radiography may be designated by designating the interested area "r" on the panoramic image p#1, and further, separately from such a designating operation, the interested area "r" may be designated at the same position on the panoramic image p#1 so as to specify the coordinate and position of the interested area "r" relative to the coordinate and position of the dental arch model dm. In such a case, designation of the interested area "r" should be executed twice and it is preferable to complete designating of the objective radiography area and designating of the coordinate and position of the interested area "r" relative to the coordinate and position of the dental arch model dm by one designation.

As mentioned above, if the interested area "r" namely the objective radiography area is designated using the illustration p#2, not shown, which is an illustration of the panoramic image p#1, instead of using the panoramic image p#1, the specific coordinate of the corresponding dental arch model dm can be designed to be specified by specifying a specific position (coordinate) of the illustration p#2, wherein the illustration P#2 is formed by extending a standard shaped dental arch model dm in a form of a flat plane as mentioned above.

When the interested area "r" namely the objective radiography area is designated as the scout image using the illustration p#2 modeling the plan view of the dental arch DA, its shape corresponds to the shape in which the standard curved plane of the dental arch model dm is seen from the top and the dental arch model dm is designed to be overlapped at the portion corresponding to the panoramic section at the center of the dental arch DA shown in the illustration p#2.

A specific coordinate of the corresponding dental arch model dm can be specified by specifying a specific position (coordinate) on the illustration p#2.

If the interested area "r" namely the objective radiography area is designated using the transmitted image p#3 shown in FIG. 9 as a scout image as explained referring to FIG. 9, a specific coordinate of the corresponding dental arch model dm can be specified by specifying a specific position (coordinate) on the transmitted image p#3 in two directions.

When the interested area "r" namely the objective radiography area is designated using the Z-position guide light, the Y-position guide light and the X-position guide light, a detection means for detecting the movement amount of the support means 30 and the object holding means 40 is provided so as to detect the position (coordinate) of the intersecting point which is common to the Z-position guide light, the Y-position guide light and the X-position guide light and the position (coordinate) of the objective radiography area can be detected following the positioning of the object. A specific coordinate of the corresponding dental arch model dm is designed to be specified by specifying a specific position (coordinate) by positioning the object.

For positioning the object in case of a local computer tomography, when the interested area "r" namely the objective radiography area is designated by displaying the circle illustration p#22 showing an objective radiography area overlapped on the illustration p#21 for positioning shown in FIG. 2c, a detection means is provided for detecting the movement control amount of the support means 30 by the XY table 62 and of the object holding means 40 by the XY table 64, and the position (coordinate) of the objective radiography area can be detected following the positioning of the object. In this structure, a specific coordinate of the corresponding dental arch model dm is designed to be specified by specifying a specific position (coordinate) by positioning the object.

When the code allotted for the tooth th may be selected with the operation means 86 to designate the interested area "r" namely the objective radiography area, a specific coordinate of the corresponding dental arch model dm can be specified by selecting a specific position (coordinate) with a code.

Or when the interested area "r" namely the objective radiography area is designated by operating the button bt using the operation panel with the illustration p#2 as explained referring to FIG. 14, a specific coordinate of the corresponding dental arch model dm can be specified by selecting a specific position (coordinate) by operating the button bt.

The code allotted for the tooth th is selected to specify the position by means of the operation means 86 without using an image for designating the interested area "r", a specific coordinate of the corresponding dental arch model dm can be specified by selecting a specific position (coordinate) by a code.

In any cases, the coordinate information and positional information of the dental arch model dm and the coordinate information and positional information of the interested area "r" can be understood, so that the coordinate and position of the interested area "r" can be specified relative to the coordinate and position of the dental arch model dm.

A dental arch model dm which is prepared in advance from a generally shaped dental arch DA as shown in FIG. 23, FIG. 23A to FIG. 23E and FIG. 15 can be used as a dental arch model dm. Specifying of the coordinate and position of the interested area "r" relative to the dental arch model dm is to specify the positional relation of the dental arch model dm and the interested area "r" and corresponds to the steps 2060, 2065 in the flow chart of FIG. 20.

The fact that the coordinate and position of the interested area "r" relative to the coordinate and position of the dental arch model dm are specified and that the standard observational direction "v" and the slice position sl are set is the same as that explained referring to FIG. 23, FIG. 23A to FIG. 23E and FIG. 15.

Setting of the standard observational direction "v" and slice position sl as shown in FIG. 23, FIG. 23A through FIG. 23E and FIG. 15 is to set the standard observational direction "v" and the slice position sl of the interested area from the dental arch reference information corresponding to the designated interested area "r" and corresponds to the step 2092 in the flow chart of FIG. 20.

When the standard observational direction "v" and the slice position sl are set, the CT data obtained by executing a local computer tomography for the object "o" is rendered to an image processing to reconstruct the standard observational X-ray CT image of the interested area "r". Reconstructing of the standard observational X-ray CT image of the interested area "r" corresponds to the step 2100 in the flow chart of FIG. 20.

The standard observational direction "v" for each tooth th may be determined in advance and the same code as FIG. 14 may be allotted for each tooth th in the same manner as explained referring to FIG. 18a in case of a brad computer tomography. If a look-up table which provides each tooth th and corresponding standard observational direction "v" is prepared in advance, the standard observational direction "v" can be immediately obtained by selecting the code of the tooth th to be seen from the front. Otherwise, a look-up table which provides each tooth th and corresponding slice position sl as described referring to FIG. 23, and FIG. 23A to FIG. 23E may be prepared. Or a look-up table may provide each position capable of designating as an interested area "r" and the standard observational direction "v" or slice position sl at the position.

The code allotted for the tooth th may be selected by the operation panel 74 or the operation means 86.

The code selection of tooth th to be viewed from the font and designation of the interested area "r" may be incorporated. Namely, when the tooth th is selected by operating the button bt or inputting the code as explained referring to FIG. 14 in case of a broad CT, the interested area "r" including the tooth th may be automatically designated and the look-up table is referred depending on the positional information of the interested area. Or when the interested area "r" is designated, the tooth th at the center of the interested area "r" may be automatically selected and the look-up table is referred depending on the selection information of the tooth th. Such a look-up table can be obtained by processing the image data of the dental arch DA or actually measuring the shape of the dental arch DA like the dental arch model dm.

In this case, the code, the look-up table and the code, and the standard observational direction "v" or the slice position sl specified by the look-up table are the dental arch reference information corresponding to the interested area "r". Determining the standard observational direction "v" and the slice position sl using these information is shown in the steps 2080, 2090 in the flow chart of FIG. 20.

A method of obtaining the standard observational direction "v" by image analysis may be used as another method of obtaining the standard observational direction "v".

For example, as shown in FIG. 21, a local computer tomography of the interested area "r" is completed and a plurality of slice image data are obtained from the reconstructed three-dimensional CT data. There may be an image in which a jaw bone LI at the tongue side and a jaw bone LO at the cheek side are clearly seen like a slice plane image ZH3 in the figure among the slice image data. Such an image clearly showing the jaw bone LI at the tongue side and the jaw bone LO at the cheek side is detected by pattern acknowledgement of an image software, and the lines of the jaw bone LI and the jaw bone LO are recognized in the detected image, thereby calculating the approximate center line CL thereof. If the line CL is curved, the tangent line TG to the line CL which is at the enter or substantially at the center of the interested area "r" can be calculated. The standard observational direction "v" is a direction perpendicular to the tangent line TG.

It is possible to reconstruct CT data and produce a sectional image developing vertically at the slice position Sl by an image processing.

When the sectional image in which the interested area "r" is viewed from the standard observational direction "v" is produced, it is optional that where the sectional plane, namely the slice position sl, is set. The slice position sl may be set at the position of the tangent line TG, or it may be set at other place as explained referring to FIG. 23 and FIG. 23A-FIG. 23E.

The pattern of the jaw bone LI at the tongue side and the jaw bone LO at the cheek side which exist at different height can be recognized as mentioned above, so that the center line CL can be continued up and down to form a plane as a dental arch model dm. Also the tangent line TG may be continued up and down to form a plane, which may be used as the standard observational sectional plane.

Recognizing the lines of the jaw bone LI and the jaw bone LO by such image analysis and calculating a substantial center line CL are to obtain the dental arch model dm by image analysis. Namely, the center line CL is a kind of the dental arch model dm. It corresponds to the step 2070 in FIG. 20. Calculating the tangent line TG to the line CL at the center or the substantial center P1 of the interested area "r" is to specify the positional relation of the dental arch model dm and the interested area "r" and it corresponds to the step 2065 in FIG. 20. Obtaining the standard observational direction "v" orthogonal to the tangent line TG and the slice position sl is determining the standard observational direction "v" and the slice position sl of the interested area "r" from the dental arch reference information corresponding to the designated interested area "r" and it corresponds to the step 2090 in FIG. 20.

Now explained is an example of the standard observational X-ray CT image displayed according to the above basic procedure.

Figure 22A:
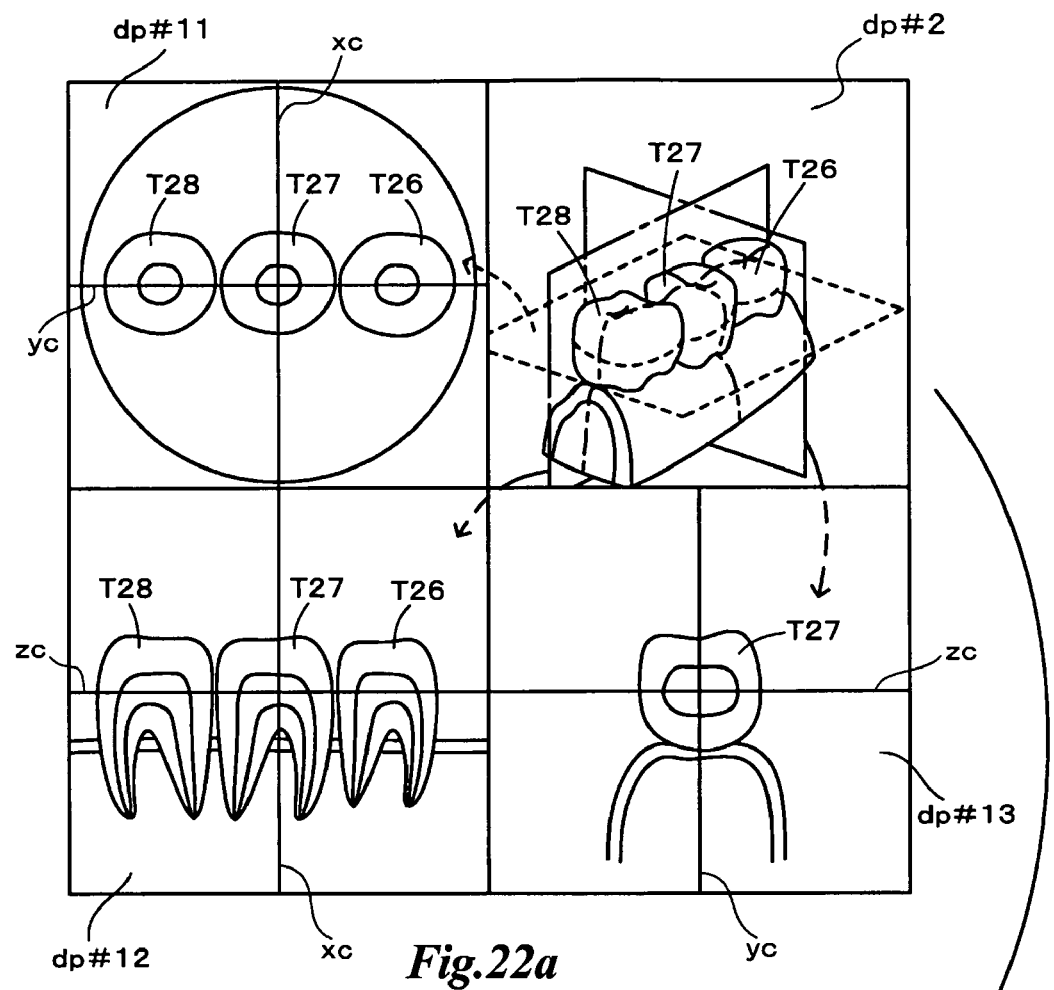
FIG. 22a is other example of a standard observational X-ray CT sectional image of an interested area and FIG. 22b shows other embodiment of a standard observational three-dimensional CT volume image of an interested area.
Figure 22B:
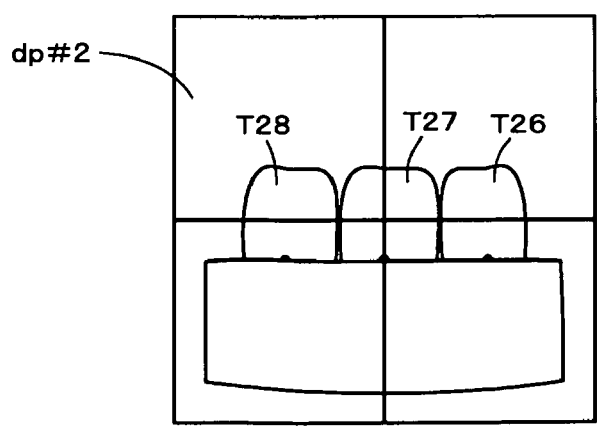

FIG. 22a shows an X-ray CT sectional images dp#11-dP#13 of a Z-section, a Y-section, and an X-section which are orthogonal each other and produced from the CT data obtained by a local computer tomography of the area to be radiographed (objective radiography area) rr including the interested area "r". The X-ray CT sectional image dp#12 is a standard observational X-ray CT image and is shown at such an angle that the longitudinal direction of the dental arch DA in the interested area "r" goes along the Y-cursor yc. When any one of the cursors xc, yc, zc is operated to be moved, the X-ray CT sectional image dp#11-dp#13 is changed and displayed following the operation so as to display the image of the section at the position corresponding to the cursors xc, yc, zc. The codes "T26", "T27", "T28" are the same codes as the code "26", "27", "28" which are allotted to each tooth th in FIG. 14.

FIG. 22a shows a three-dimensional CT volume image dp#2 which is seen obliquely and is produced from the CT data obtained by a local computer tomography. Otherwise, a three-dimensional CT volume image dp#2 produced as the standard observational X-ray CT image may be displayed like FIG. 22b.

Referring to the step in the flow chart of FIG. 20, producing the standard observational X-ray CT image dp is shown in the step 2100, displaying the sectional image dp#12 as the standard observational X-ray CT image is shown in the step 2110, and displaying the three-dimensional CT volume image dp#2 as the standard observational CT image is shown in the step 2120.

The invention claimed is:

1. A display method for an X-ray CT image of a maxillofacial area of an object to be examined which is obtained from an X-ray computer tomography, for use in an X-ray CT apparatus or an X-ray CT image display apparatus, said method comprising the steps of:
    designating an interested area with respect to said maxillofacial area of an optional position on a dental arch of said object,
    upon receiving designating operation, producing by means of an image processing means a standard observational X-ray CT image of said designated interested area and other X-ray CT image normal to said standard observational X-ray CT image from the image data of said maxillofacial area of said object, based on a dental arch reference information prepared in advance for specifying a direction substantially normal to a curve of a dental arch of said object from its cheek side to its tongue side, said standard observational X-ray CT image being an X-ray CT image of said object seen in a direction substantially normal to a curve of the dental arch from its cheek side to its tongue side; and
    displaying on a display means in array said standard observational X-ray CT image and said other X-ray CT image normal to said standard observational X-ray CT image.

2. The display method as set forth in claim 1, wherein the image data of said maxillofacial area of said object is obtained from an X-ray computer tomography for an entire jaw of said object.

3. The display method as set forth in claim 1 or 2, wherein said method further comprises a step of producing a sectional image of an X-sectional plane, a Y-sectional plane and a Z-sectional plane, which are orthogonal each other and produced from a three-dimensional CT data of said object produced by reconstructing the image data of said maxillofacial area of said object, and
    in said step of designating said interested area, at least one of said X-sectional plane, said Y-sectional plane and said Z-sectional plane thus produced is displayed to designate said interested area thereon.

4. The display method as set forth in claim 1 or 2, wherein said method further comprises a step of displaying selectively some of X-ray transmitted images of said object in different angles obtained from said X-ray computer tomography of said maxillofacial area of said object, and
    in said step of designating said interested area, said interested area is designated on said X-ray transmitted images thus selectively displayed.

5. The display method as set forth in claim 1, wherein the image data of said maxillofacial area of said object is obtained from a local X-ray computer tomography for a part of said maxillofacial area of said object.

6. The display method as set forth in claim 1 or 2 , wherein said method further comprises a step of producing a panoramic image from an X-ray panoramic radiography for said object executed in addition to said X-ray computer tomography, and in said step of designating said interested area, said X-ray panoramic image is displayed to designate said interested area thereon.

7. The display method as set forth in claim 1 or 2, wherein said method further comprises a step of producing a panoramic image by combining partial data of a plurality of X-ray transmitted image data of said object in different angles, said plurality of X-ray transmitted images of said object being obtained when said X-ray computer tomography is executed, and in said step of designating said interested area, said panoramic image is displayed to designate said interested area thereon.

8. The display method as set forth in claim 1 or 2, wherein in said step of designating said interested area, an illustration image data in the shape of dental arch with respect to said object is displayed to designate said interested area thereon.

9. The display method as set forth in claim 1 or 2, wherein said method further comprises a step of producing a three-dimensional CT volume image as seen in a direction normal to said interested area, and in said step of displaying said standard observational X-ray CT image, said three-dimensional CT volume image is shown in combination with said standard observational X-ray CT image of said designated interested area and said other X-ray CT image normal to said standard observational X-ray CT image.

10. The display method as set forth in claim 1, wherein said standard observational X-ray CT image is a cross-sectional image of a plane tangential to a curve of said dental arch.

11. An X-ray CT apparatus for displaying an X-ray CT image of a maxillofacial area of an object to be examined, having an X-ray generator, an X-ray detector, a moving means for relatively moving the X-ray generator and the X-ray detector relative to the maxillofacial area of the object, and an object holding means on which the object is set up, wherein said apparatus comprising:

a designation means of interested area for designating said interested area on said maxillofacial area with respect to an optional position on a dental arch of said object;

upon receiving designating operation, an image processing means for producing a standard observational X-ray CT image of said designated interested area and other X-ray CT image normal to said standard observational X-ray CT image from the image data of said maxillofacial area of said object, based on a dental arch reference information prepared in advance for specifying a direction substantially normal to a curve of a dental arch of said object from its cheek side to its tongue side, said standard observational X-ray CT image being an X-ray CT image of said object as seen in a direction substantially normal to a curve of the dental arch from its cheek side to its tongue side; and a display means for displaying in array said standard observational X-ray CT image and said other X-ray CT image normal to said standard observational X-ray CT image.

12. The X-ray CT apparatus as set forth in claim 11, wherein said X-ray computer tomography is executed for an entire jaw of said object by driving said moving means to obtain said image data of said maxillofacial area of said object.

13. The X-ray CT apparatus as set forth in claim 11 or 12, wherein said image processing means produces and displays a sectional image of an X-sectional plane, a Y-sectional plane and a Z-sectional plane, each of images being orthogonal each other, which are produced from a three-dimensional CT data of said object produced by reconstructing the image data of said maxillofacial area of said object; and said designation means of interested area receives operation for designation of said interested area on at least one of said X-sectional plane, said Y-sectional plane and said Z-sectional plane thus produced.

14. The X-ray CT apparatus as set forth in claim 11 or 12, wherein said display means selectively displays some of X-ray transmitted images of said object in different angles obtained from said X-ray computer tomography of said maxillofacial area of said object, and said designation means of interested area receives operation for designation of said interested area on said X-ray transmitted images thus selectively displayed.

15. The X-ray CT apparatus as set forth in claim 11, wherein said X-ray computer tomography is executed for a part of said maxillofacial area of said object by driving said moving means.

16. The X-ray CT apparatus as set forth in claim 11 or 12, wherein

X-ray panoramic radiography is executed in addition to said X-ray computer tomography by driving said moving means, said image processing means produces a panoramic image, and said designation means of interested area displays said panoramic image thus produced to receive an operation for designation of said interested area thereon.

17. The X-ray CT apparatus as set forth in claim 11 or 12, wherein said image processing means produces a panoramic image by combining partial data of a plurality of X-ray transmitted image data of said object in different angles, said plurality of X-ray transmitted images of said object being obtained by executing said X-ray computer tomography, and said designation means of interested area receives operation for designation of said interested area on said panoramic image.

18. The X-ray CT apparatus as set forth in claim 11 or 12, wherein said apparatus further comprises an illustration display means for displaying an illustration image data in the shape of dental arch with respect to said object, prepared in advance, and said designation means of interested area receives operation for designation of said interested area on said illustration image data.

19. The X-ray CT apparatus as set forth in claim 11 or 12, wherein said apparatus produces a three-dimensional CT volume image seen in a direction normal to said interested area, and said apparatus displays said standard observational X-ray CT image and said three-dimensional CT volume image is shown in combination with said standard observational X-ray CT image of said designated interested area and said other X-ray CT image normal to said standard observational X-ray CT image.

20. The X-ray CT apparatus as set forth in claim 11, wherein said standard observational X-ray CT image is a cross-sectional image of a plane tangential to a curve of said dental arch.

21. An X-ray CT image display apparatus for displaying a standard observational X-ray CT image from a maxillofacial area image of an object to be examined obtained by an X-ray computer tomography, said display apparatus comprising;

a designation means of interested area for designating said interested area on said maxillofacial area with respect to an optional position on a dental arch of said object;

upon receiving designating operation, an image processing means for producing a standard observational X-ray CT image of said designated interested area and other X-ray CT image normal to said standard observational X-ray CT image from the image data of said maxillofacial area of said object, based on a dental arch reference information prepared in advance for specifying a direction substantially normal to a curve of a dental arch of said object from its cheek side to its tongue side, said standard observational X-ray CT image being an X-ray CT image of said object as seen in a direction substantially normal to a curve of the dental arch from its cheek side to its tongue side; and a display means for displaying in array said standard observational X-ray CT image and said other X-ray CT image normal to said standard observational X-ray CT image.

22. The X-ray CT image display apparatus as set forth in claim 21, wherein said standard observational X-ray CT image is a cross-sectional image of a plane tangential to a curve of said dental arch.

* * * * *